(12) United States Patent
Koike

(10) Patent No.: US 7,732,180 B2
(45) Date of Patent: Jun. 8, 2010

(54) PORCINE FORSSMAN SYNTHETASE PROTEIN, CDNA, GENOMIC ORGANIZATION, AND REGULATORY REGION

(75) Inventor: Chihiro Koike, Pittsburgh, PA (US)

(73) Assignee: University of Pittsburgh of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 11/125,572

(22) Filed: May 9, 2005

(65) Prior Publication Data

US 2006/0068479 A1     Mar. 30, 2006

Related U.S. Application Data

(60) Provisional application No. 60/568,922, filed on May 7, 2004.

(51) Int. Cl.
*C12N 9/10* (2006.01)
*C12N 15/70* (2006.01)
*C12N 5/16* (2006.01)
*C12P 21/06* (2006.01)
*C07H 21/04* (2006.01)

(52) U.S. Cl. .................. 435/193; 435/440; 435/455; 435/325; 435/320.1; 536/23.2

(58) Field of Classification Search ............... 435/183, 435/191, 193, 69.1, 320.1; 536/23.2
See application file for complete search history.

(56) References Cited

U.S. PATENT DOCUMENTS

| | | | |
|---|---|---|---|
| 6,166,288 A | 12/2000 | Diamond et al. | |
| 6,331,658 B1 | 12/2001 | Cooper et al. | |
| 2003/0153044 A1 | 8/2003 | Liljedahl et al. | |
| 2005/0108783 A1 | 5/2005 | Koike | |
| 2005/0155095 A1 | 7/2005 | Koike | |
| 2005/0233418 A1 | 10/2005 | Baum et al. | |

FOREIGN PATENT DOCUMENTS

| | | |
|---|---|---|
| WO | WO 00/51424 A2 | 9/2000 |
| WO | WO 01/23541 A2 | 4/2001 |
| WO | WO 03/059923 A2 | 7/2003 |

OTHER PUBLICATIONS

Haslam et al. GenBank Accession No. U66140, "Canis familiaris Forssman synthetase mRNA, complete cds", created Oct. 23, 1996.*
Whisstock et al. Prediction of protein function from protein sequence and structure, Q Rev Biophys. Aug. 2003;36(3):307-40. Review.*
Kano et al. Establishment of hepatic stem-like cell lines from normal adult porcine liver in a poly-D-lysine-coated dish with NAIR-1 medium, in Vitro Cell Dev Biol Anim. Nov.-Dec. 2003;39(10):440-8.*
van den Berg et al. Role and regulation of pig CD59 and membrane cofactor protein/CD46 expressed on pig aortic endothelial cells, Transplantation. Aug. 27, 2000;70(4):667-73.*
Altschul, S.F., et al., "Gapped BLAST and PSI-BLAST: a new generation of protein database search programs," *Nucleic Acid Res.*, 25(17):3389-3402 (Sep. 1, 1997).
Cooper, D.K.C., et al., "Identification of alpha-galactosyl and other carbohydrate epitopes that are bound by human anti-pig antibodies: relevance to discordant xenografting in man," *Transpl. Immunol.*, 1(3):198-205 (1993).
Dai Y., et al., "Targeted disruption of the $\alpha 1,3$-galactosyltransferase gene in cloned pigs," *Nature Biotechnology*, 20:251-255 (Mar. 2002).
Haslam, G.B., and Baenziger, J.U., "Expression cloning of Forssman glycolipid synthetase: a novel member of the histo-blood group ABO gene family," *Proc. Natl. Acad. Sci. U S A.*, 93(20):10697-10702 (Oct. 1, 1996).
Lublin, D.M., et al., "Molecular cloning and chromosomal localization of human membrane cofactor pro-tein (MCP). Evidence for inclusion in the multigene family of complement-regulatory proteins," *J. Exp. Med.*, 168(1): 181-194 (Jul. 1, 1988).
Medof, M.E., et al., "Cloning and characterization of cDNAs encoding the complete sequence of decay-accelerating factor of human complement," *Proc. Natl. Acad. Sci. USA*, 84(7):2007-2011 (Apr. 1987).
Phelps, C.J., et al., "Production of $\alpha 1,3$-galactosyltransferase-deficient pigs," *Science*, 299:411-414 (Jan. 17, 2003).
Philbrick, W.M., et al., "The CD59 antigen is a structural homologue of murine Ly-6 antigens but lacks interferon inducibility," *Eur. J. Immunol.*, 20(1):87-92 (Jan. 1990).
Tiscornia, G., et al.. *Proc. Natl. Acad. Sci. USA*, 100(4):1844-1848 (Feb. 18, 2003); published elec-tronically Jan. 2003.
Xu, H., et al., "Characterization of the human Forssman synthetase gene. An evolving association between glycolipid synthesis and host-microbial interactions," *J. Biol. Chem.*, 274(41):29390-29398 (Oct. 8, 1999).

* cited by examiner

*Primary Examiner*—Richard Hutson
*Assistant Examiner*—Iqbal H Chowdhury
(74) *Attorney, Agent, or Firm*—King & Spalding

(57) ABSTRACT

The present invention provides porcine Forssman synthetase (FSM synthase) (Globoside $\alpha$-N-acetylgalactosaminyltransferase) protein, cDNA, and genomic DNA sequence. Furthermore, the present invention includes porcine animals, tissue and organs as well as cells and cell lines derived from such animals, tissue and organs, which lack expression of functional FSM synthetase. Such animals, tissues, organs and cells can be used in research and in medical therapy, including in xenotransplantation. In addition, methods are provided to prepare organs, tissues, and cells lacking the porcine FSM synthetase gene for use in xenotransplantation.

7 Claims, 4 Drawing Sheets

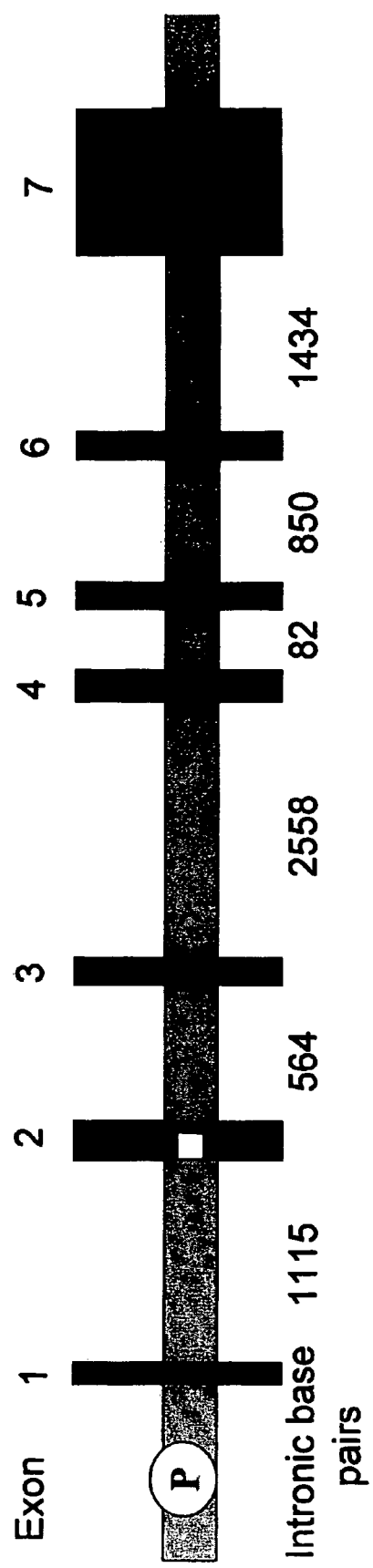
Figure 1: Genomic Organization of the Porcine FSM Synthetase Gene.

```
TGAATTCTAGCTCCGTCGTCGCCTACGCTGGTCCGACCGCAAGGGGTCTCCTCCGAGACCCCGAAGACACAAGCTCAGAGCCTGACGG
CCCTGAGAGAGGTGGGCGGATCGGCAAGTCACACCCAGGCTCTGCCAGGTGCTCAGCCCAGACGCTGCACCCAGAGATGCGC
TGCCGCAGACTAGCCCTGGGCTTCGGCTGCTGGTGCCCTGTGCCCTGCTGCTGTGGCGTCTCTGTGGCGTGTATGTGGAGAACGTGC
CGCCGGTCTATATCCCCTATTACCTCCCCTGCCCTGAGATCTTCAACATGAAGCTCCAGTACAAGGGGGTGAAGCCATTCCA
GCCCGTGGCACAGTCCCAGTACCCTCAGCCAAGCTGCTTGAGCCTGAGCTTCTCATCACATCTACCAGAGCTCCTGAGCGTCCTGGTTGGCA
CCATCGTCTCCGAGGGCAACCCTGGAGCTTGTCCAGTGCGCTTCTTCATGAGCCACTGAACCTGACCATCGGGCTCACGGTGTT
TGCCGTGGGGAAGTACACCCAGTTCGTCCAGGCCGTTCCTGGGGTCCGGTTCCCGCTGAGTCGGCGCTACCTCAGCGTACACTAC
TACATCTTTACCAGGACGAGCCGGGGGCCCATCAGCAGGAGGCCATCAGCACATTGCCGCCAGGGACCTGGTGGCTGCCATTCACCC
CCTCCCGCTGGGAGGAGGTCTCCACACGCCGATGGTGTTCCGGAACATGGGCGCCGGCATGTACGAGACCTCGTGGGCAGCAGCGAGGGGAC
ACCTCTTCGCCGCGCGAGTGCAGCGGGCTTCGCGCCGCCTTCACCAGGCTCACGAGTTCCAGGGTCTGCCACATGGGCATCCTGGCCG
GGGCTACTTCGGGCTAGTGCCCCAGCAGCAGGGTGTACGAGTCAACCGCGCTTCATCTCCCACAAGCCCTCCAAGGTGC
TTCTATTATGGTGGGCGGTCTTCGGGCCAATGGCATCATCCTGGGATGACCAGCAGCACTTCTCCCCCAGTCAAGCCCTGCCCCAGCA
CAACTGGCTGAGGAGCTGACAGCACAGCCGGGGCTGCTGTGCATGCGGGGGACCCCAGCTCGCCCCAGCA
GCGCTCCTCACCCGGACGCTCACTTCCCAAGCTCCCAGTGTGAAACAGCCCCCGCTGCCTGCCTACCTCTCCAGGCTGCCAGCAGACTC
CGAGGCTGTGTAAACTGTGAAAGAAGACGGGACCCCACCTGCCTTTGGGCGCTGGAGGGTCAGCCCTGCC
GACCAGAGGTAGAAGAAGACGGGACCCCACCCGCAGTCCCAGCGCCACTGCCTTTGTGCCTGACACATGAGAGAGGTATCTGGACCCCTGTCCTG
CAGTGCCTGACGTCCCGCCACCCGGGACTGTTCTGTCCCCCCTGCCACAAGGAGCCAGTACTTCACTCAGGACCCCGACCCCGAGCCTTCGAAATG
GCTGCAGGGCCCCGGGCTCTGGGCTCTGTCCACGTCCAGTCCAGTGAGCCCCTGGCCAGTGAGACCCTCCCTGGTGCCCACGCCTCCTTGCAAGG
GGGTTTGGGCAGCTTTTAATACAGGTGGCATGTGCTCAGCCCTAACC (Seq ID No. 1)
```

Figure 2: cDNA Sequence of Porcine FMS Synthetase

MRCRRLALGLGFGLLVGVALCSLWLYVENVPPPVYIPYYLPCPEIFNMKLQYK
GVKPFQPVAQSQYPQPKLLEPKPSELLTLTSWLAPIVSEGTFDPELLHHIYQPL
NLTIGLTVFAVGKYTQFVQRFLESAERFFMQGYRVHYYIFTSDPGAVPGVPLG
PGRLLSVIAIRRPSRWEEVSTRRMEAISQHIAARAHREVDYLFCLSVDMVFRNP
WGPETLGDLVAAIHPGYFAAPRQQFPYERRHVSTAFVADSEGDFYYGGAVFG
GRVARVYEFTQGCHMGILADKANGIMAAWQEESHLNRRFISHKPSKVLSPEYL
WDDRRPQPPSLKLIRFSTLDKDTNWLRS (Seq ID No. 2)

Figure 3: Amino Acid Sequence of Porcine FSM Synthetase

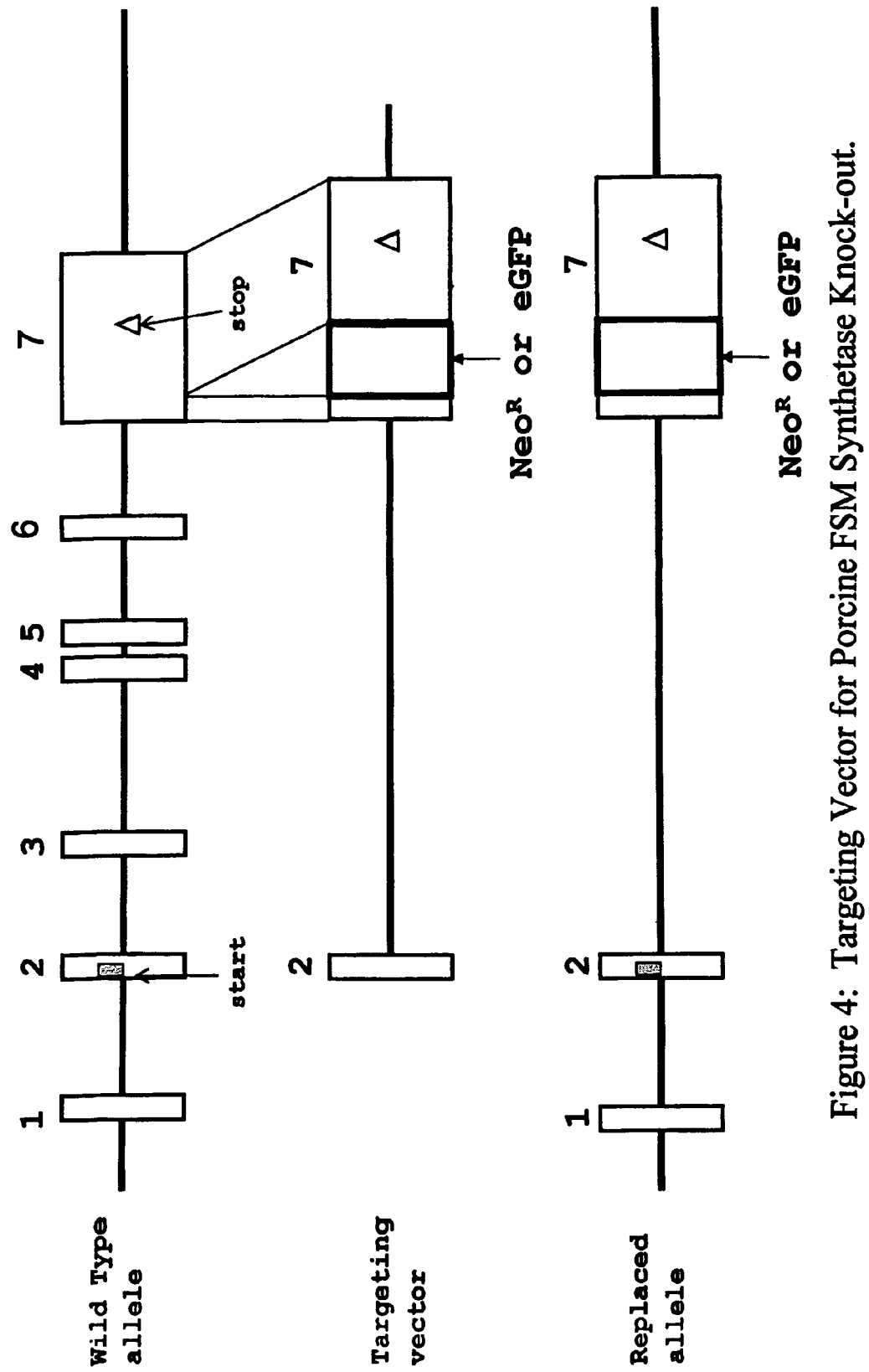
Figure 4: Targeting Vector for Porcine FSM Synthetase Knock-out.

SEQUENCE LISTING

<160> NUMBER OF SEQ ID NOS: 22

<210> SEQ ID NO 1
<211> LENGTH: 1831
<212> TYPE: DNA
<213> ORGANISM: Sus scrofa

<400> SEQUENCE: 1

```
tgaattctag ctccgtctgc ctacgctggt ccgaccgcaa ggggtctcct ccggaccccg      60
aagacacaag ctcagagcct gacggcccct gagagaggtg ggcggatccg ccaagtcaca     120
cccaggctct gcaggtgctc aggcccagac gctgcaccca gagatgcgct gccgcagact     180
agccctgggc ctggggttcg gcctgctggt gggcgtggcc ctctgctctc tgtggctgta     240
tgtggagaac gtgccgccgc cggtctatat cccctattac ctcccctgcc ctgagatctt     300
caacatgaag ctccagtaca aggggtgaa gccattccag cccgtggcac agtcccagta     360
ccctcagccc aagctgcttg agccaaagcc ctcagagctc ctgacgctca cgtcctggtt     420
ggcacccatc gtctccgagg gcaccttcga ccctgagctt cttcatcaca tctaccagcc     480
actgaacctg accatcgggc tcacggtgtt tgccgtgggg aagtacaccc agttcgtcca     540
gcgcttcctg gagtcggccg agcgcttctt catgcagggc taccgggtgc actactacat     600
ctttaccagc gaccccgggg ccgttcctgg ggtcccgctg ggcccgggcc gcctcctcag     660
cgtcatcgcc atccggagac cctcccgctg ggaggaggtc tccacacgcc ggatggaggc     720
catcagccag cacattgccg ccagggcgca ccgggaggtc gactacctct tctgcctcag     780
cgtggacatg gtgttccgga acccatgggg ccccgagacc ttgggggacc tggtggctgc     840
cattcacccg ggctacttcg ccgcgccccg ccagcagttc ccctacgagc gccggcatgt     900
ttctaccgcc ttcgtggcgg acagcgaggg ggacttctat tatggtgggg cggtcttcgg     960
ggggcgggtg gccagggtgt acgagttcac ccagggctgc cacatgggca tcctggcgga    1020
caaggccaat ggcatcatgg cggcctggca ggaggagagc cacctgaacc gccgcttcat    1080
ctcccacaag ccctccaagg tgctgtcccc cgagtacctc tgggatgacc gcaggcccca    1140
gccccccagc ctgaagctga tccgcttttc cacactggac aaagacacca actggctgag    1200
gagctgacac cacagccggg gctgctgtgc atgcgggggg accccaagcc ctgccccag    1260 ctcgccccag cagcgcctcc tcacccggac gcctcacttc ccaagccttc tgtgaaacca    1320
gccctgcgct gcctacctct caggctgcca gcagactccg aggcctgtgt aaactgtgaa    1380
gggctgtgcc cttgtgagaa cacacagcct gtgagccaga aacggtcaga cgggaggaga    1440
cggaccagag gtagaagaag acgggacccg cagtcctcac ccagcccacg tgcctttggg    1500
gtgggcgctg gagggtcagc cctgcccagt gcctgacgtc ccgcccaccc cccttttgtg    1560
gccgtttgta cctctgacac atgagagagg tatcctggac ccctgtcctc tggctgcagg    1620
ggccccgggg actgttctgt cccctgcca caaggagcca gtacctcact caggaccccg    1680
accgagcctt cgaaatggac cccgcctggg ctctctcgtt ccacgtccag cccacctctg    1740
cagtggacca cgctccctgg tgcccaccgc ctcctttgca aggggttg ggcagctttt     1800 taatacaggt ggcatgtgct cagccctaac c                                     1831
```

<210> SEQ ID NO 2
<211> LENGTH: 347
<212> TYPE: PRT
<213> ORGANISM: Sus scrofa

<400> SEQUENCE: 2

Met Arg Cys Arg Arg Leu Ala Leu Gly Leu Gly Phe Gly Leu Leu Val
1               5                   10                  15

Gly Val Ala Leu Cys Ser Leu Trp Leu Tyr Val Glu Asn Val Pro Pro
            20                  25                  30

Pro Val Tyr Ile Pro Tyr Tyr Leu Pro Cys Pro Glu Ile Phe Asn Met
        35                  40                  45

Lys Leu Gln Tyr Lys Gly Val Lys Pro Phe Gln Pro Val Ala Gln Ser
50                  55                  60

Gln Tyr Pro Gln Pro Lys Leu Leu Glu Pro Lys Pro Ser Glu Leu Leu
65                  70                  75                  80

Thr Leu Thr Ser Trp Leu Ala Pro Ile Val Ser Glu Gly Thr Phe Asp
                85                  90                  95

Pro Glu Leu Leu His His Ile Tyr Gln Pro Leu Asn Leu Thr Ile Gly
            100                 105                 110

Leu Thr Val Phe Ala Val Gly Lys Tyr Thr Gln Phe Val Gln Arg Phe
        115                 120                 125

Leu Glu Ser Ala Glu Arg Phe Phe Met Gln Gly Tyr Arg Val His Tyr
130                 135                 140

Tyr Ile Phe Thr Ser Asp Pro Gly Ala Val Pro Gly Val Pro Leu Gly
145                 150                 155                 160

Pro Gly Arg Leu Leu Ser Val Ile Ala Ile Arg Arg Pro Ser Arg Trp
                165                 170                 175

Glu Glu Val Ser Thr Arg Arg Met Glu Ala Ile Ser Gln His Ile Ala
            180                 185                 190

Ala Arg Ala His Arg Glu Val Asp Tyr Leu Phe Cys Leu Ser Val Asp
        195                 200                 205

Met Val Phe Arg Asn Pro Trp Gly Pro Glu Thr Leu Gly Asp Leu Val
210                 215                 220

Ala Ala Ile His Pro Gly Tyr Phe Ala Ala Pro Arg Gln Gln Phe Pro
225                 230                 235                 240

Tyr Glu Arg Arg His Val Ser Thr Ala Phe Val Ala Asp Ser Glu Gly
                245                 250                 255

Asp Phe Tyr Tyr Gly Gly Ala Val Phe Gly Gly Arg Val Ala Arg Val
            260                 265                 270

Tyr Glu Phe Thr Gln Gly Cys His Met Gly Ile Leu Ala Asp Lys Ala
        275                 280                 285

Asn Gly Ile Met Ala Ala Trp Gln Glu Glu Ser His Leu Asn Arg Arg
290                 295                 300

Phe Ile Ser His Lys Pro Ser Lys Val Leu Ser Pro Glu Tyr Leu Trp
305                 310                 315                 320

Asp Asp Arg Arg Pro Gln Pro Pro Ser Leu Lys Leu Ile Arg Phe Ser
                325                 330                 335

Thr Leu Asp Lys Asp Thr Asn Trp Leu Arg Ser
            340                 345

<210> SEQ ID NO 3
<211> LENGTH: 43
<212> TYPE: DNA
<213> ORGANISM: Sus scrofa

<400> SEQUENCE: 3

```
tgaattctag ctccgtctgc ctacgctggt ccgaccgcaa ggg                            43
```

<210> SEQ ID NO 4
<211> LENGTH: 1115
<212> TYPE: DNA
<213> ORGANISM: Sus scrofa

<400> SEQUENCE: 4

```
gtgagtctgc agccggtaag gacaatcgcg ctccctccgc tgcgccttgt ccctgccccg          60
cgcccagccg gaggaagagc gccgcgagtc cccagcccgc agtggtagtc gagatgtgtg         120
tcttcggccc caggctcctg ggtgcagatc cccggctggg gcggaccgag ctcggccctg         180
gctgtgagtc ggcagagcgt ccccggcggc ctgggccccg cgggagggag aatctcgcgg         240
agccaactgt cgagggggc cttggaggac gcttcgcccc aaaccgggat gggaaaactg          300
aggtctgtag agggagggag agggattggg aacggccttg cagaggccac cgaatgagca         360
gggccaaagc cccagaactc tggcccgggg atctttgacc tcgagcggat ccccacagag         420
cggccagggg tccggtgctc actgcttact gtgacacaac cctcccggta catcagggag         480
tgcgtattgc gtcttgtccc ctgcaccaag cccctctag ccgaggagga ccccgacgct         540
gtggcggagc ggggacgaga gtgacttgcc caagattatc gccgagcggg tgcgagctga        600
agctcgttcc tgcggtcccc gggagagtcc aggctgccgc tcctggagc aacgccctgc          660
tgccacccct gccctgctc cccgcccggg gggatcgcgg ccgcccctcg ctgcgcagca          720
tcccgcttcc caggcccggc gtgtccccgc tgtgccggct cagagcttaa tttcggcgtc         780
ctcattgtct ccctggggaa tccctctcca agatcagccc aagcgctgtt gccctggtcc         840
ggaggatggc cgcccttcgc tcgccgcagg agtttgggag ggagacctga gagccaaggc         900
aggggaccgg tccttggggc acggctgcag gcttcgggtg agcaatgagc ctctgtcccc         960
gggtcaactt gccagaactg ccccatctgg gcctagggtc cagcaggatg agaagatgac        1020
ctggaatcca cagtccccta gcggggctgc ccggggagg gcggagcagc aaggctgggg        1080
caactatcct ccagataagg agcattcctt tgcag                                   1115
```

<210> SEQ ID NO 5
<211> LENGTH: 191
<212> TYPE: DNA
<213> ORGANISM: Sus scrofa

<400> SEQUENCE: 5

```
gtctcctccg acccccgaag acacaagctc agagcctgac ggcccctgag agaggtgggc          60
ggatccgcca agtcacaccc aggctctgca ggtgctcagg cccagacgct gcacccagag         120
atgcgctgcc gcagactagc cctgggcctg gggttcggcc tgctggtggg cgtggccctc         180
tgctctctgt g                                                              191
```

<210> SEQ ID NO 6
<211> LENGTH: 564
<212> TYPE: DNA
<213> ORGANISM: Sus scrofa

<400> SEQUENCE: 6

```
gtgagcatgc cccgtggagc cctccggccc cacccgactc ctccctctct cagcatctca          60
accccaagc ctgaccctttc actgaactcc cagggctctc atccgcctct cctgacacac         120
```

| | |
|---|---|
| ctgtccttct ggcgccgtaa gagatgaact agtctggact tacgatttt gctttgcact | 180 |
| ggctctttcc tctgcctgga ctattcttct agccatgtta acgaggaact ccagtttatg | 240 |
| ctccaaaatt caccccaatg tgttctttct gcaaagttcc tggcccccccc acccccaccc | 300 |
| cccaccccg cccttgtgt gcagggtctg gcatcaggaa cattcctgcc caggaatga | 360 |
| agggctgcat ggctctataa taactgtgtt gccacagacc gggggctttg ccatccacgg | 420 |
| ttcgccagac ccaaggagtg attggtgggg tgggggtggg ggtcccaggt gcaccctgg | 480 |
| gggccttcat tcccactaac atggaccaag tgggttttca gcctcaggtt caaagtcgag | 540 |
| tcagccagtg ttcttccctc ccag | 564 |

<210> SEQ ID NO 7
<211> LENGTH: 66
<212> TYPE: DNA
<213> ORGANISM: Sus scrofa

<400> SEQUENCE: 7

| | |
|---|---|
| gctgtatgtg gagaacgtgc cgccgccggt ctatatcccc tattacctcc cctgccctga | 60 |
| gatctt | 66 |

<210> SEQ ID NO 8
<211> LENGTH: 2558
<212> TYPE: DNA
<213> ORGANISM: Sus scrofa

<400> SEQUENCE: 8

| | |
|---|---|
| gtgagtatga gacggggaga atgggcgaga tgggaggggt ttttaaggcc gctttgcagg | 60 |
| ttcttacatt ctcagctcag gattctgatc agtgtgatta acagtgagg caatttatga | 120 |
| acggctgcaa atgtggagta aaaactcccc tgtttcagtc ccgagggtg cccttggca | 180 |
| tgttgtgtgg ctctgagcct cacttgctgc acgtgtaaaa gggggcgata gatggtacct | 240 |
| gtgaccgtgc tggtgtcacc cctggcacat aggaggtgcc caggaaagag tgcttttagg | 300 |
| acaagacctt tttgctcaat ttggtgttct gcgtggattc gaggaacaag gtgcccagtc | 360 |
| tctcccacat ggcaaggctg acttttgac agctaagtgt gacacagatc aagtgtgatg | 420 |
| taggttggga cagtcccgag ggtgcatctg gccccctggt cttttgctgt ccatgacagc | 480 |
| agaaggaaag taaagcatgc atcgcaaggg aagttcctgt cgtggctcag tggaaatgga | 540 |
| tctgacgcgt atccatgagg atgcaggttc gatccctggc ctcactcagt gggttaagga | 600 |
| tccggtgttg ccgtgagctg tggtgtagat tgcagacacg actcggatct ggcatggctg | 660 |
| tggctgtggt gtaggccagg gctacagct ccccggaacc tccatatgct gcgggtgcgg | 720 |
| ccctaaaaag acaaccaaaa aaagcatgca tcacagggag ttccctggta gtctagtggt | 780 |
| taggattcag tgcttatgtt ctaaaaaagc agaaaggctg cttgcttttg aaaacagttg | 840 |
| tgaccacaat gttttggat ttttatcctg tttccccgga tttggcctta tttttggcat | 900 |
| ctggtcacca ttattttatt ctaacctggg tctgggcccc ctgaacccct ttcccaccaa | 960 |
| caactttgaa gcatttaggt ggtttccagg tgcccagcgt tctaaattag tttgtaatga | 1020 |
| gcagctctgg acataaagct ttttcccgcc taaagatcct ttcatctggt atgttcctga | 1080 |
| gccaaaggat atggctgggt tctcatccgc ttgctctcca gagggaccag accgtcccac | 1140 |
| actcacgctc atccccgcac ccctacgcac cccgcccca gcagctgcgc cgccgctggg | 1200 |
| ctaggactgg acataccagc tgtcatgaga aacaaaaccc aaaccacctc gctgattgga | 1260 |
| gagatgggaa atgcagtctg gtgtaaatta cgcttctttg atttgttcgg ggccctcatt | 1320 |

-continued

```
tcccccaggc ctttccatga attgaattct gcctccatga acttgccctc tcacctcctt      1380
ccctcccggg cctctttgct gtcctctgtc cccacccttg tatttgctac ctctttttt       1440 tttttttttt tttttttttt ccttttgcca tttcttggcc gctcccccga catatggagg      1500
ttcccaggct aggggtcgaa tcggactgta gccaccagcc tacgccagag ccacagcaac      1560
atgggatcca agcccgtct gcgacctaca ccacagttca cggcaacgcc agatccttaa       1620
cccacgagtg aggacgggga tcgaacccgc cacctcatgg ttcctagtcg gattcatcaa      1680
tcactgagcc acaacgggaa ctccagtatt tgctacatct tgctactttt ttttttcttt     1740
ctagtttgtc tacctcttgg ttcttctgag ggtttgtgtg tgtgtgttgt gatagattga      1800
ggctggagat ttgtgacttt atttaatgtt tagttatgta tgtatttatt ggccacaccc     1860
acggcatatg gaagttccca ggcgaggggt tgaatcggag ccccagctgc cagcctacac     1920
cacagccaca gcaacacagg atccgagctg cgtctgtgac ctataccca gctcacggca      1980 gcgctggatc cttaactcac tgagtgagac cagggatcga acctgcgtcc tcatggatac     2040
tagtcgggtt tgttaccact gagccacgac gggaactccc gaggatagtc tttatataag     2100
gtcagctggt gtcggcgtta ctcacatgtg caaaatacag accttcacag ccgtgcctgg     2160
attgatggcc gtgtaactgg gtcccacaac cacccatcac cgtgggctca ggttaagcaa     2220
ctcgcccagg ctagaaagtg gcagaaccgg gcttactggg cctttgcagc ttctcagtcc     2280
ttctacccaa tgcccaggcc cttcagagc aacatgtttg caagagagac agaaaaagac      2340
tttggagaca agtggtaccg ggtttgaatc acagcaaccc cggacagacc gcctctgtag     2400
aagcccagcc cctgcagtgg gggaggtcta agagagtctg cgtggagcct ggtggggagg     2460
gggtacctgt cccgtggggg ggttcatctt ggcttccctg ccagcatccc ctgccccgg     2520 ccccggcact aatggctgtg tctcgcctct cccaccag                              2558

<210> SEQ ID NO 9
<211> LENGTH: 51
<212> TYPE: DNA
<213> ORGANISM: Sus scrofa

<400> SEQUENCE: 9
caacatgaag ctccagtaca aggggtgaa gccattccag cccgtggcac a                 51

<210> SEQ ID NO 10
<211> LENGTH: 82
<212> TYPE: DNA
<213> ORGANISM: Sus scrofa

<400> SEQUENCE: 10
gtaagcagac tgtcacttcc cccttggtgg ccccccgggg tggggcggc ctccccttac        60 caccggccct tcttggttgc ag                                                82

<210> SEQ ID NO 11
<211> LENGTH: 36
<212> TYPE: DNA
<213> ORGANISM: Sus scrofa

<400> SEQUENCE: 11
gtcccagtac cctcagccca agctgcttga gccaaa                                 36

<210> SEQ ID NO 12
<211> LENGTH: 849
<212> TYPE: DNA
```

<213> ORGANISM: Sus scrofa

<400> SEQUENCE: 12

| | | | | | |
|---|---|---|---|---|---|
| gtaggtgtca | attaggggcg | gggcacagaa | gggagactcc | tggggcggag | gtgggggga | 60 |
| cagagcgctg | attgacaagt | tggggtggtg | gaggggtcag | gtggccttgg | gagccgggtg | 120 |
| gtctggcacc | tgggctccag | tccagccctg | tcactagctg | tgtggcctac | ccaactgctc | 180 |
| tgagcttttc | ctgcgtgggt | ggatagtaat | accccacct | ggagcgttcc | cgctgtggct | 240 |
| cagcaggtga | aggacccagt | gaggtctccg | tgaggatgcg | gctccatcc | ctggcctcgc | 300 |
| tcagtgggtt | aaggacctgg | cgtggctgca | agctgtgcca | caggtcgcat | atgcggctca | 360 |
| gggctggtgt | ggctgtggct | gtggcgtagg | ccgaagctgc | agctccagtt | ctccacccct | 420 |
| ggcccgggaa | cttccatgcg | ccacaggtac | ggccatactg | ataataataa | caataatagt | 480 |
| aataatgata | atacccacct | cataggaggt | tacagggccc | gacgagatgg | tgtttgcaaa | 540 |
| acgcagggca | ctgtgcctgc | gcctacgggg | gtgcccgacc | caccgttaat | aatggtatca | 600 |
| atgactcccg | tttctgaggc | acttggcaga | caccagaaat | gccaggcctt | ccagaccct | 660 |
| ggacgcctgg | tcctcccgac | catgctgaga | agtagctgtt | actacccaca | ctttccacgt | 720 |
| gaggctcctg | gagcccagag | acaggagtga | agctgcccag | ggccacacag | cacaggaggc | 780 |
| aggaccagga | tgagactgag | gctttcacaa | ggggagcgtc | tcagccccca | cggcctcctg | 840 |
| tgctgccag | | | | | | 849 |

<210> SEQ ID NO 13
<211> LENGTH: 135
<212> TYPE: DNA
<213> ORGANISM: Sus scrofa

<400> SEQUENCE: 13

| | | | | | |
|---|---|---|---|---|---|
| gccctcagag | ctcctgacgc | tcacgtcctg | gttggcaccc | atcgtctccg | agggcacctt | 60 |
| cgaccctgag | cttcttcatc | acatctacca | gccactgaac | ctgaccatcg | ggctcacggt | 120 |
| gtttgccgtg | gggaa | | | | | 135 |

<210> SEQ ID NO 14
<211> LENGTH: 1434
<212> TYPE: DNA
<213> ORGANISM: Sus scrofa

<400> SEQUENCE: 14

| | | | | | |
|---|---|---|---|---|---|
| gtgagtcgtg | ggctgggcgt | ggggagggtg | ggtatagatt | ctgaacccca | ggaatgtatg | 60 |
| gtctggggac | agacaggacc | ccgcccaggc | accaggagg | ccctgagcca | ggtgctgagc | 120 |
| aggtgggaag | cacagggtcg | agcgtgatgg | ttgcaggggg | gcttcctgga | ggaagggggt | 180 |
| ctggctctgg | cagcgaagca | ggggagcggc | ccaggtgaga | gatcgatggc | acctttgtca | 240 |
| ggagacacct | tgtcccctta | cccttctgc | ttccctgag | ccgcccaggc | aggtggggag | 300 |
| ggatagaaag | cccccaacc | acctcccata | aatgggggtc | cctggtcggg | ccacacgcag | 360 |
| gtcaagagac | ctgggcagag | cagcccggcc | cccaggagcc | tctctccaac | acgccctccc | 420 |
| ccggcgggcc | cgctgccctc | tgttcagcct | gttctcccct | ctcctccctc | agcctgcctg | 480 |
| gcatttccta | aattaaccgc | cacctggcag | cttccctcgg | ggaccctttc | tgggagtcct | 540 |
| gagagagggg | ccctaatggg | gtcctaatgc | ccaaagcgct | gtccagatgc | tggatggctc | 600 |
| agcgggggtc | aagacccccc | ctcccccgcc | accccagccc | agtcagcacc | cagcatcaca | 660 |
| ccttccctcg | atgcagccac | tcaccgcctg | tgtctataag | atgggtgtgt | ggtccctgcc | 720 |

-continued

```
tcctagggag ttgacgaggc ctgaaggagt cccttaaaac aggagtccct tagaacactg      780
cctggcactt agtaagtgct caataaaagt tagctcagga gttccctggt agcctagcgg      840
ttaaggtcct ggtgttgtca ctgctgtggc gcggattggc tccctggact gagaacttcc     900
acatgttgtg ggtgcgggga aaagaaagt tagctctgga gttcccatcg tgactcagtg      960
gttaatgaat ctgactagca tccatgagga cgcaggttcg atcccaggcc tcgctcagtg     1020
agttaaggat ccgacattgc catgagctgt ggtgtaggtc gcagacacgg ctcggatctg     1080
gcatgactgt ggctgtggcg taggccgtcg gctacagctc tgattggacc cctagcctgg     1140
aaacctccat atgccgtggg tgcagccctc aaaagacaaa caaaaaaggt tagctcagtc     1200
tgtgaatgta agactcctcg agggtcagcc taggacggtc ttaagaggct ggtgctgtga     1260
gtgtgggaat ttgacaagta aggactcgga ggagcctctt gagccgggaa gctgggaggt     1320 ggacccccagc ctggccgacc ctgggctctg tgccccgtgt ggtgccagcc cgtggtgggg    1380
actcaggcag tggccctgct gaggcggtgg tggccactgg gctctcgtcc acag           1434
```

<210> SEQ ID NO 15
<211> LENGTH: 1309
<212> TYPE: DNA
<213> ORGANISM: Sus scrofa

<400> SEQUENCE: 15

```
gtacacccag ttcgtccagc gcttcctgga gtcggccgag cgcttcttca tgcagggcta      60
ccgggtgcac tactacatct ttaccagcga ccccggggcc gttcctgggg tcccgctggg     120
cccgggccgc ctcctcagcg tcatcgccat ccggagaccc tcccgctggg aggaggtctc     180
cacacgccga atggaggcca tcagccagca cattgccgcc agggcgcacc gggaggtcga     240
ctacctcttc tgcctcagcg tggacatggt gttccggaac ccatggggcc ccgagacctt     300
gggggacctg gtggctgcca ttcacccggg ctacttcgcc gcgccccgcc agcagttccc     360
ctacgagcgc cggcatgttt ctaccgcctt cgtggcggac agcgagggg acttctatta     420 tggtggggcg gtcttcgggg gcgggtggc cagggtgtac gagttcaccc agggctgcca     480
catgggcatc ctggcggaca aggccaatgg catcatggcg gcctggcagg aggagagcca     540
cctgaaccgc cgcttcatct cccacaagcc ctccaaggtg ctgtcccccg agtacctctg     600
ggatgaccgc aggccccagc cccccagcct gaagctgatc cgcttttcca cactggacaa     660
agacaccaac tggctgagga gctgacagca cagccggggc tgctgtgcat gcgggggggac    720 cccaagccct gcccccagct cgccccagca gcgcctcctc acccggacgc ctcacttccc    780
aagccttctg tgaaaccagc cctgcgctgc ctacctctca ggctgccagc agactccgag    840
gcctgtgtaa actgtgaagg gctgtgccct tgtgagaaca cacagcctgt gagccagaaa    900
cggtcagacg ggaggagacg gaccagaggt agaagaagac gggacccgca gtcctcaccc    960
agcccacgtg cctttggggt gggcgctgga gggtcagccc tgcccagtgc ctgacgtccc    1020
gcccaccccc ctttttgtgc cgtttgtacc tctgacacat gagagaggta tcctggaccc    1080
ctgtcctctg gctgcagggg ccccggggac tgttctgtcc ccctgccaca aggagccagt    1140
acctcactca ggaccccgac cgagccttcg aaatggaccc cgcctggggct ctctcgttcc    1200 acgtccagcc cacctctgca gtggaccacg ctccctggtg cccaccgcct cctttgcaag    1260
ggggtttggg cagcttttta atacaggtgg catgtgctca gccctaacc                1309
```

<210> SEQ ID NO 16

<211> LENGTH: 8446
<212> TYPE: DNA
<213> ORGANISM: Sus scrofa

<400> SEQUENCE: 16

```
tgaattctag ctccgtctgc ctacgctggt ccgaccgcaa ggggtgagtc tgcagccggt      60
aaggacaatc gcgctccctc cgctgcgcct tgtccctgcc ccgcgcccag ccggaggaag     120
agcgccgcga gtccccagcc cgcagtggta gtcgagatgt gtgtcttcgg ccccaggctc     180
ctgggtgcag atccccggct ggggcggacc gagctcggcc ctggctgtga gtcggcagag     240
cgtccccggc ggcctgggcc ccgcggggag gagaatctcg cggagccaac tgtcgagggg     300
ggccttggag gacgcttcgc cccaaaccgg gatgggaaaa ctgaggtctg tagagggagg     360
gagagggatt gggaacggcc ttgcagaggc caccgaatga gcaggccaa agccccagaa      420
ctctggcccg gggatctttg acctcgagcg gatccccaca gagcggccag gggtccggtg     480
ctcactgctt actgtgacac aaccctcccg gtacatcagg gagtgcgtat tgcgtcttgt     540
cccctgcacc aagccccctc tagccgagga ggaccccgac gctgtggcgg agcggggacg     600
agagtgactt gccaagatt atcgccgagc gggtgcgagc tgaagctcgt tcctgcggtc      660
cccgggagag tccaggctgc cgcctcctgg agcaacgccc tgctgccacc cctgcccctg     720
ctccccgccc gggggatcg cggccgcccc tcgctgcgca gcatcccgct tcccaggccc      780
ggcgtgtccc cgctgtgccg gctcagagct taatttcggc gtcctcattg tctccctggg     840
gaatccctct ccaagatcag cccaagcgct gttgccctgg tccggaggat ggccgccctt     900
cgctcgccgc aggagtttgg gagggagacc tgagagccaa ggcaggggac cggtccttgg     960
ggcacggctg caggcttcgg gtgagcaatg agcctctgtc cccgggtcaa cttgccagaa    1020
ctgccccatc tgggcctagg gtccagcagg atgagaagat gacctggaat ccacagtccc    1080
ctagcggggc tgcccggggg agggcggagc agcaaggctg gggcaactat cctccagata    1140
aggagcattc ctttgcaggt ctcctccgga ccccgaagac acaagctcag agcctgacgg    1200
cccctgagag aggtgggcgg atccgccaag tcacacccag gctctgcagg tgctcaggcc    1260
cagacgctgc acccagagat gcgctgccgc agactagccc tgggcctggg gttcggcctg    1320
ctggtgggcg tggccctctg ctctctgtgg tgagcatgcc ccgtggagcc ctccggcccc    1380
acccgactcc tccctctctc agcatctcaa ccccaagcc tgaccttca ctgaactccc      1440
agggctctca tccgcctctc ctgacacacc tgtccttctg cgccgtaag agatgaacta     1500
gtctggactt acggattttg ctttgcactg gctctttcct ctgcctggac tattcttcta    1560
gccatgttaa cgaggaactc cagtttatgc tccaaaattc accccaatgt gttctttctg    1620
caaagttcct ggccccccca ccccacccc ccaccccgc cccttgtgtg cagggtctgg      1680
catcaggaac attcctgccc caggaatgaa gggctgcatg gctctataat aactgtgttg    1740
ccacagaccg ggggctttgc catccacggt tcgccagacc caaggagtga ttggtggggt    1800
gggggtgggg gtcccaggtg caccctgggg ggccttcatt cccactaaca tggaccaagt    1860
gggttttcag cctcaggttc aaagtcgagt cagccagtgt tcttccctcc caggctgtat    1920
gtggagaacg tgccgccgcc ggtctatatc ccctattacc tccctgccc tgagatcttg     1980
tgagtatgag acgggagaa tgggcagat gggaggggtt tttaaggccg ctttgcaggt      2040
tcttacattc tcagctcagg attctgatca gtgtgattaa acagtgaggc aattatgaa     2100
cggctgcaaa tgtggagtaa aaactcccct gtttcagtcc cgaggggtgc cctttggcat    2160
gttgtgtggc tctgagcctc acttgctgca cgtgtaaaag ggggcgatag atggtacctg    2220
```

```
tgaccgtgct ggtgtcaccc ctggcacata ggaggtgccc aggaaagagt gcttttagga    2280 caagacctttt ttgctcaatt tggtgttctg cgtggattcg aggaacaagg tgcccagtct   2340
ctcccacatg gcaaggctga cttttttgaca gctaagtgtg acacagatca agtgtgatgt   2400
aggttgggac agtcccgagg gtgcatctgg cccctggtc ttttgctgtc catgacagca     2460
gaaggaaagt aaagcatgca tcgcaaggga agttcctgtc gtggctcagt ggaaatggat    2520
ctgacgcgta tccatgagga tgcaggttcg atccctggcc tcactcagtg ggttaaggat    2580
ccggtgttgc cgtgagctgt ggtgtagatt gcagacacga ctcggatctg gcatggctgt    2640
ggctgtggtg taggccaggg gctacagctc cccggaacct ccatatgctg cgggtgcggc    2700
cctaaaaaga caaccaaaaa aagcatgcat cacagggagt tccctggtag tctagtggtt    2760
aggattcagt gcttatgttc taaaaaagca gaaaggctgc ttgcttttga aaacagttgt    2820
gaccacaatg ttttttggatt tttatcctgt ttccccggat ttggccttat ttttggcatc   2880
tggtcaccat tattttattc taacctgggt ctgggcccc tgaacccctt tcccaccaac     2940
aactttgaag catttaggtg gtttccaggt gcccagcgtt ctaaattagt ttgtaatgag    3000
cagctctgga cataaagctt tttcccgcct aaagatcctt tcatctggta tgttcctgag   3060
ccaaaggata tggctgggtt tcatccgct tgctctccag agggaccaga ccgtcccaca     3120
ctcacgctca tccccgcacc cctacgcacc cccgccccag cagctgcgcc gccgctgggc   3180
taggactgga cataccagct gtcatgagaa acaaaaccca aaccacctcg ctgattggag   3240
agatgggaaa tgcagtctgg tgtaaattac gcttctttga tttgttcggg gccctcattt   3300
cccccaggcc tttccatgaa ttgaattctg cctccatgaa cttgccctct cacctccttc   3360 cctcccggc ctctttgctg tcctctgtcc ccacccttgt atttgctacc tctttttttt    3420
tttttttttt tttttttttc cttttgccat tcttggccg ctcccccgac atatggaggt    3480
tcccaggcta ggggtcgaat cggactgtag ccaccagcct acgccagagc cacagcaaca   3540
tgggatccaa gccccgtctg cgacctacac cacagttcac ggcaacgcca gatccttaac   3600
ccacgagtga ggacggggat cgaacccgcc acctcatggt tcctagtcgg attcatcaat   3660
cactgagcca caacgggaac tccagtattt gctacatctt gctactttt tttttctttc    3720 tagtttgtct acctcttggt tcttctgagg gttttgtgtg tgtgttgtg atagattgag     3780 gctggagatt tgtgacttta tttaatgttt agttatgtat gtatttattg ccacaccca    3840 cggcatatgg aagttcccag gcgagggggtt gaatcggagc cccagctgcc agcctacacc  3900
acagccacag caacacagga tccgagctgc gtctgtgacc tatacccccag ctcacggcag  3960 cgctggatcc ttaactcact gagtgagacc agggatcgaa cctgcgtcct catggatact   4020
agtcgggttt gttaccactg agccacgacg ggaactcccg aggatagtct ttatataagg   4080
tcagctggtg tcggcgttac tcacatgtgc aaaatacaga ccttcacagc cgtgcctgga   4140
ttgatggccg tgtaactggg tcccacaacc acccatcacc gtgggctcag gttaagcaac   4200
tcgcccaggc tagaaagtgg cagaaccggg cttactgggc cttttgcagct tctcagtcct  4260 tctacccaat gcccaggccc ttccagagca acatgtttgc aagagagaca gaaaaagact   4320
ttggagacaa gtggtaccgg gtttgaatca cagcaacccc ggacagaccg cctctgtaga   4380
agcccagccc ctgcagtggg ggaggtctaa gagagtctgc gtggagcctg gtggggaggg   4440
ggtacctgtc ccgtgggggg gttcatcttg gcttccctgc cgagcatccc tgcccccggc   4500
cccggcacta atggctgtgt ctcgcctctc ccaccagcaa catgaagctc cagtacaagg   4560
```

```
gggtgaagcc attccagccc gtggcacagt aagcagactg tcacttcccc cttggtggcc    4620
cccgggggtg ggggcggcct ccccttacca ccggcccttc ttggttgcag gtcccagtac    4680
cctcagccca agctgcttga gccaaagtag gtgtcaatta ggggcggggc acagaaggga    4740
gactcctggg gcggaggtgg gggggacaga gcgctgattg acaagttggg gtggtggagg    4800
ggtcaggtgg ccttgggagc cgggtggtct ggcacctggg ctccagtcca gccctgtcac    4860
tagctgtgtg gcctacccaa ctgctctgag cttttcctgc gtgggtggat agtaataccc    4920
ccacctggag cgttcccgct gtggctcagc aggtgaagga cccagtgagg tctccgtgag    4980
gatgcgggct ccatccctgg cctcgctcag tgggttaagg acctggcgtg gctgcaagct    5040
gtgccacagg tcgcatatgc ggctcagggc tggtgtggct gtggctgtgg cgtaggccga    5100
agctgcagct ccagttctcc accccttggcc cgggaacttc catgcgccac aggtacggcc    5160
atactgataa taataacaat aatagtaata atgataatac ccacctcata ggaggttaca    5220
gggcccgacg agatggtgtt tgcaaaacgc agggcactgt gcctgcgccc tacgggtgc    5280 ccgacccacc gttaataatg gtatcaatga ctcccgtttc tgaggcactt ggcagacacc    5340
agaaatgcca ggcctttcca gaccctggac gcctggtcct cccgaccatg ctgagaagta    5400
gctgttacta cccacacttt ccacgtgagg ctcctggagc ccagagacag gagtgaagct    5460
gcccagggcc acacagcaca ggaggcagga ccaggatgag actgaggctt tcacaagggg    5520
agcgtctcag cccccacggc ctcctgtgct gccaggccct cagagctcct gacgctcacg    5580 tcctggtttgg cacccatcgt ctccgagggc accttcgacc ctgagcttct tcatcacatc    5640
taccagccac tgaacctgac catcgggctc acggtgtttg ccgtggggaa gtgagtcgtg    5700
ggctgggcgt ggggagggtg ggtatagatt ctgaaccccca ggaatgtatg gtctggggac    5760
agacaggacc ccgcccaggc caggggagg ccctgagcca ggtgctgagc aggtgggaag    5820
cacagggtcg agcgtgatgg ttgcagggg gcttcctgga ggaagggggt ctggctctgg    5880
cagcgaagca ggggagcggc ccaggtgaga gatcgatggc acctttgtca ggagacacct    5940
tgtcccctta ccccttctgc ttcccctgag ccgcccaggc aggtggggag ggatagaaag    6000 cccccaacc acctcccata aatgggggtc cctggtcggg ccacacgcag gtcaagagac    6060
ctgggcagag cagcccggcc cccaggagcc tctctccaac acgccctccc ccggcgggcc    6120
cgctgccctc tgttcagcct gttctcccct ctcctccctc agcctgcctg gcatttccta    6180
aattaaccgc cacctggcag cttccctcgg ggacccttttc tgggagtcct gagagagggg    6240
ccctaatggg gtcctaatgc ccaaagcgct gtccagatgc tggatggctc agcggggtc    6300 aagaccccc ctccccgcc accccagccc agtcagcacc cagcatcaca ccttccctcg    6360
atgcagccac tcaccgcctg tgtctataag atgggtgtgt ggtccctgcc tcctaggag    6420 ttgacgaggc ctgaaggagt cccttaaaac aggagtccct tagaacactg cctggcactt    6480
agtaagtgct caataaaagt tagctcagga gttccctggt agcctagcgg ttaaggtcct    6540
ggtgttgtca ctgctgtggc gcggattggc tccctggact gagaacttcc acatgttgtg    6600
ggtgcgggga aaagaaagt tagctctgga gttcccatcg tgactcagtg gttaatgaat    6660
ctgactagca tccatgagga cgcaggttcg atcccaggcc tcgctcagtg agttaaggat    6720
ccgacattgc catgagctgt ggtgtaggtc gcagacacgg ctcggatctg gcatgactgt    6780
ggctgtggcg taggccgtcg gctacagctc tgattggacc cctagcctgg aaacctccat    6840
atgccgtggg tgcagccctc aaaagacaaa caaaaaaggt tagctcagtc tgtgaatgta    6900
agactcctcg agggtcagcc taggacggtc ttaagaggct ggtgctgtga gtgtgggaat    6960
```

```
ttgacaagta aggactcgga ggagcctctt gagccgggaa gctggaggt ggaccccagc    7020 ctggccgacc ctgggctctg tgccccgtgt ggtgccagcc cgtggtgggg actcaggcag    7080
tggccctgct gaggcggtgg tggccactgg gctctcgtcc acaggtacac ccagttcgtc    7140
cagcgcttcc tggagtcggc cgagcgcttc ttcatgcagg gctaccgggt gcactactac    7200
atctttacca cgcaccccgg ggccgttcct ggggtcccgc tgggcccggg ccgcctcctc    7260
agcgtcatcg ccatccggag accctcccgc tgggaggagg tctccacacg ccggatggag    7320
gccatcagcc agcacattgc cgccagggcg caccgggagg tcgactacct cttctgcctc    7380
agcgtggaca tggtgttccg gaacccatgg ggccccgaga ccttggggga cctggtggct    7440
gccattcacc cgggctactt cgccgcgccc cgccagcagt tcccctacga cgccggcat    7500 gtttctaccg ccttcgtggc ggacagcgag ggggacttct attatggtgg ggcggtcttc    7560 gggggcggg tggccaggt gtacgagttc acccagggct gccacatggg catcctggcg    7620
gacaaggcca atggcatcat ggcggcctgg caggaggaga gccacctgaa ccgccgcttc    7680
atctcccaca gccctccaa ggtgctgtcc ccgagtacc tctgggatga ccgcaggccc    7740 cagccccca gcctgaagct gatccgcttt tccacactgg acaaagacac caactggctg    7800
aggagctgac agcacagccg gggctgctgt gcatgcgggg ggaccccaag ccctgccccc    7860
agctcgcccc agcagcgcct cctcacccgg acgcctcact tcccaagcct tctgtgaaac    7920
cagccctgcg ctgcctacct tcaggctgc cagcagactc cgaggcctgt gtaaactgtg    7980
aagggctgtg cccttgtgag aacacacagc ctgtgagcca gaaacggtca gacgggagga    8040
gacggaccag aggtagaaga agacgggacc cgcagtcctc acccagccca cgtgcctttg    8100
gggtgggcgc tggagggtca gccctgccca gtgcctgacg tcccgcccac cccccttttg    8160
tggccgtttg tacctctgac acatgagaga ggtatcctgg accctgtcc tctggctgca    8220 ggggccccgg ggactgttct gtccccctgc cacaaggagc cagtacctca ctcaggaccc    8280
cgaccgagcc ttcgaaatgg accccgcctg gctctctcg ttccacgtcc agcccacctc    8340
tgcagtggac cacgctccct ggtgcccacc gcctcctttg caaggggtt tgggcagctt    8400 tttaatacag gtggcatgtg ctcagcccta accagagttt ctgcag              8446

<210> SEQ ID NO 17
<211> LENGTH: 7124
<212> TYPE: DNA
<213> ORGANISM: Sus scrofa

<400> SEQUENCE: 17
tgaattctag ctccgtctgc ctacgctggt ccgaccgcaa ggggtgagtc tgcagccggt      60
aaggacaatc gcgctccctc cgctgcgcct tgtccctgcc ccgcgcccag ccggaggaag     120
agcgccgcga gtccccagcc cgcagtggta gtcgagatgt gtgtcttcgg ccccaggctc     180
ctgggtgcag atccccggct ggggcggacc gagctcggcc ctggctgtga gtcggcagag     240
cgtccccggc ggcctgggcc ccgcggggag gagaatctcg cggagccaac tgtcgagggg     300
ggccttggag gacgcttcgc cccaaaccgg gatgggaaaa ctgaggtctg tagagggagg     360
gagagggatt gggaacggcc ttgcagaggc caccgaatga gcagggccaa agccccagaa     420
ctctggcccg gggatctttg acctcgagcg gatccccaca gagcggccag gggtccggtg     480
ctcactgctt actgtgacac aaccctcccg gtacatcagg gagtgcgtat tgcgtcttgt     540
cccctgcacc aagcccctc tagccgagga ggaccccgac gctgtggcgg agcggggacg     600
```

```
agagtgactt gcccaagatt atcgccgagc gggtgcgagc tgaagctcgt tcctgcggtc    660
cccgggagag tccaggctgc cgcctcctgg agcaacgccc tgctgccacc cctgcccctg    720
ctccccgccc gggggatcg cggccgcccc tcgctgcgca gcatcccgct tcccaggccc    780
ggcgtgtccc cgctgtgccg gctcagagct taatttcggc gtcctcattg tctccctggg    840
gaatccctct ccaagatcag cccaagcgct gttgccctgg tccggaggat ggccgccctt    900
cgctcgccgc aggagtttgg gagggagacc tgagagccaa gcaggggac cggtccttgg    960 ggcacggctg caggcttcgg gtgagcaatg agcctctgtc cccgggtcaa cttgccagaa   1020
ctgccccatc tgggcctagg gtccagcagg atgagaagat gacctggaat ccacagtccc   1080
ctagcggggc tgcccggggg agggcggagc agcaaggctg ggcaactat cctccagata   1140 aggagcattc ctttgcaggt ctcctccgga ccccgaagac acaagctcag agcctgacgg   1200
cccctgagag aggtgggcgg atccgccaag tcacacccag gctctgcagg tgctcaggcc   1260
cagacgctgc acccagagat gcgctgccgc agactagccc tgggcctggg gttcggcctg   1320
ctggtgggcg tggccctctg ctctctgtgg tgagcatgcc ccgtggagcc ctccggcccc   1380
acccgactcc tccctctctc agcatctcaa cccccaagcc tgacccttca ctgaactccc   1440
agggctctca tccgcctctc ctgacacacc tgtccttctg gcgccgtaag agatgaacta   1500
gtctggactt acggattttg ctttgcactg gctctttcct ctgcctggac tattcttcta   1560
gccatgttaa cgaggaactc cagtttatgc tccaaaattc accccaatgt gttctttctg   1620
caaagttcct ggcccccccca ccccaccccc cacccccgc ccttgtgtg cagggtctgg   1680 catcaggaac attcctgccc caggaatgaa gggctgcatg gctctataat aactgtgttg   1740
ccacagaccg ggggctttgc catccacggt tcgccagacc caaggagtga ttggtggggt   1800
gggggtgggg gtcccaggtg caccctggg ggccttcatt cccactaaca tggaccaagt   1860
gggttttcag cctcaggttc aaagtcgagt cagccagtgt tcttccctcc caggctgtat   1920
gtggagaacg tgccgccgcc ggtctatatc ccctattacc tcccctgccc tgagatcttg   1980
tgagtatgag acggggagaa tgggcgagat gggaggggtt tttaaggccg ctttgcaggt   2040
tcttacattc tcagctcagg attctgatca gtgtgattaa acagtgaggc aatttatgaa   2100
cggctgcaaa tgtggagtaa aaactcccct gtttcagtcc cgaggggtgc cctttggcat   2160
gttgtgtggc tctgagcctc acttgctgca cgtgtaaaag ggggcgatag atggtacctg   2220
tgaccgtgct ggtgtcaccc ctggcacata ggaggtgccc aggaaagagt gcttttagga   2280
caagaccttt ttgctcaatt tggtgttctg cgtggattcg aggaacaagg tgcccagtct   2340
ctcccacatg gcaaggctga ctttttgaca gctaagtgtg acacagatca agtgtgatgt   2400
aggttgggac agtcccgagg gtgcatctgg cccccctggtc ttttgctgtc catgacagca   2460
gaaggaaagt aaagcatgca tcgcaaggga agttcctgtc gtggctcagt ggaaatggat   2520
ctgacgcgta tccatgagga tgcaggttcg atccctggcc tcactcagtg ggttaaggat   2580
ccggtgttgc cgtgagctgt ggtgtagatt gcagacacga ctcggatctg catggctgt   2640 ggctgtggtg taggccaggg gctacagctc cccggaacct ccatatgctg cgggtgcggc   2700
cctaaaaaga caaccaaaaa aagcatgcat cacagggagt ccctggtag tctagtggtt   2760 aggattcagt gcttatgttc taaaaaagca gaaaggctgc ttgcttttga aaacagttgt   2820
gaccacaatg ttttttggatt tttatcctgt ttccccggat ttggccttat ttttggcatc   2880
tggtcaccat tatttattc taacctgggt ctgggccccc tgaacccctt tcccaccaac   2940
aactttgaag catttaggtg gtttccaggt gcccagcgtt ctaaattagt ttgtaatgag   3000
```

```
cagctctgga cataaagctt tttcccgcct aaagatcctt tcatctggta tgttcctgag    3060
ccaaaggata tggctgggtt ctcatccgct tgctctccag agggaccaga ccgtcccaca    3120
ctcacgctca tccccgcacc cctacgcacc cccgcccag cagctgcgcc gccgctgggc     3180
taggactgga cataccagct gtcatgagaa acaaaaccca aaccacctcg ctgattggag    3240
agatgggaaa tgcagtctgg tgtaaattac gcttctttga tttgttcggg gccctcattt    3300
ccccccaggcc tttccatgaa ttgaattctg cctccatgaa cttgccctct cacctccttc   3360
cctcccgggc ctctttgctg tcctctgtcc ccacccttgt atttgctacc tcttttttt    3420
tttttttttt ttttttttttc cttttgccat tcttggccg ctcccccgac atatggaggt   3480
tcccaggcta ggggtcgaat cggactgtag ccaccagcct acgccagagc cacagcaaca   3540
tgggatccaa gccccgtctg cgacctacac acagttcac ggcaacgcca gatccttaac   3600
ccacgagtga ggacggggat cgaacccgcc acctcatggt tcctagtcgg attcatcaat   3660
cactgagcca caacgggaac tccagtattt gctacatctt gctactttt tttttctttc    3720
tagtttgtct acctcttggt tcttctgagg gttttgtgtgt gtgtgttgtg atagattgag   3780
gctggagatt tgtgactttta tttaatgttt agttatgtat gtatttattg gccacaccca   3840
cggcatatgg aagttcccag gcgagggggtt gaatcggagc cccagctgcc agcctacacc   3900
acagccacag caacacagga tccgagctgc gtctgtgacc tatatccccag ctcacggcag   3960
cgctggatcc ttaactcact gagtgagacc agggatcgaa cctgcgtcct catggatact    4020
agtcgggttt gttaccactg agccacgacg ggaactcccg aggatagtct ttatataagg   4080
tcagctggtg tcggcgttac tcacatgtgc aaaatacaga ccttcacagc cgtgcctgga   4140
ttgatggccg tgtaactggg tcccacaacc acccatcacc gtgggctcag gttaagcaac   4200
tcgcccaggc tagaaagtgg cagaaccggg cttactgggc cttttgcagct tctcagtcct   4260
tctacccaat gcccaggccc ttccagagca acatgtttgc aagagagaca gaaaaagact   4320
ttggagacaa gtggtaccgg gtttgaatca cagcaacccc ggacagaccg cctctgtaga   4380
agcccagccc ctgcagtggg ggaggtctaa gagagtctgc gtggagcctg gtggggaggg   4440
ggtacctgtc ccgtgggggg gttcatcttg gcttccctgc cgagcatccc tgcccccggc   4500
cccggcacta atggctgtgt ctcgcctctc ccaccagcaa catgaagctc cagtacaagg   4560
gggtgaagcc attccagccc gtggcacagt aagcagactg tcacttcccc cttggtggcc   4620
cccgggggtg ggggcggcct ccccttacca ccggcccttc ttggttgcag gtcccagtac   4680
cctcagccca agctgcttga gccaaagtag gtgtcaatta ggggcggggc acagaaggga   4740
gactcctggg gcggaggtgg gggggacaga gcgctgattg acaagttggg gtggtggagg   4800
ggtcaggtgg ccttgggagc cgggtggtct ggcacctggg ctccagtcca gccctgtcac   4860
tagctgtgtg gcctacccaa ctgctctgag ctttttcctgc gtgggtggat agtaatacccc 4920
ccacctggag cgttcccgct gtggctcagc aggtgaagga cccagtgagg tctccgtgag   4980
gatgcgggct ccatccctgg cctcgctcag tgggttaagg acctggcgtg gctgcaagct   5040
gtgccacagg tcgcatatgc ggctcagggc tggtgtggct gtggctgtgg cgtaggccga   5100
agctgcagct ccagttctcc accccctggcc cgggaacttc catgcgccac aggtacggcc   5160
atactgataa taataacaat aatagtaata atgataatac ccacctcata ggaggttaca   5220
gggcccgacg agatggtgtt tgcaaaacgc agggcactgt gcctgcgccc tacggggtgc   5280
ccgacccacc gttaataatg gtatcaatga ctcccgtttc tgaggcactt ggcagacacc   5340
```

| | |
|---|---:|
| agaaatgcca ggcctttcca gaccctggac gcctggtcct cccgaccatg ctgagaagta | 5400 |
| gctgttacta cccacacttt ccacgtgagg ctcctggagc ccagagacag gagtgaagct | 5460 |
| gcccagggcc acacagcaca ggaggcagga ccaggatgag actgaggctt tcacaagggg | 5520 |
| agcgtctcag cccccacggc ctcctgtgct gccaggccct cagagctcct gacgctcacg | 5580 |
| tcctggttgg cacccatcgt ctccgagggc accttcgacc ctgagcttct tcatcacatc | 5640 |
| taccagccac tgaacctgac catcgggctc acggtgtttg ccgtggggaa gtgagtcgtg | 5700 |
| ggctgggcgt ggggagggtg ggtatagatt ctgaacccca ggaatgtatg gtctggggac | 5760 |
| agacaggacc ccgcccaggc accagggagg ccctgagcca ggtgctgagc aggtgggaag | 5820 |
| cacagggtcg agcgtgatgg ttgcagggggg gcttcctgga ggaaggggggt ctggctctgg | 5880 |
| cagcgaagca ggggagcggc ccaggtgaga gatcgatgcg acctttgtca ggagacacct | 5940 |
| tgtcccctta ccccttctgc ttcccctgag ccgcccaggc aggtggggag ggatagaaag | 6000 |
| ccccccaacc acctcccata aatgggggtc cctggtcggg ccacacgcag gtcaagagac | 6060 |
| ctgggcagag cagcccggcc ccaggagcc tctctccaac acgccctccc ccggcgggcc | 6120 |
| cgctgccctc tgttcagcct gttctcccct ctcctccctc agcctgcctg gcatttccta | 6180 |
| aattaaccgc cacctggcag cttccctcgg ggacccttc tgggagtcct gagagagggg | 6240 |
| ccctaatggg gtcctaatgc ccaaagcgct gtccagatgc tggatggctc agcggggtc | 6300 |
| aagaccccc ctccccgcc accccagccc agtcagcacc cagcatcaca ccttccctcg | 6360 |
| atgcagccac tcaccgcctg tgtctataag atgggtgtgt ggtccctgcc tcctagggag | 6420 |
| ttgacgaggc ctgaaggagt cccttaaaac aggagtccct tagaacactg cctggcactt | 6480 |
| agtaagtgct caataaaagt tagctcagga gttccctggt agcctagcgg ttaaggtcct | 6540 |
| ggtgttgtca ctgctgtggc gcggattggc tccctggact gagaacttcc acatgttgtg | 6600 |
| ggtgcgggga aaaagaaagt tagctctgga gttcccatcg tgactcagtg gttaatgaat | 6660 |
| ctgactagca tccatgagga cgcaggttcg atcccaggcc tcgctcagtg agttaaggat | 6720 |
| ccgacattgc catgagctgt ggtgtaggtc gcagacacgg ctcggatctg gcatgactgt | 6780 |
| ggctgtggcg taggccgtcg gctacagctc tgattggacc cctagcctgg aaacctccat | 6840 |
| atgccgtggg tgcagccctc aaaagacaaa caaaaaaggt tagctcagtc tgtgaatgta | 6900 |
| agactcctcg agggtcagcc taggacggtc ttaagaggct ggtgctgtga gtgtgggaat | 6960 |
| ttgacaagta aggactcgga ggagcctctt gagccgggaa gctgggaggt ggaccccagc | 7020 |
| ctggccgacc ctgggctctg tgccccgtgt ggtgccagcc cgtggtgggg actcaggcag | 7080 |
| tggccctgct gaggcggtgg tggccactgg gctctcgtcc acag | 7124 |

<210> SEQ ID NO 18
<211> LENGTH: 4537
<212> TYPE: DNA
<213> ORGANISM: Sus scrofa

<400> SEQUENCE: 18

| | |
|---|---:|
| tgaattctag ctccgtctgc ctacgctggt ccgaccgcaa ggggtgagtc tgcagccggt | 60 |
| aaggacaatc gcgctccctc cgctgcgcct tgtccctgcc ccgcgcccag ccggaggaag | 120 |
| agcgccgcga gtccccagcc cgcagtggta gtcgagatgt gtgtcttcgg ccccaggctc | 180 |
| ctgggtgcag atccccggct ggggcggacc gagctcggcc ctggctgtga gtcggcagag | 240 |
| cgtcccggc ggcctgggcc ccgcgggagg gagaatctcg cggagccaac tgtcgagggg | 300 |
| ggccttggag gacgcttcgc cccaaaccgg gatgggaaaa ctgaggtctg tagagggagg | 360 |

```
gagagggatt gggaacggcc ttgcagaggc caccgaatga gcagggccaa agccccagaa    420
ctctggcccg gggatctttg acctcgagcg gatccccaca gagcggccag gggtccggtg    480
ctcactgctt actgtgacac aaccctcccg gtacatcagg gagtgcgtat tgcgtcttgt    540
cccctgcacc aagcccctc tagccgagga ggaccccgac gctgtggcgg agcggggacg     600
agagtgactt gcccaagatt atcgccgagc gggtgcgagc tgaagctcgt tcctgcggtc    660
cccgggagag tccaggctgc cgcctcctgg agcaacgccc tgctgccacc cctgcccctg    720
ctccccgccc gggggatcg cggccgcccc tcgctgcgca gcatcccgct tcccaggccc     780
ggcgtgtccc cgctgtgccg gctcagagct taatttcggc gtcctcattg tctccctggg    840
gaatccctct ccaagatcag cccaagcgct gttgccctgg tccggaggat ggccgccctt    900
cgctcgccgc aggagtttgg gagggagacc tgagagccaa gcaggggac cggtccttgg     960
ggcacggctg caggcttcgg gtgagcaatg agcctctgtc cccgggtcaa cttgccagaa   1020
ctgccccatc tgggcctagg gtccagcagg atgagaagat gacctggaat ccacagtccc   1080
ctagcggggc tgcccggggg agggcggagc agcaaggctg gggcaactat cctccagata   1140
aggagcattc ctttgcaggt ctcctccgga ccccgaagac acaagctcag agcctgacgg   1200
cccctgagag aggtgggcgg atccgccaag tcacacccag gctctgcagg tgctcaggcc   1260
cagacgctgc acccagagat gcgctgccgc agactagccc tgggcctggg gttcggcctg   1320
ctggtgggcg tggccctctg ctctctgtgg tgagcatgcc ccgtggagcc ctccggcccc   1380
acccgactcc tccctctctc agcatctcaa ccccaagcc tgacccttca ctgaactccc    1440
agggctctca tccgcctctc ctgacacacc tgtccttctg gcgccgtaag agatgaacta   1500
gtctggactt acggattttg ctttgcactg gctctttcct ctgcctggac tattcttcta   1560
gccatgttaa cgaggaactc cagtttatgc tccaaaattc ccccaatgt gttctttctg    1620
caaagttcct ggcccccca ccccacccc cacccccgc ccttgtgtg cagggtctgg      1680
catcaggaac attcctgccc caggaatgaa gggctgcatg gctctataat aactgtgttg   1740
ccacagaccg ggggctttgc catccacggt tcgccagacc caaggagtga ttggtggggt   1800
gggggtgggg gtcccaggtg caccccctggg ggccttcatt cccactaaca tggaccaagt  1860
gggttttcag cctcaggttc aaagtcgagt cagccagtgt tcttccctcc caggctgtat   1920
gtggagaacg tgccgccgcc ggtctatatc ccctattacc tccccctgccc tgagatcttg   1980
tgagtatgag acggggagaa tgggcgagat gggaggggtt tttaaggccg ctttgcaggt   2040
tcttacattc tcagctcagg attctgatca gtgtgattaa acagtgaggc aatttatgaa   2100
cggctgcaaa tgtggagtaa aaactcccct gtttcagtcc cgaggggtgc cctttggcat   2160
gttgtgtggc tctgagcctc acttgctgca cgtgtaaaag ggggcgatag atggtacctg   2220
tgaccgtgct ggtgtcaccc ctggcacata ggaggtgccc aggaaagagt gcttttagga   2280
caagaccttt ttgctcaatt tggtgttctg cgtggattcg aggaacaagg tgcccagtct   2340
ctcccacatg gcaaggctga cttttttgaca gctaagtgtg acacagatca agtgtgatgt   2400
aggttgggac agtcccgagg gtgcatctgg cccccctggtc ttttgctgtc catgacagca   2460
gaaggaaagt aaagcatgca tcgcaaggga agttcctgtc gtggctcagt ggaaatggat   2520
ctgacgcgta tccatgagga tgcaggttcg atccctggcc tcactcagtg ggttaaggat   2580
ccggtgttgc cgtgagctgt ggtgtagatt gcagacacga ctcggatctg gcatggctgt   2640
ggctgtggtg taggccaggg gctacagctc cccggaacct ccatatgctg cgggtgcggc   2700
```

```
cctaaaaaga caaccaaaaa aagcatgcat cacagggagt tccctggtag tctagtggtt      2760
aggattcagt gcttatgttc taaaaaagca gaaaggctgc ttgcttttga aaacagttgt      2820
gaccacaatg tttttggatt tttatcctgt ttccccggat ttggccttat ttttggcatc      2880
tggtcaccat tattttattc taacctgggt ctgggccccc tgaacccctt tcccaccaac      2940
aactttgaag catttaggtg gtttccaggt gcccagcgtt ctaaattagt ttgtaatgag      3000
cagctctgga cataaagctt ttcccgcct aaagatcctt tcatctggta tgttcctgag       3060
ccaaaggata tggctgggtt ctcatccgct tgctctccag agggaccaga ccgtcccaca      3120
ctcacgctca tccccgcacc cctacgcacc cccgccccag cagctgcgcc gccgctgggc      3180
taggactgga cataccagct gtcatgagaa acaaaaccca aaccacctcg ctgattggag      3240
agatgggaaa tgcagtctgg tgtaaattac gcttctttga tttgttcggg gccctcattt      3300
cccccaggcc tttccatgaa ttgaattctg cctccatgaa cttgccctct cacctccttc      3360
cctcccgggc tctcttgctg tcctctgtcc ccacccttgt atttgctacc tcttttttt     3420 tttttttttt ttttttttc cttttgccat ttcttggccg ctcccccgac atatggaggt      3480
tcccaggcta ggggtcgaat cggactgtag ccaccagcct acgccagagc cacagcaaca     3540
tgggatccaa gccccgtctg cgacctacac cacagttcac ggcaacgcca gatccttaac     3600
ccacgagtga ggacggggat cgaacccgcc acctcatggt tcctagtcgg attcatcaat     3660
cactgagcca acgggaac tccagtatt gctacatctt gctactttt ttttctttc         3720 tagtttgtct acctcttggt tcttctgagg gttttgtgtgt gtgtgttgtg atagattgag    3780
gctggagatt tgtgactta tttaatgttt agttatgtat gtatttattg gccacaccca     3840
cggcatatgg aagttcccag gcgagggggtt gaatcggagc cccagctgcc agcctacacc    3900
acagccacag caacacagga tccgagctgc gtctgtgacc tatacccag ctcacggcag     3960 cgctggatcc ttaactcact gagtgagacc agggatcgaa cctgcgtcct catggatact    4020
agtcgggttt gttaccactg agccacgacg ggaactcccg aggatagtct ttatataagg    4080
tcagctggtg tcggcgttac tcacatgtgc aaaatacaga ccttcacagc cgtgcctgga   4140
ttgatggccg tgtaactggg tcccacaacc acccatcacc gtgggctcag gttaagcaac   4200
tcgcccaggc tagaaagtgg cagaaccggg cttactgggc cttttgcagct tctcagtcct  4260 tctacccaat gcccaggccc ttccagagca acatgtttgc aagagagaca gaaaaagact   4320
ttggagacaa gtggtaccgg gtttgaatca cagcaaccc ggacagaccg cctctgtaga   4380
agcccagccc ctgcagtggg ggaggtctaa gagagtctgc gtggagcctg gtggggaggg   4440
ggtacctgtc ccgtggggggg gttcatcttg gcttccctgc cgagcatccc tgcccccggc   4500
cccggcacta atggctgtgt ctcgcctctc ccaccag                             4537
```

<210> SEQ ID NO 19
<211> LENGTH: 28
<212> TYPE: DNA
<213> ORGANISM: Primer

<400> SEQUENCE: 19

```
ctcccctgcc cagagatctt caacatga                                         28
```

<210> SEQ ID NO 20
<211> LENGTH: 29
<212> TYPE: DNA
<213> ORGANISM: Primer

<400> SEQUENCE: 20

-continued

```
cccatcgtct ccgagggaac cttcaaccc                                29

<210> SEQ ID NO 21
<211> LENGTH: 28
<212> TYPE: DNA
<213> ORGANISM: Primer

<400> SEQUENCE: 21
gaagtgacgg ttcaggtggc tttcctcc                                 28

<210> SEQ ID NO 22
<211> LENGTH: 26
<212> TYPE: DNA
<213> ORGANISM: Primer

<400> SEQUENCE: 22
tcccagaggt actcggggga cagcac                                   26
```

PORCINE FORSSMAN SYNTHETASE PROTEIN, CDNA, GENOMIC ORGANIZATION, AND REGULATORY REGION

This patent application claims priority to U.S. provisional application No. 60/568,922 filed May 7, 2004, which is herein incorporated by reference in its entirety.

FIELD OF THE INVENTION

The present invention provides porcine Forssman synthetase (FSM synthase) (Globoside α-N-acetylgalactosaminyltransferase) protein, cDNA, and genomic DNA sequence. Furthermore, the present invention includes porcine animals, tissue and organs as well as cells and cell lines derived from such animals, tissue and organs, which lack expression of functional FSM synthetase. Such animals, tissues, organs and cells can be used in research and medical therapy, including xenotransplantation. In addition, methods are provided to prepare organs, tissues, and cells lacking the porcine FSM synthetase gene for use in xenotransplantation.

BACKGROUND OF THE INVENTION

The unavailability of acceptable human donor organs, the low rate of long term success due to host versus graft rejection, and the serious risks of infection and cancer are serious challenges now facing the field of tissue and organ transplantation. Because the demand for acceptable organs exceeds the supply, many people die each year while waiting for organs to become available. To help meet this demand, research has been focused on developing alternatives to allogenic transplantation. For example, dialysis has been available to patients suffering from kidney failure, artificial heart models have been tested, and other mechanical systems have been developed to assist or replace failing organs. Such approaches, however, are quite expensive, and the need for frequent and periodic access to such machines greatly limits the freedom and quality of life of patients undergoing such therapy.

Xenograft transplantation represents a potentially attractive alternative to artificial organs for human transplantation. The potential pool of nonhuman organs is virtually limitless, and successful xenograft transplantation would not render the patient virtually tethered to machines as is the case with artificial organ technology. Pigs are considered the most likely source of xenograft organs. The supply of pigs is plentiful, breeding programs are well established, and their size and physiology are compatible with humans. Therefore, xenotransplantation with pig organs offers a solution to the shortage of organs available for clinical transplantation.

Host rejection of such cross-species tissue, however, remains a major concern in this area, and the success of xenotransplantion depends on avoiding rejection of the foreign species organ. The immunological barriers to xenotransplantation have been, and remain, formidable. The first immunological hurdle is "hyperacute rejection" (HAR). HAR can be defined by the ubiquitous presence of high titers of pre-formed natural antibodies binding to the foreign tissue. The binding of these natural antibodies to target epitopes on the donor organ endothelium is believed to be the initiating event in HAR. This binding, within minutes of perfusion of the donor organ with the recipient blood, is followed by complement activation, platelet and fibrin deposition, and ultimately by interstitial edema and hemorrhage in the donor organ, all of which cause failure of the organ in the recipient (Strahan et al. (1996) Frontiers in Bioscience 1, e34-41).

Glycoproteins and glycolipids are present on virtually all mammalian cell membranes, and play important roles in the structure and physiology of the cell (Kolter T and Sandhoff K, (1998) Brain Pathol 8:79-100). Glycolipids that contain the Forssman antigen (pentaglycosylceramide) (GalNAcα(1,3) GalNAcβ(1,3)Galα(1,4)Galβ(1,4)Galβ(1,1)Cer) are found on the cells of many mammals, including pigs (Copper et al. (1993) Transplant Immunol 1:198-205). This antigen is chemically related to the human A, B, and 0 blood antigens. However, the glycolipids of Old World monkeys, apes, and humans do not normally contain FSM antigens, although certain malignancies in humans have been shown to express this particular antigen (Hansson G C et al. (1984) FEBS Lett. 170:15-18; —Stromberg N et al. (1988) FEBS Lett. 232:193-198). Although humans do express the FSM antigen precursor—globotriaosylceramide (Xu H et. al. (1999) 274(41): 29390-29398), it is not converted to the FSM antigen. In other mammals, the modification of this FSM antigen precursor with the addition of an N-acetylgalactosamine via the FSM synthetase enzyme creates the Forssman antigen.

Because humans lack the FSM antigen, exposure to discordant cells, tissues or organs containing the antigen can lead to the development of anti-FSM antigen antibodies. This antibody development can ultimately play a role in the rejection of FSM antigen containing xenografts. Because pig cells express FSM antigen (see, for example, Cooper M A. et al. (1993) Transplant Immunol 1:198-205), the use of pig organs in a xenotransplant strategy can be compromised due to the potential of organ rejection induced by the FSM antigen.

To date, much research has focused on the reduction of immunogenic cell surface carbohydrate epitopes expressed in discordant xenograft organs. For example, the alpha galactosyltransferase (α(1,3)GT) enzyme is one of the molecules that mediates the formation of Galα(1,3)Gal moieties, a highly immunogenic molecule in humans. Research has focused on the modulation of this particular enzyme to reduce or eliminate the expression of Galα(1,3)Gal moieties on the cell surface. The elimination of the α(1,3)GT gene from porcine has long been considered one of the most significant hurdles to accomplishing xenotransplantation from pigs to humans. Recently, this has been accomplished (Dai et al., Science January 17; 299(5605): 411-4 (2003)).

Haslam D B et al. (Biochemistry 93:10697-10702 (1996) describes a cDNA sequence that encodes for canine Forssman synthetase isolated from a canine kidney cDNA library.

Xu H et al. (J. Bio. Chem. 274(41):29390-29398 (1999) describe a cDNA sequence that encodes for human Forssman synthetase isolated from human brain and kidney cDNA libraries.

U.S. Pat. No. 6,607,723 to the Alberta Research Council and Integris Baptist Medical Center describes removing preformed antibodies to various identified carbohydrate xenoantigens, including the FSM antigen, from a recipient's circulation prior to transplantation by extracorporeal perfusion of the recipient's blood over a biocompatible solid support to which the xenoantigens are bound and/or parenterally administering a xenoantibody-inhibiting amount of an identified xenoantigen to the recipient shortly before graft revascularization.

U.S. Pat. No. 6,331,658 to Integris Baptist Medical Center and Oklahoma Medical Research Foundation describes methods for making a non-human tissue or organ less susceptible to antibody-mediated rejection by human serum by genetically engineering the genome of a non-human mammal to stably include a nucleotide sequence encoding a sialyltransferase or a fucosyltransferase in operable linkage with a promoter, wherein the mammal lacks, or has reduced amounts of, on the surface of its organ cells, carbohydrate structures including Forssman saccharides.

U.S. Patent Publication No. 2003/0153044 to Liljedahl et al. discloses a partial cDNA sequence, including portions of exons 4, 5, 6, and 7, of the porcine Forssman synthetase gene.

It is an object of the present invention to provide genomic and regulatory sequences of the porcine Forssman synthetase gene.

It is an additional object of the present invention to provide cDNA, as well as novel variants, of the porcine Forssman synthetase gene.

It is another object of this invention to provide novel nucleic acid and amino acid sequences that encode the Forssman synthetase protein.

It is yet a further object of the present invention to provide cells, tissues and/or organs deficient in the porcine FSM synthetase gene.

It is another object of the present invention to generate animals, particularly pigs, lacking a functional porcine FSM synthetase gene.

SUMMARY OF THE INVENTION

The present invention provides porcine Forssman synthetase (FSM synthase) (Globoside α-N-acetylgalactosaminyltransferase) protein, cDNA, and genomic DNA regulatory sequence. Furthermore, the present invention includes porcine animals, tissue and organs as well as cells and cell lines derived from such animals, tissue and organs, which lack expression of functional FSM synthetase. Such animals, tissues, organs and cells can be used in research and in medical therapy, including in xenotransplantation. In addition, methods are provided to prepare organs, tissues, and cells lacking the porcine FSM synthetase gene for use in xenotransplantation.

One embodiment of the present invention provides the full length nucleic acid (Table 1, Seq. ID No. 1) and peptide (Table 2, Seq. ID No. 2) sequences representing cDNA encoding porcine FSM synthetase.

Another embodiment of the present invention provides nucleic acid sequences representing genomic DNA of the porcine FSM synthetase gene (Table 3, Seq. ID Nos. 3-15; Table 4, Seq. ID No. 16; Table 5, Seq. ID No. 17 and Table 5 Seq ID No. 18). Seq. ID No. 3 represents nucleic acid sequence of exon 1, Seq. ID Nos. 4-9 represent the full length nucleic acid sequence of exons 2-7, respectively. Seq. ID Nos. 10-15 represent full length nucleic acid sequences of introns 1-6, respectively. Seq. ID Nos. 16-18 represent genomic nucleic acid sequence of the porcine FSM synthetase gene. In one embodiment, the present invention provides at least 17 contiguous nucleotides of Seq ID Nos. 1-18. In particular embodiments, nucleotides containing at least 150, 250, 500 or 1000 contiguous nucleotides of Seq ID Nos. 1-18, particularly Seq. ID No. 17, are provided. In a further embodiment, nucleotides containing at least 1350, 1500 or 2000 contiguous nucleotides of Seq ID Nos. 1-18, particularly Seq ID Nos. 1 and 16, are provided.

In one embodiment, polynucleotide primers are provided that are capable of hybridizing to porcine FSM synthetase cDNA or genomic sequence, such as Seq. ID Nos. 1, 3-15, or 16. Another embodiment provides polynucleotide probes capable of hybridizing to porcine FSM synthetase nucleic acid sequence, such as Seq. ID Nos. 1, 3-15, or 16. The polynucleotide primers or probes can have at least 20 bases, preferably 30 bases, more preferably 50 bases which hybridize to a polynucleotide of the present invention. The probe or primer can be at least 14 nucleotides in length, and in a preferred embodiment, are at least 15, 20, 25 or 28 nucleotides in length.

In another aspect of the present invention, mammalian cells lacking at least one allele of porcine FSM synthetase gene are provided. These cells can be obtained as a result of homologous recombination. Particularly, by inactivating at least one allele of the porcine FSM synthetase gene, cells can be produced which have reduced capability for expression of the functional FSM synthetase enzyme.

In one embodiment of the present invention, targeting vectors are provided wherein homologous recombination in somatic cells can be detected. These targeting vectors can be transformed into mammalian cells to target the porcine FSM synthetase gene via homologous recombination. In one embodiment, the targeting construct inserts the selectable maker gene into the gene encoding the porcine FSM synthetase enzyme so as to be in reading frame with the upstream sequence and produce an inactive fusion protein. Cells can be transformed with the constructs using the methods of the invention and are selected by means of the selectable marker and then screened for the presence of recombinants.

In another embodiment, targeting vectors can contain a 3' recombination arm and a 5' recombination arm. Each arm can contain a region of DNA homologous to the porcine FSM synthetase gene sequence. The targeting vector can also contain a promoter gene sequence and a selectable marker gene. The homologous DNA sequence can include at least 50 bp, 100 bp, 500 bp, 1kbp, 2 kbp, 4 kbp, 5 kbp, 10 kbp, 15 kbp, 20 kbp, or 50 kbp of sequence homologous with the porcine FSM synthetase gene, for example, Seq. ID Nos. 3-15 or 16. In one specific embodiment, the targeting vectors include the selectable marker gene for enhanced green fluorescent protein (eGFP) or the neomycin resistant gene (see, for example, FIG. 4).

In a further aspect of the present invention, mammalian cells lacking one allele, optionally both alleles of the porcine FSM synthetase can be used as donor cells to provide the nucleus for nuclear transfer into enucleated oocytes to produce cloned, transgenic animals. Alternatively, porcine FSM synthetase knockouts can be created in embryonic stem cells, which are then used to produce offspring. Cells, tissues and/or organs can be harvested from these animals for use in xenotransplantation strategies.

In one aspect of the present invention, a pig can be prepared by a method in accordance with any aspect of the present invention. Genetically modified pigs that lack the FSM synthetase gene can be used as a source of tissue and/or organs for transplantation therapy. A pig embryo prepared in this manner or a cell line developed therefrom can also be used in cell-transplantation therapy. Accordingly, there is provided in a further aspect of the invention a method of therapy comprising the administration of genetically modified porcine cells lacking porcine FSM synthetase to a patient, wherein the cells have been prepared from an embryo or animal lacking FSM synthetase. This aspect of the invention extends to the use of such cells in medicine, e.g. cell-transplantation therapy, and also to the use of cells derived from such embryos in the preparation of a cell or tissue graft for transplantation. The cells can be organized into tissues or organs, for example, heart, lung, liver, kidney, pancreas, corneas, nervous (e.g. brain, central nervous system, spinal cord), skin, or the cells can be islet cells, blood cells (e.g. haemocytes, i.e. red blood cells, leucocytes) or haematopoietic stem cells or other stem cells (e.g. bone marrow).

In another aspect of the present invention, porcine FSM synthetase deficient pigs also lack other genes associated with an adverse immune response in xenotransplantation, such as, for example, α(1,3)GT, CMP-NeuAc hydroxylase (see, for example, U.S. Patent Application 60/476,396), porcine iGb3 synthase (see, for example, U.S. Patent Application 60/517,524) and/or the invariant chain (see, for example, U.S. Patent Application 60/505,212). In addition, FSM synthetase deficient pigs, optionally lacking one or more additional genes associated with an adverse immune response, can be modified to express complement inhibiting proteins such as, for example, CD59, DAF, and/or MCP. In other embodiments, pigs lacking expression of other genes associated with an adverse immune response, such as, for example, α(1,3)GT, isogloboside 3 synthase (iGb3 synthase), CMP-NeuAc hydroxylase, and/or the invariant chain can be further modified to eliminate the expression of at least one allele of the FSM synthetase gene. In another embodiment, porcine expressing complement inhibiting proteins such as, for example, CD59, DAF, and/or MCP can be further modified to eliminate the expression of at least one allele of the FSM synthetase gene. These animals can be used as a source of tissue and/or organs for transplantation therapy. A pig embryo prepared in this manner or a cell line developed therefrom can also be used in cell-transplantation therapy.

DESCRIPTION OF THE INVENTION

Elimination of the FSM synthetase gene can reduce a pig organ's immunogenicity by reducing the expression of the immunogenic FSM antigen and remove an immunological barrier to xenotransplantation. The present invention is directed to novel nucleic acid sequences encoding cDNA and peptides of the porcine FSM synthetase. Information about the genomic organization, intronic sequences and regulatory regions of the gene are also provided. In one aspect, the invention provides isolated and substantially purified cDNA molecules having Seq. ID No. 1, or a fragment thereof. In another aspect of the invention, predicted amino acid sequences having Seq. ID No. 2, or a fragment thereof, are provided. In another aspect of the invention, DNA sequences comprising genomic DNA of the FSM synthetase gene are provided in Seq. ID Nos. 3-15 and 16, or a fragment thereof. In another aspect, primers for amplifying porcine FSM synthetase cDNA or genomic sequence derived from Seq. ID Nos. 1, 3-15 and 16 are provided. Additionally, probes for identifying FSM synthetase nucleic acid sequences derived from Seq. ID Nos. 1, 3-15 and 16 are provided. DNA represented by Seq. ID No. 3-15 and 16 can be used to construct pigs lacking functional FSM synthetase genes. In an alternate embodiment, FSM synthetase-deficient pigs also lack genes encoding other genes associated with adverse immune responses in xenotransplantation, such as, for example, the α1,3galactosyltransferase gene, the isogloboside 3 synthase gene, the CMP-NeuAc hydroxylase gene, or the porcine invariant chain gene. In another embodiment, pigs lacking FSM synthetase and other genes associated with adverse immune responses in xenotransplantation express complement inhibiting factors such as, for example, CD59, DAF, and/or MCP.

BRIEF DESCRIPTION OF THE FIGURES

FIG. 1 represents the genomic organization of the porcine FSM synthetase gene. Shaded bars depict each numbered exon. The length of the introns between the exons is indicated across the bottom axis labeled base pairs. The promoter region of the gene is depicted by an encircled letter P. The start codon is illustrated by a non shaded box contained within exon 2. The stop codon TGA is depicted by a patterned box within exon 7.

FIG. 2 depicts the cDNA sequence of the porcine FSM synthetase gene (SEQ ID No. 1).

FIG. 3 depicts the amino acid sequence of the porcine FSM synthetase gene (SEQ ID No. 2).

FIG. 4 illustrates representative targeting vectors to knock-out the FSM synthetase gene, along with their corresponding genomic organization. The selectable marker genes in these particular non-limiting example are eGFP (enhanced green fluorescent protein) and the neomycin resistance (NeoR) gene. eGFP can be inserted in the DNA constructs to inactivate the porcine FSM synthetase gene. Alternatively, neomycin can be inserted in the DNA construct to inactivate the porcine FSM synthetase gene.

DETAILED DESCRIPTION

Definitions

In order to more clearly and concisely describe and disclose the subject matter of the claimed invention, the following definitions are provided for specific terms used in the specification.

A "target DNA sequence" is a DNA sequence to be modified by homologous recombination. The target DNA can be in any organelle of the animal cell including the nucleus and mitochondria and can be an intact gene, an exon or intron, a regulatory sequence or any region between genes.

A "targeting DNA sequence" is a DNA sequence containing the desired sequence modifications and which is, except for the sequence modifications, substantially isogenic with the target DNA.

A "homologous DNA sequence or homologous DNA" is a DNA sequence that is at least about 85%, 90%, 95%, 98% or 99% identical with a reference DNA sequence. A homologous sequence hybridizes under stringent conditions to the target sequence, stringent hybridization conditions include those that will allow hybridization occur if there is at least 85% and preferably at least 95% or 98% identity between the sequences.

An "isogenic or substantially isogenic DNA sequence" is a DNA sequence that is identical to or nearly identical to a reference DNA sequence. The term "substantially isogenic" refers to DNA that is at least about 97-99% identical with the reference DNA sequence, and preferably at least about 99.5-99.9% identical with the reference DNA sequence, and in certain uses 100% identical with the reference DNA sequence.

"Homologous recombination" refers to the process of DNA recombination based on sequence homology.

"Gene targeting" refers to homologous recombination between two DNA sequences, one of which is located on a chromosome and the other of which is not.

"Non-homologous or random integration" refers to any process by which DNA is integrated into the genome that does not involve homologous recombination.

A "selectable marker gene" is a gene, the expression of which allows cells containing the gene to be identified. A selectable marker can be one that allows a cell to proliferate on a medium that prevents or slows the growth of cells without the gene. Examples include antibiotic resistance genes and genes which allow an organism to grow on a selected metabolite. Alternatively, the gene can facilitate visual screening of transformants by conferring on cells a phenotype that is easily identified. Such an identifiable phenotype can be, for example, the production of luminescence or the production of a colored compound, or the production of a detectable change in the medium surrounding the cell.

The term "porcine" refers to any pig species, including pig species such as, for example, Large White, Landrace, Meishan, and Minipig.

The term "oocyte" describes the mature animal ovum which is the final product of oogenesis and also the precursor forms being the oogonium, the primary oocyte and the secondary oocyte respectively.

The term "fragment" means a portion or partial sequence of a nucleotide or peptide sequence.

DNA (deoxyribonucleic acid) sequences provided herein are represented by the bases adenine (A), thymine (T), cytosine (C), and guanine(G).

Amino acid sequences provided herein are represented by the following abbreviations:

| | |
|---|---|
| A | alanine |
| P | proline |
| B | aspartate or asparagine |
| Q | glutamine |
| C | cysteine |
| R | arginine |
| D | aspartate |
| S | serine |
| E | glutamate |
| T | threonine |
| F | phenylalanine |
| G | glycine |
| V | valine |
| H | histidine |
| W | tryptophan |
| I | isoleucine |
| Y | tyrosine |

| | -continued |
|---|---|
| Z | glutamate or glutamine |
| K | lysine |
| L | leucine |
| M | methionine |
| N | asparagine |

"Transfection" refers to the introduction of DNA into a host cell. Most cells do not naturally take up DNA. Thus, a variety of technical "tricks" are utilized to facilitate gene transfer. Numerous methods of transfection are known to the ordinarily skilled artisan, for example, $CaPO_4$ and electroporation. (J. Sambrook, E. Fritsch, T. Maniatis, Molecular Cloning: A Laboratory Manual, Cold Spring Laboratory Press, 1989). Transformation of the host cell is the indicia of successful transfection.

I. cDNA Sequence of the Porcine FSM Synthetase Gene.

One aspect of the present invention provides novel nucleic acid cDNA sequences of the porcine FSM synthetase gene (FIG. 2, Table 1, Seq. ID No. 1). Another aspect of the present invention provides predicted peptide sequences of the porcine FSM synthetase gene (FIG. 3, Table 2, Seq. ID No. 2). The ATG start codon for the full-length cDNA is located within exon 2 of the genomic DNA sequence. The TGA stop codon is at about 682 base pairs from the beginning of exon 7. Nucleic and amino acid sequences at least 90, 95, 98 or 99% homologous to Seq. ID Nos. 1 or 2 are provided. In addition, nucleotide and peptide sequences that contain at least 10, 15, 17, 20 or 25 contiguous nucleic or amino acids of Seq ID Nos 1 or 2 are also provided. Further provided are fragments, derivatives and analogs of Seq. ID Nos. 1-2. Fragments of Seq. ID Nos. 1-2 can include any contiguous nucleic acid or peptide sequence that includes at least about 10 bp, 15 bp, 17 bp, 20 bp, 50 bp, 100 bp, 500 bp, 1 kbp, 5 kbp or 10 kpb.

TABLE 1

| cDNA SEQUENCE OF PORCINE FSM SYNTHETASE | |
|---|---|
| TGAATTCTAGCTCCGTCTGCCTAGGCTGGTCCGAGGGC | Exons 1-7 Seq. ID No. 1 |
| AAGGGGTCTCCTCCGGACCCCGAAGACACAAGCTGAGA | |
| GCGTGACGGCCCCTGAGAGAGGTGGGCGGATCCGCCAA | |
| GTCACACCCAGGGTCTGCAGGTGCTCAGGCCCAGACGC | |
| TGCAGCCAGAGATGGGCTGCCGCAGACTAGCCGTGGGC | |
| CTGGGGTTCGGCCTGCTGGTGGGCGTGGCCCTCTGCTC | |
| TCTGTGGCTGTATGTGGAGAACGTGCCGCCGCCGGTCT | |
| ATATCCCCTATTACCTCCCCTGCCCTGAGATGTTCAAC | |
| ATGAAGCTCCAGTACAAGGGGGTGAAGCCATTCCAGCC | |
| CGTGGCACAGTCCCAGTAGCCTCAGCCCAAGCTGCTTG | |
| AGCCAAAGCCCTCAGAGCTGCTGACGCTCACGTCCTGG | |
| TTGGCACGCATCGTCTCCGAGGGGACCTTCGACCCTGA | |
| GCTTCTTCATCACATCTACGAGCCACTGAACCTGACCA | |
| TCGGGCTCACGGTGTTTGGCGTGGGGAAGTACACCCAG | |
| GTTCGTCCAGCGCTTCCTGGAGTGGGCCGAGCGCTTCT | |
| TCATGCAGGGCTACGGGGTGCACTACTACATCTTTACG | |

TABLE 1-continued cDNA SEQUENCE OF PORCINE FSM SYNTHETASE

AGCGACCCCGGGGCCGTTGCTGGGGTCCGGCTGGGCCC

GGGCCGCCTCCTCAGCGTCATCGCGATCCGGAGAGCCT

CGCGCTGGGAGGAGGTGTGCACACGCCGGATGGAGGCC

ATCAGCCAGCACATTGCCGGCAGGGCGGACGGGGGAGG

TCGACTACCTCTTCTGCGTGAGCGTGGACATGGTGTTC

CGGAAGCCATGGGCCCCGAGACCTTGGGGACGTGGT

GGGTGCCATTCACGGGGGCTACTTCGCCGCGCGCCGCC

AGGAGTTCCCCTACGAGGGCGGGATGTTTCTACCGCC

TTGGTGGGGACAGCGAGGGGACTTCTATATTATGGT

GGGGCGGTCTTCGGGGGCGGGTGGCCAGGGTGTACGA

GTTCACCCAGGGCTGCCACATGGGCATCCTGGCGGACA

AGGCCAATGGGATCATGGCGGCCTGGGAGGAGGAGAGC

GACCTGAACCGCGGCTTCATCTCCGACAAGCCCTCGAA

GGTGCTGTCCCCCGAGTACCTCTGGGATGACCGCAGGC

CCCAGGCGCCCAGCCTGAAGCTGATGCGCTTTTCCACA

CTGGAGAAAGACACCAACTGGCTGAGGAGCTGACAGCA

GCACAGCCGGGGCTGCTGTGCATGCGGGGGGACCCCAA

GCCGTGCCCGCAGCTCGGCCCAGCAGCGCCTCCTCACC

CGGACGCCTCACTTCCCAAGCCTTCTGTGAACCAGCCG

TGCGCTGCCTACCTCTCAGGGTGCGAGCAGACTGCGAG

GCGTGTGTAAACTGTGAAGGGCTGTGCCCTTGTGAGAA

CACAGAGCCTGTGAGCCAGAAACGGTCAGACGGGAGGA

GAGGGACCAGAGGTAGAAGAAGACGGGACGCGCAGTCC

TCACCGAGCCGAGGTGCCTTGGGGTGGGCGCTGGAGGG

TCAGCGCTGGCCAGTGGCTGAGGTCCCGCCCACCCGCC

TTTTGTGGCCGTTTGTACCTGTGACACATGAGAGAGGT

ATCCTGGACCCCTGTCCTCTGGCTGCAGGGGCCCCGGG

GACTGTTGTGTCCCCCTGCCAGAAGGAGCCAGTAGCTC

ACTCAGGACGCCGACCGAGCCTTCGAAATGGACCCGGG

CTGGGCTCTCTCGTTGCACGTCCAGCCCACCTGTGCAG

TGGACCACGCTCCCTGGTGCCCACGGCGTCCTTTGCAA

GGGGGTTTGGGCAGGTTTTTAATACAGGTGGCATGTGC

TCAGGGCTAAGG

TABLE 2

AMINO ACID SEQUENCE FOR PORCINE FSM SYHTETASE

MRCRRLALGLGFGLLVGVALCSLWLYVENVPPPVYIP    Seq. ID No. 2

YYLPCPEIFNMKLQYKGVKPFQPVAQSQYPQPKLLEP

TABLE 2-continued

AMINO ACID SEQUENCE FOR PORCINE FSM SYHTETASE

KPSELLTLTSWLAPIVSEGTFDPELLHHIYQPLNLTI

GLTVFAVGKYTQFVQRYLESAERFFMQGYRVHYYIFT

SDPGAVPGVPLGPGRLLSVIAIRRPSRWEEVSTRRME

AISQHIAARAHREVDYLFCLSVDMVFRNPWGPETLGD

LVAAIHPGYFAAPRQQFPYERRHVSTAFVADSEGDFY

YGGAVFGGRVARVYEFTQGCHMGILADKANGIMAAWQ

EESHLNRRFISHKPSKVLSPEYLWDDRRPQPPSLKLI

RFSTLDKDTNWLRS

The present invention further provides nucleotide probes and primers which hybridize to the hereinabove-described sequence (Seq. ID Nos. 1). Polynucleotides are provided that can be at least about 80%, 90%, or 95% homologous to Seq. ID No. 1. Polynucleotides that hybridize under stringent conditions to Seq. ID No. 1 are also provided. Stringent conditions describe conditions under which hybridization will occur only if there is at least about 85%, 95% or at least 97% homology between the sequences. Alternatively, the polynucleotide can have at least 20 bases, preferably 30 bases, and more preferably at least 50 bases which hybridize to Seq. ID No. 1. Such polynucleotides can be used as primers and probes to detect the sequences provided herein. The probe or primer can be at least 14 nucleotides in length, and in a preferred embodiment, are at least 15, 20, 25 or 28 nucleotides in length.

II. Genomic Sequences of the Porcine FSM Synthetase Gene

Nucleic acid sequences representing genomic DNA of the porcine FSM synthetase gene (FIG. 1, Table 3 and Table 4) are also provided. Seq. ID No. 3 represents a partial sequence of exon 1. Seq. ID No. 4-9 represent full length sequences of exons 2-7, respectively. Seq. ID Nos. 10-15 represent the complete sequences of introns 2-6, respectively. Seq. ID No. 16 represents the genomic nucleic acid sequence of Exon 1 through Exon 7 (Seq. ID No. 3-15). Seq ID No. 17 represents the genomic nucleic acid sequence of Exon 1 through Intron 6 (Seq ID No. 3-14). Seq ID No. 18 represents the genomic nucleic acid sequence of Exon 1 through Intron 3 (Seq ID No. 3-8). Nucleic and amino acid sequences at least 90, 95, 98 or 99% homologous to Seq. ID Nos. 3-18 are provided. In addition, nucleotide and peptide sequences that contain at least 10, 15, 17, 20 or 25 contiguous nucleic or amino acids of Seq. ID Nos. 3-18 are also provided. Further provided are fragments, derivatives and analogs of Seq. ID Nos. 3-18. Fragments of Seq. ID Nos. 3-18 can include any contiguous nucleic acid or peptide sequence that includes at least about 10 bp, 15 bp, 17 bp, 20 bp, 50 bp, 100 bp, 500 bp, 1 kbp, 5 kbp or 10 kpb.

In particular embodiments, any contiguous nucleic acid sequence at least about 1335 bp, 1340 bp, 1350 bp, 1375 bp, 1400 bp, 1500 bp, 1600 bp, 1700 bp, 2000 bp, 5000 bp or 10,000 bp of Seq ID No. 16 are provided. In another embodiment, any contiguous nucleic acid sequence at least about 135 bp, 140 bp, 145 bp, 150 bp, 175 bp, 200 bp, 250 bp, 300 bp, 400 bp, 500 bp, 600 bp, 700 bp, 800 bp, 900 bp, 1000 bp, 1200 bp, 1335 bp, 1340 bp, 1350 bp, 1375 bp, 1400 bp, 1500 bp, 1600 bp, 1700 bp, 2000 bp, 5000 bp or 10,000 bp of Seq ID No. 17 are provided. In another embodiment, any contiguous nucleic acid sequence at least about 10 bp, 15 bp, 17 bp, 20 bp, 50 bp, 100 bp, 135 bp, 140 bp, 145 bp, 150 bp, 175 bp, 200 bp, 250 bp, 300 bp, 400 bp, 500 bp, 600 bp, 700 bp, 800 bp, 900 bp, 1000 bp, 1200 bp, 1335 bp, 1340 bp, 1350 bp, 1375 bp, 1400 bp, 1500 bp, 1600 bp, 1700 bp, 2000 bp, 5000 bp or 10,000 bp of Seq ID No. 18 are provided.

TABLE 3

GENOMIC SEQUENCE OF PORCINE FSM SYNTHETASE GENE

| | | |
|---|---|---|
| TGAATTCTAGCTCCGTCTGCCTACGCTGGTCCGACCGCAAGGG | exon 1 | Seq. ID No. 3 |
| gtgagtctgcagccggtaaggacaatcgcgctccctccgctgcgcctt<br>gtccctgccccgcgcccagccggaggaagagcgccgcgagtccccagc<br>ccgcagtggtagtcgagatgtgtgtcttcggccccaggctcctgggtg<br>cagatccccggctggggcggaccgagctcggccctggctgtgagtcgg<br>cagagcgtccccggcggcctgggccccgcgggagggagaatctcgcgg<br>agccaactgtcgagggggccttggaggacgcttcgccccaaaccggg<br>atgggaaaactgaggtctgtagagggagggagagggattgggaacggc<br>cttgcagaggccaccgaatgagcagggccaaagccccagaactctggc<br>ccggggatctttgacctcgagcggatccccacagagcggccaggggtc<br>cggtgctcactgcttactgtgacacaaccctcccggtacatcagggag<br>tgcgtattgcgtcttgtccccctgcaccaagccccctctagccgaggag<br>gaccccgacgctgtggcggagcgggacgagagtgacttgcccaagat<br>tatcgccgagcgggtgcgagctgaagctcgttcctgcggtccccggga<br>gagtccaggctgccgcctcctggagcaacgccctgctgccaccctgc<br>ccctgctcccgcccgggggggatcgcggccgccctcgctgcgcagca | intron 1 | Seq. ID No. 4 |

TABLE 3-continued

GENOMIC SEQUENCE OF PORCINE FSM SYNTHETASE GENE tcccgcttcccaggcccggcgtgtcccgctgtgccggctcagagctt
aatttcggcgtcctcattgtctccctggggaatccctctccaagatca
gcccaagcgctgttgccctggtccggaggatggccgcccttcgctcgc
cgcaggagtttggagggagacctgagagccaaggcagggaccggtc
cttggggcacggctgcaggcttcgggtgagcaatgagcctctgtcccc
gggtcaacttgccagaactgccccatctgggcctagggtccagcagga
tgagaagatgacctggaatccacagtccctagcggggctgcccgggg
gagggcggagcagcaaggctggggcaactatcctccagataaggagca
ttcctttgcag

| | | |
|---|---|---|
| GTCTCCTCCGGACCCCGAAGACACAAGCTCAGAGCCTGACGGCCCCTG<br>AGAGAGGTGGGCGGATCCGCCAAGTCACACCCAGGCTCTGCAGGTGCT<br>CAGGCCCAGACGCTGCACCCAGAGATGCGCTGCCGCAGACTAGCCCTG<br>GGCCTGGGGTTCGGCCTGCTGGTGGGCGTGGCCCTCTGCTCTCTGTG | exon 2 | Seq. ID No. 5 |
| gtgagcatgccccgtggagccctccggccccacccgactcctccctct<br>ctcagcatctcaaccccaagcctgacccttcactgaactcccagggc<br>tctcatccgcctctcctgacacacctgtccttctggcgccgtaagaga<br>tgaactagtctggacttacggattttgctttgcactggctctttcctc<br>tgcctggactattcttctagccatgttaacgaggaactccagtttatg<br>ctccaaaattcaccccaatgtgttctttctgcaaagttcctggccccc<br>ccaccccaccccacccccgcccctgtgtgcagggtctggcatca<br>ggaacattcctgccccaggaatgaagggctgcatggctctataataac<br>tgtgttgccacagaccgggggctttgccatccacggttcgccagaccc<br>aaggagtgattggtgggtgggggtggggtcccaggtgcacccctgg<br>gggccttcattcccactaacatggaccaagtgggttttcagcctcagg<br>ttcaaagtcgagtcagccagtgttcttccctcccag | intron 2 | Seq. ID No. 6 |
| GCTGTATGTGGAGAACGTGCCGCCGCCGGTCTATATCCCCTATTACCT<br>CCCCTGCCCTGAGATCTT | exon 3 | Seq. ID No. 7 |
| gtgagtatgagacggggagaatgggcgagatgggaggggttttaagg<br>ccgctttgcaggttcttacattctcagctcaggattctgatcagtgtg<br>attaaacagtgaggcaatttatgaacggctgcaaatgtggagtaaaaa<br>ctcccctgtttcagtcccgaggggtgccctttggcatgttgtgtggct<br>ctgagcctcacttgctgcacgtgtaaaaggggcgatagatggtacct<br>gtgaccgtgctggtgtcacccctggcacataggaggtgcccaggaaag<br>agtgcttttaggacaagacctttttgctcaatttggtgttctgcgtgg<br>attcgaggaacaaggtgcccagtctctcccacatggcaaggctgactt<br>tttgacagctaagtgtgacacagatcaagtgtgatgtaggttgggaca<br>gtcccgagggtgcatctggccccctggtcttttgctgtccatgacagc<br>agaaggaaagtaaagcatgcatcgcaagggaagttcctgtcgtggctc<br>agtggaaatggatctgacgcgtatccatgaggatgcaggttcgatccc<br>tggcctcactcagtgggttaaggatccggtgttgccgtgagctgtggt<br>gtagattgcagacacgactcggatctggcatggctgtggctgtggtgt<br>aggccaggggctacagctccccggaacctccatatgctgcgggtgcgg<br>ccctaaaaagacaaccaaaaaaagcatgcatcacagggagttccctgg<br>tagtctagtggttaggattcagtgcttatgttctaaaaaagcagaaag<br>gctgcttgcttttgaaaacagttgtgaccacaatgttttggattttt<br>atcctgtttcccggatttggcctttattttggcatctggtcaccatt<br>attttattctaacctgggtctgggcccctgaacccctttcccaccaa<br>caacttttgaagcatttaggtggtttccaggtgcccagcgttctaaatt<br>agtttgtaatgagcagctctggacataaagcttttcccgcctaaaga<br>tcctttcatctggtatgttcctgagccaaaggatatggctgggttctc<br>atccgcttgctctcagagggaccagaccgtcccacactcacgctcat<br>ccccgcacccctacgcaccccccgccccagcagctgcgccgccgctggg<br>ctaggactggacataccagctgtcatgagaaacaaaacccaaaccacc<br>tcgctgattggagagatgggaaatgcagtctggtgtaaattacgcttc<br>tttgatttgttcggggccctcatttccccaggccttccatgaattg<br>aattctgcctccatgaacttgccctctcacctccttccctcccgggcc<br>tctttgctgtcctctgtccccacccttgtatttgctacctctttttt<br>ttttttttttttttttttcctttgccatttcttggccgctcccc<br>gacatatggaggttcccaggctaggggtcgaatcggactgtagccacc<br>agcctacgccagagccacagcaacatgggatccaagcccgtctgcga<br>cctacaccacagttcacggcaacgccagatccttaacccacgagtgag<br>gacggggatcgaacccgccacctcatggttcctagtcggattcatcaa<br>tcactgagccacaacgggaactccagtatttgctacatcttgctactt<br>ttttttttcttctagtttgtctacctcttggttcttctgagggtttg<br>tgtgtgtgtgttgtgatagattgaggctggagatttgtgactttattt<br>aatgtttagttatgtatgtatttattggccacacccacggcatatgga<br>agttcccaggcgaggggttgaatcggagcccagctgccagcctacac<br>cacagccacagcaacacaggatccgagctgcgtctgtgacctataccc<br>cagctcacggcagcgctggatccttaactcactgagtgagaccaggga<br>tcgaacctgcgtcctcatggatactagtcgggtttgttaccactgagc<br>cacgacgggaactcccgaggatagtctttatataaggtcagctggtgt<br>cggcgttactcacatgtgcaaaatacagaccttcacagccgtgcctgg<br>attgatggccgtgtaactgggtcccacaaccacccatcaccgtgggct | intron 3 | Seq. ID No. 8 |

TABLE 3-continued

GENOMIC SEQUENCE OF PORCINE FSM SYNTHETASE GENE

| | | |
|---|---|---|
| caggttaagcaactcgcccaggctagaaagtggcagaaccgggcttac<br>tgggcctttgcagcttctcagtccttctacccaatgcccaggcccttc<br>cagagcaacatgtttgcaagagagacagaaaaagactttggagacaag<br>tggtaccgggtttgaatcacagcaaccccggacagaccgcctctgtag<br>aagcccagccctgcagtgggggaggtctaagagagtctgcgtggagc<br>ctggtggggagggggtacctgtcccgtgggggggttcatcttggcttc<br>cctgccgagcatccctgcccccggcccggcactaatggctgtgtctc<br>gcctctcccaccag | | |
| CAACATGAAGCTCCAGTACAAGGGGGTGAAGCCATTCCAGCCCGTGGC<br>ACA | exon 4 | Seq. ID No. 9 |
| gtaagcagactgtcacttcccccttggtggccccggggggtggggcg<br>gcctcccctaccaccggcccttcttggttgcag | intron 4 | Seq. ID No. 10 |
| GTCCCAGTACCCTCAGCCCAAGCTGCTTGAGCCAA | exon 5 | Seq. ID No. 11 |
| gtaggtgtcaattaggggcggggcacagaagggagactcctggggcgg<br>aggtggggggacagagcgctgattgacaagttggggtggtggagggg<br>tcaggtggccttgggagccgggtggtctggcacctgggctccagtcca<br>gccctgtcactagctgtgtggcctacccaactgctctgagcttttcct<br>gcgtgggtggatagtaataccccccacctggagcgttcccgctgtggct<br>cagcaggtgaaggacccagtgaggtctccgtgaggatgcgggctccat<br>ccctggcctcgctcagtgggttaaggacctggcgtggctgcaagctgt<br>gccacaggtcgcatatgcggctcagggctggtgtggctgtggctgtgg<br>cgtaggccgaagctgcagctccagttctccacccctggcccgggaact<br>tccatgcgccacaggtacggccatactgataataataacaataatagt<br>aataatgataataccccacctcataggaggttacagggcccgacgagat<br>ggtgtttgcaaaacgcagggcactgtgcctgcgccctacggggtgccc<br>gacccaccgttaataatggtatcaatgactcccgtttctgaggcactt<br>ggcagacaccagaaatgccaggcctttccagaccctggacgcctggtc<br>ctcccgaccatgctgagaagtagctgttactacccacactttccacgt<br>gaggctcctggagcccagagacaggagtgaagctgcccagggccacac<br>agcacaggaggcaggaccaggatgagactgaggcttttcacaaggggag<br>cgtctcagccccacggcctcctgtgctgccag | intron 5 | Seq. ID No. 12 |
| GCCCTCAGAGCTCCTGACGCTCACGTCCTGGTTGGCACCCATCGTCTC<br>CGAGGGCACCTTCGACCCTGAGCTTCTTCATCACATCTACCAGCCACT<br>GAACCTGACCATCGGGCTCACGGTGTTTGCCGTGGGGAA | exon 6 | Seq. ID No. 13 |
| gtgagtcgtgggctgggcgtggggagggtgggtatagattctgaaccc<br>caggaatgtatggtctggggacagacaggaccccgcccaggcaccagg<br>gaggccctgagccaggtgctgagcaggtgggaagcacagggtcgagcg<br>tgatggttgcaggggggcttcctggaggaaggggggtctggctctggca<br>gcgaagcaggggagcggcccaggtgagagatcgatggcacctttgtca<br>ggagacaccttgtcccctaccccttctgcttccctgagccgcccag<br>gcaggtggggagggatagaaagcccccccaaccacctcccataaatggg<br>ggtccctggtcgggccacacgcaggtcaagagacctgggcagagcagc<br>ccggcccccaggagcctctctccaacacgccctcccccggcgggcccg<br>ctgccctctgttcagcctgttctcccctctcctccctcagcctgcctg<br>gcatttcctaaattaaccgccacctggcagcttccctcggggacccttt<br>tctgggagtcctgagagagggggccctaatggggtcctaatgcccaaag<br>cgctgtccagatgctggatggctcagcgggggtcaagaccccccctcc<br>cccgccaccccagcccagtcagcacccagcatcacaccttccctcgat<br>gcagccactcaccgcctgtgtctataagatgggtgtgtggtccctgcc<br>tcctagggagttgacgaggcctgaaggagtcccttaaaacaggagtcc<br>cttagaacactgcctggcacttagtaagtgctcaataaaagttagctc<br>aggagttccctggtagcctagcggttaaggtcctggtgttgtcactgc<br>tgtggcgcgattggctccctggactgagaacttccacatgttgtggg<br>tgcggggaaaaagaaagttagctctggagttcccatcgtgactcagtg<br>gttaatgaatctgactagcatccatgaggacgcaggttcgatcccagg<br>cctcgctcagtgagttaaggatccgacattgccatgagctgtggtgta<br>ggtcgcagacacggctcggatctggcatgactgtggctgtggcgtagg<br>ccgtcggctacagctctgattggaccctagcctggaaacctccatat<br>gccgtgggtgcagccctcaaaagacaaacaaaaaaggttagctcagtc<br>tgtgaatgtaagactcctcgagggtcagcctaggacggtcttaagagg<br>ctggtgctgtgagtgtgggaatttgacaagtaaggactcggaggagcc<br>tcttgagccgggaagctgggaggtggaccccagcctggccgaccctgg<br>gctctgtgccccgtgtggtgccagcccgtggtggggactcaggcagtg<br>gccctgctgaggcggtggtggccactgggctctcgtccacag | intron 6 | Seq. ID No. 14 |
| GTACACCCAGTTCGTCCAGCGCTTCCTGGAGTCGGCCGAGCGCTTCTT<br>CATGCAGGGCTACCGGGTGCACTACTACATCTTTACCAGCGACCCCGG<br>GGCCGTTCCTGGGGTCCCGCTGGGCCCGGGCCGCCTCCTCAGCGTCAT<br>CGCCATCCGGAGACCCTCCCGCTGGGAGGAGGTCTCCACACGCCGGAT<br>GGAGGCCATCAGCCAGCACATTGCCGCCAGGGCGCACCGGGAGGTCGA<br>CTACCTCTTCTGCCTCAGCGTGGACATGGTGTTCCGGAACCCATGGGG | exon 7 | Seq. ID No. 15 |

TABLE 3-continued

GENOMIC SEQUENCE OF PORCINE FSM SYNTHETASE GENE

```
CCCCGAGACCTTGGGGGACCTGGTGGCTGCCATTCACCCGGGCTACTT
CGCCGCGCCCCGCCAGCAGTTCCCCTACGAGCGCCGGCATGTTTCTAC
CGCCTTCGTGGCGGACAGCGAGGGGGACTTCTATTATGGTGGGGCGGT
CTTCGGGGGGCGGGTGGCCAGGGTGTACGAGTTCACCCAGGGCTGCCA
CATGGGCATCCTGGCGGACAAGGCCAATGGCATCATGGCGGCCTGGCA
GGAGGAGAGCCACCTGAACCGCCGCTTCATCTCCCACAAGCCCTCCAA
GGTGCTGTCCCCCGAGTACCTCTGGGATGACCGCAGGCCCCAGCCCCC
CAGCCTGAAGCTGATCCGCTTTTCCACACTGGACAAAGACACCAACTG
GCTGAGGAGCTGACAGCACAGCCGGGGCTGCTGTGCATGCGGGGGGAC
CCCAAGCCCTGCCCCCAGCTCGCCCCAGCAGCGCCTCCTCACCCGGAC
GCCTCACTTCCCAAGCCTTCTGTGAAACCAGCCCTGCGCTGCCTACCT
CTCAGGCTGCCAGCAGACTCCGAGGCCTGTGTAAACTGTGAAGGGCTG
TGCCCTTGTGAGAACACACAGCCTGTGAGCCAGAAACGGTCAGACGGG
AGGAGACGGACCAGAGGTAGAAGAAGACGGGACCCGCAGTCCTCACCC
AGCCCACGTGCCTTTGGGGTGGGCGCTGGAGGGTCAGCCCTGCCCAGT
GCCTGACGTCCCGCCCACCCCCCTTTTGTGGCCGTTTGTACCTCTGAC
ACATGAGAGAGGTATCCTGGACCCCTGTCCTCTGGCTGCAGGGGCCCC
GGGGACTGTTCTGTCCCCCTGCCACAAGGAGCCAGTACCTCACTCAGG
ACCCCGACCGAGCCTTCGAAATGGACCCCGCCTCTGCTCTCTCGTTCC
ACGTCCAGCCCACCTCTGCAGTGGACCACGCTCCCTGGTGCCCACCGC
CTCCTTTGCAAGGGGGTTTGGGCAGCTTTTTAATACAGGTGGCATGTG
CTCAGCCCTAACC
```

Tables 4, 5 and 6: Genomic Sequence of Porcine Fsm Synthetase Gene

TABLE 4

| | |
|---|---|
| TGAATTCTAGCTCCGTCTGCCTACGCTGGTCCGACCGCAAGGGgtgagt | Full length Seq. ID No. 16 |
| ctgcagccggtaaggacaatcgcgctccctccgctgcgccttgtccctg | Genomic |
| ccccgcgcccagccggaggaagagcgccgcgagtcccccagcccgcagtg | Sequence |
| gtagtcgagatgtgtgtcttcggccccaggctcctgggtgcagatcccc | |
| ggctggggcggaccgagctcggccctggctgtgagtcggcagagcgtcc | |
| ccggcggcctgggccccgcgggagggagaatctcgcggagccaactgtc | |
| gaggggggccttggaggacgcttcgccccaaaccgggatgggaaaactg | |
| aggtctgtagagggagggagagggattgggaacggccttgcagaggcca | |
| ccgaatgagcagggccaaagccccagaactctggcccggggatctttga | |
| cctcgagcggatccccacagagcggccaggggtccggtgctcactgctt | |
| actgtgacacaaccctcccggtacatcagggagtgcgtattgcgtcttg | |
| tccccctgcaccaagcccctctagccgaggaggaccccgacgctgtggc | |
| ggagcggggacgagagtgacttgcccaagattatcgccgagcgggtgcg | |
| agctgaagctcgttcctgcggtccccgggagagtccaggctgccgcctc | |
| ctggagcaacgccctgctgccaccccctgccctgctcccgcccgggggg | |
| gatcgcggccgcccctcgctgcgcagcatcccgcttcccaggcccggcg | |
| tgtccccgctgtgccggctcagagcttaatttcggcgtcctcattgtct | |
| ccctggggaatccctctccaagatcagcccaagcgctgttgccctggtc | |
| cggaggatggccgccccttcgctcgccgcaggagtttgggagggagacct | |
| gagagccaaggcaggggaccggtccttggggcacggctgcaggcttcgg | |
| gtgagcaatgagcctctgtccccgggtcaacttgccagaactgccccat | |
| ctgggcctagggtccagcaggatgagaagatgacctggaatccacagtc | |
| ccctagcggggctgcccgggggagggcggagcagcaaggctggggcaac | |
| tatcctccagataaggagcattcctttgcagGTCTCCTCCGGACCCCGA | |
| AGACACAAGCTCAGAGCCTGACGGCCCTGAGAGAGGTGGGCGGATCCG | |
| CCAAGTCACACCCAGGCTCTGCAGGTGCTCAGGCCCAGACGCTGCACCC | |
| AGAGATGCGCTGCCGCAGACTAGCCCTGGGCCTGGGGTTCGGCCTGCTG | |
| GTGGGCGTGGCCCTCTGCTCTCTGTGgtgagcatgccccgtggagccct | |
| ccggccccacccgactcctccctctctcagcatctcaaccccccaagcct | |
| gacccttcactgaactcccagggctctcatccgcctctcctgacacacc | |
| tgtccttctggcgccgtaagagatgaactagtctggacttacggatttt | |
| gctttgcactggctcttttcctctgcctggactattcttctagccatgtt | |
| aacgaggaactccagtttatgctccaaaattcacccaatgtgttctttt | |
| ctgcaaagttcctggccccccaccccaccccaccccgcccctttg | |
| tgtgcagggtctggcatcaggaacattcctgccccaggaatgaagggct | |
| gcatggctctataataactgtgttgccacagaccgggggctttgccatc | |
| cacggttcgccagacccaaggagtgattggtggggtggggtgggggtc | |
| ccaggtgcacccctgggggccttcattcccactaacatggaccaagtgg | |
| gttttcagcctcaggttcaaagtcgagtcagccagtgttcttccctccc | |
| agGCTGTATGTGGAGAACGTGCCGCCGCCGGTCTATATCCCCTATTACC | |
| TCCCCTGCCCTGAGATCTTgtgagtatgagacggggagaatgggcgaga | |
| tgggagggttttaaggccgctttgcaggttcttacattctcagctca | |
| ggattctgatcagtgtgattaaacagtgaggcaatttatgaacggctgc | |
| aaatgtggagtaaaaactcccctgtttcagtcccgaggggtgcccttg | |
| gcatgttgtgtggctctgagcctcacttgctgcacgtgtaaaaggggggc | |

TABLE 4-continued

```
gatagatggtacctgtgaccgtgctggtgtcaccctggcacataggag
gtgcccaggaaagagtgcttttaggacaagaccttttgctcaatttgg
tgttctgcgtggattcgaggaacaaggtgcccagtctctcccacatggc
aaggctgacttttgacagctaagtgtgacacagatcaagtgtgatgta
ggttgggacagtcccgagggtgcatctggcccctggtcttttgctgtc
catgacagcagaaggaaagtaaagcatgcatcgcaagggaagttcctgt
cgtggctcagtggaaatggatctgacgcgtatccatgaggatgcaggtt
cgatccctggcctcactcagtgggttaaggatccggtgttgccgtgagc
tgtggtgtagattgcagacacgactcggatctggcatggctgtggctgt
ggtgtaggccaggggctacagctccccggaacctccatatgctgcgggt
gcggccctaaaaagacaaccaaaaaaagcatgcatcacagggagttccc
tggtagtctagtggttaggattcagtgcttatgttctaaaaaagcagaa
aggctgcttgcttttgaaaacagttgtgaccacaatgttttggatttt
tatcctgtttccccggatttggccttattttggcatctggtcaccatt
attttattctaacctgggtctgggccccctgaaccccttcccaccaac
aactttgaagcatttaggtggtttccaggtgcccagcgttctaaattag
tttgtaatgagcagctctggacataaagcttttcccgcctaaagatcc
tttcatctggtatgttcctgagccaaaggatatggctgggttctcatcc
gcttgctctccagagggaccagaccgtcccacactcacgctcatcccg
cacccctacgcaccccgccccagcagctgcgccgccgctgggctagga
ctggacataccagctgtcatgagaaacaaaaccaaaccacctcgctga
ttggagagatgggaaatgcagtctggtgtaaattacgcttctttgattt
gttcggggccctcatttccccaggcctttccatgaattgaattctgcc
tccatgaacttgccctctcacctccttccctcccgggcctctttgctgt
cctctgtccccacccttgtatttgctacctcttttttttttttttttt
ttttttttccttttgccatttcttggccgctccccgacatatggagg
ttcccaggctaggggtcgaatcggactgtagccaccagcctacgccaga
gccacagcaacatgggatccaagcccgtctgcgacctacaccacagtt
cacggcaacgccagatccttaacccacgagtgaggacggggatcgaacc
cgccacctcatggttcctagtcggattcatcaatcactgagccacaacg
ggaactccagtatttgctacatcttgctactttttttttctttctagt
ttgtctacctcttggttcttctgagggtttgtgtgtgtgttgtgata
gattgaggctggagatttgtgactttatttaatgtttagttatgtatgt
atttattggccacacccacggcatatggaagttcccaggcgaggggttg
aatcggagcccagctgccagcctacaccacagccacagcaacacagga
tccgagctgcgtctgtgacctataccccagctcacggcagcgctggatc
cttaactcactgagtgagaccagggatcgaacctgcgtcctcatggata
ctagtcgggtttgttaccactgagccacgacgggaactcccgaggatag
tctttatataaggtcagctggtgtcggcgttactcacatgtgcaaaata
cagaccttcacagccgtgcctggattgatggccgtgtaactgggtccca
caaccacccatcaccgtgggctcaggttaagcaactcgcccaggctaga
aagtggcagaaccgggcttactgggcctttgcagcttctcagtccttct
acccaatgccaggccttccagagcaacatgtttgcaagagagacaga
aaaagactttggagacaagtggtaccgggtttgaatcacagcaaccccg
gacagaccgcctctgtagaagcccagcccctgcagtggggaggtctaa
gagagtctgcgtggagcctggtggggaggggtacctgtcccgtgggg
ggttcatcttggcttccctgccgagcatccctgccccggccccggcac
taatggctgtgtctcgcctctcccaccagCAACATGAAGCTCCAGTACA
AGGGGGTGAAGCCATTCCAGCCCGTGGCACAgtaagcagactgtcactt
cccccttggtggccccgggggtggggcggcctcccccttaccaccggc
ccttcttggttgcagGTCCCAGTACCCTCAGCCCAAGCTGCTGAGCCA
AAgtaggtgtcaattagggggcggggcacagaagggagactcctgggcg
gaggtgggggggacagagcgctgattgacaagttgggtggtggaggg
tcaggtggccttgggagccgggtggtctggcacctgggctccagtccag
ccctgtcactagctgtgtggcctacccaactgctctgagcttttcctgc
gtgggtggatagtaataccccccacctggagcgttcccgctgtggctcag
caggtgaaggacccagtgaggtctccgtgaggatgcgggctccatcct
ggcctcgctcagtgggttaaggacctggcgtggctgcaagctgtgccac
aggtcgcatatgcggctcagggctggtgtggctgtggctgtggcgtagg
ccgaagctgcagctccagttctccacccctggcccgggaacttccatgc
gccacaggtacggccatactgataataataacaataatagtaataatga
taatacccacctcataggaggttacagggcccgacgagatggtgtttgc
aaaacgcagggcactgtgcctgcgccctacggggtgcccgacccaccgt
taataatggtatcaatgactcccgtttctgaggcacttggcagacacca
gaaatgccaggcctttccagacccctggacgcctggtcctcccgaccatg
ctgagaagtagctgttactacccacactttccacgtgaggctcctggag
cccagagacaggagtgaagctgcccaggggccacacagcacaggaggcag
gaccaggatgagactgaggcttttcacaaggggagcgtctcagccccac
ggcctcctgtgctgccagGCCCTCAGAGCTCCTGACGCTCACGTCCTGG
TTGGCACCCATCGTCTCCGAGGGCACCTTCGACCCTGAGCTTCTTCATC
ACATCTACCAGCCACTGAACCTGACCATCGGGCTCACGGTGTTTGCCGT
GGGGAAgtgagtcgtgggctgggcgtggggagggtgggtatagattctg
aaccccaggaatgtatggtctgggacagacaggaccccgcccaggcac
cagggaggccctgagccaggtgctgagcaggtgggaagcacagggtcga
gcgtgatggttgcagggggggcttcctggaggaagggggtctggctctgg
cagcgaagcaggggagcggccaggtgagagatcgatggcacctttgtc
aggagacaccttgtcccttaccccttctgcttcccctgagccgcccag
gcaggtggggagggatagaaagccccccaaccacctcccataaatgggg
gtccctggtcgggccacacgcaggtcaagagacctgggcagagcagccc
```

TABLE 4-continued

```
ggcccccaggagcctctctccaacacgccctcccccggcgggcccgctg
ccctctgttcagcctgttctccctctcctccctcagcctgcctggcat
ttcctaaattaaccgccacctggcagcttcctcggggaccctttctgg
gagtcctgagagaggggccctaatgggtcctaatgcccaaagcgctgt
ccagatgctggatggctcagcgggggtcaagaccccccctcccccgcca
ccccagcccagtcagcacccagcatcacaccttccctcgatgcagccac
tcaccgcctgtgtctataagatgggtgtgtggtccctgcctcctaggga
gttgacgaggcctgaaggagtcccttaaaacaggagtcccttagaacac
tgcctggcacttagtaagtgctcaataaaagttagctcaggagttccct
ggtagcctagcggttaaggtcctggtgttgtcactgctgtggcgcggat
tggctccctggactgagaacttccacatgttgtgggtgcggggaaaaag
aaagttagctctggagttcccatcgtgactcagtggttaatgaatctga
ctagcatccatgaggacgcaggttcgatcccaggcctcgctcagtgagt
taaggatccgacattgccatgagctgtggtgtaggtcgcagacacggct
cggatctggcatgactgtggctgtggcgtaggccgtcggctacagctct
gattggaccccctagcctggaaacctccatatgccgtgggtgcagccctc
aaaagacaaacaaaaaaggttagctcagtctgtgaatgtaagactcctc
gagggtcagcctaggacggtcttaagaggctggtgctgtgagtgtggga
atttgacaagtaaggactcggaggagcctcttgagccgggaagctggga
ggtggaccccagcctggccgaccctgggctctgtgccccgtgtggtgcc
agccgtggtggggactcaggcagtggccctgctgaggcggtggtggcgc
actgggctctcgtccacagGTACACCCAGTTCGTCCAGCGCTTCCTGGA
GTCGGCCGAGCGCTTCTTCATGCAGGGCTACCGGGTGCACTACTACATC
TTTACCAGCGACCCCGGGGCCGTTCCTGGGGTCCCGCTGGGCCTGGGCC
GCCTCCTCAGCGTCATCGCCATCCGGAGACCCTCCCGCTGGGAGGAGGT
CTCCACACGCCGGATGGAGGCATCAGCCAGCACATTGCCGCCAGGGCG
CACCGGGAGGTCGACTACCTCTTCTGCCTCAGCGTGGACATGGTGTTCC
GGAACCCATGGGGCCCCGAGACCTTGGGGGACCTGGTGGCTGCCATTCA
CCCGGGCTACTTCGCCGCGCCCCGCCAGCAGTTCCCCTACGAGCGCCGG
CATGTTTCTACCGCCTTCGTGGCGGACAGCGAGGGGGACTTCTATTATG
GTGGGGCGGTCTTCGGGGGGCGGGTGGCCAGGGTGTACGAGTTCACCCA
GGGCTGCCACATGGGCATCCTGGCGGACAAGGCCAATGGCATCATGGCG
GCCTGGCAGGAGGAGAGCCACCTGAACCGCCGCTTCATCTCCCACACGC
CCTCCAAGGTGCTGTCCCCGAGTACCTCTGGGATGACCGCAGGCCCCA
GCCCCCAGCCTGAAGCTGATCCGCTTTTCCACACTGGACAAAGACACC
AACTGGCTGAGGAGCTGACAGCACAGCCGGGGCTGCTGTGCATGCGGGG
GGACCCCAAGCCCTGCCCCCAGCTCGCCCCAGCAGCGCCTCCTCACCCG
GACGCCTCACTTCCCAAGCCTTCTGTGAAACCAGCCCTGCGCTGCCTAC
CTCTCAGGCTGCCAGCAGACTCCGAGGCCTGTGTAAACTGTGAAGGGCT
GTGCCCTTGTGAGAACACACAGCCTGTGAGCCAGAAACGGTCAGAcGGG
AGGAGACGGACCAGAGGTAGAAGAAGACGGGACCCGCAGTCCTCACCCA
GCCCACGTGCCTTTGGGGTGGGCGCTGGAGGGTCAGCCCTGCCCAGTGC
CTGACGTCCCGCCCACCCCCCTTTTGTGGCCGTTTGTACCTCTGACACA
TGAGAGAGGTATCCTGGACCCCTGTCCTCTGGCTGCAGGGGCCCCGGGG
ACTGTTCTGTCCCCCTGCCACAAGGAGCCAGTACCTCACTCAGGACCCC
GACCGAGCCTTCGAAATGGACCCCGCCTGGGCTCTCTCGTTCCACGTCC
AGCCCACCTCTGCAGTGGACCACGCTCCCTGGTGCCCACCGCCTCCTTT
GCAAGGGGTTTGGGCAGCTTTTTAATACAGGTGGCATGTGCTCAGCCC
TAACCagagtttctgcag
```

TABLE 5:

| | |
|---|---|
| TGAATTCTAGCTCCGTCTGCCTACGCTGGTCCGACCGCAAGGG<br>gtgagtctgcagccggtaaggacaatcgcgctccctccgctgcgcctt<br>gtcccctgccccgcgcccagccggaggaagagcgccgcgagtccccagc<br>ccgcagtggtagtcgagatgtgtgtcttcggcccaggctcctgggtg<br>cagatccccggctggggcggaccgagctcggccctggctgtgagtcgg<br>cagagcgtccccggcggcctgggccccgcgggagggagaatctcgcgg<br>agccaactgtcgaggggggccttgaggacgcttcgccccaaaccggg<br>atggaaaactgaggtctgtagagggagggagagggattgggaacggc<br>cttgcagaggccaccgaatgagcagggccaaagcccagaactctggc<br>ccgggatctttgacctcgagcggatcccacagagcggccaggggtc<br>cggtgctcactgcttactgtgacacaaccctcccggtacatcagggag<br>tgcgtattgcgtcttgtccctgcaccaagcccctctagccgaggag<br>gaccccgacgctgtggcggagcgggacgagagtgacttgcccaagat<br>tatcgccgagcgggtgcgagctgaagctcgttcctgcggtccccggga<br>gagtccaggctgccgctcctggagcaacgccctgctgccaccctgc<br>ccctgctccccgcccgggggatcgcggccgcccctcgctgcgcagca<br>tcccgcttccaggcccggcgtgtccccgctgtgccggctcagagctt<br>aatttcggcgtcctcattgtctccctggggaatccctctccaagatca<br>gcccaagcgctgttgccctggtccggaggatggccgcccttcgctcgc<br>cgcaggagtttgggaggagacctgagagccaaggcagggggaccggtc<br>cttggggcacggctgcaggcttcgggtgagcaatgagcctctgtcccc<br>gggtcaacttgccagaactgccccatctgggcctagggtccagcagga<br>tgagaagatgacctggaatccacagtcccctagcggggctgcccgggg<br>gagggcggagcagcaaggctggggcaactatcctccagataaggagca | Partial Seq. ID No. 17<br>Genomic<br>Sequence:<br>Exon 1 to<br>Intron 6 |

TABLE 5:-continued

```
ttccttttgcag
GTCTCCTCCGGACCCCGAAGACACAAGCTCAGAGCCTGACGGCCCCTG
AGAGAGGTGGGCGGATCCGCCAAGTCACACCCAGGCTCTGCAGGTGCT
CAGGCCCAGACGCTGCACCCAGAGATGCGCTGCCGCAGACTAGCCCTG
GGCCTGGGGTTCGGCCTGCTGGTGGGCGTGGCCCTCTGCTCTCTGTG
Gtgagcatgccccgtggagccctccggccccacccgactcctccctct
ctcagcatctcaaccccaagcctgacccttcactgaactcccagggc
tctcatccgcctctcctgacacacctgtccttctggcgccgtaagaga
tgaactagtctggacttacggattttgctttgcactggctctttcctc
tgcctggactattcttctagccatgttaacgaggaactccagtttatg
ctccaaaattcaccccaatgtgttctttctgcaaagttcctggccccc
ccaccccaccccccaccccgcccttgtgtgcagggtctggcatca
ggaacattcctgccccaggaatgaagggctgcatggctctataataac
tgtgttgccacagaccgggggctttgccatccacggttcgccagaccc
aaggagtgattggtgggggtggggtgggggtcccaggtgcaccctgg
gggccttcattcccactaacatggaccaagtgggttttcagcctcagg
ttcaaagtcgagtcagccagtgttcttccctcccag
GCTGTATGTGGAGAACGTGCCGCCGCCGGTCTATATCCCCTATTACCT
CCCCTGCCCTGAGATCTT
gtgagtatgagacggggagaatgggcgagatgggaggggttttttaagg
ccgctttgcaggttcttacattctcagctcaggattctgatcagtgtg
attaaacagtgaggcaatttatgaacggctgcaaatgtggagtaaaaa
ctcccctgtttcagtcccgagggggtgcccttggcatgttgtgtggct
ctgagcctcacttgctgcacgtgtaaaaggggcgatagatggtacct
gtgaccgtgctggtgtcacccctggcacataggaggtgcccaggaaag
agtgcttttaggacaagaccttttgctcaatttggtgttctgcgtgg
attcgaggaacaaggtgcccagtctctcccacatggcaaggctgactt
tttgacagctaagtgtgacacagatcaagtgtgatgtaggttgggaca
gtcccgagggtgcatctggcccccctggtcttttgctgtccatgacagc
agaaggaaagtaaagcatgcatcgcaaggggaagttcctgtcgtggctc
agtggaaatggatctgacgcgtatccatgaggatgcaggttcgatccc
tggcctcactcagtgggttaaggatccggtgttgccgtgagctgtggt
gtagattgcagacacgactcggatctggcatggctgtggctgtggtgt
aggccagggcctacagctccccggaacctccatatgctgcgggtgcgg
ccctaaaaagacaaccaaaaaaagcatgcatcacagggagttccctgg
tagtctagtggttaggattcagtgcttatgttctaaaaaagcagaaag
gctgcttgcttttgaaaacagttgtgaccacaatgttttttggattttt
atcctgtttccccggatttggccttattttggcatctggtcaccatt
atttattctaacctgggtctgggcccctgaacccctttcccaccaa
caactttgaagcatttaggtggtttccaggtgcccagcgttctaaatt
agtttgtaatgagcagctctggacataaagcttttttcccgcctaatga
tcctttcatctggtatgttcctgagccaaaggatatggctgggttctc
atccgcttgctctccagagggaccagaccgtcccacactcacgctcat
ccccgcacccctacgcaccccgcccagcagctgcgccgccgctggg
ctaggactggacataccagctgtcatgagaaacaaaaccaaaccacc
tcgctgattggagagatgggaaatgcagtcagttggtgtaaattacgcttc
tttgatttgttcggggccctcatttccccagcttttccatgaattg
aattctgcctccatgaacttgccctctcacctcctttccctcccgggcc
tctttgctgtcctctgtccccacccttgtatttgctacctcttttttt
ttttttttttttttttccttttgccatttcttggccgctccccc
gacatatggaggttcccaggctaggggtcgaatcggactgtagccacc
agcctacgccagagccacagcaacatgggatccaagccccgtctgcga
cctacaccacagttcacggcaacgccagatccttaacccacgagtgag
gacggggatcgaacccgccacctcatggttcctagtcggattcatca
tcactgagccacaacgggaactccagtatttgctacatcttgctactt
tttttttctttctagtttgtctacctcttggttcttctgagggtttg
tgtgtgtgtgttgtgatagattgaggctggagatttgtgactttattt
aatgtttagttttgtatgtatttattggcctcacccacggcatatgga
agttcccaggcgaggggttgaatcggagcccagctgccagcctacac
cacagccacagcaacacaggatccgagctgcgtctgtgacctataccc
cagctcacggcagcgctggatccttaactcactgagtgagaccaggga
tcgaacctgcgtcctcatggatactagtcgggtttgttaccactgagc
cacgacgggaactcccgaggatagtctttatataaggtcagctggtgt
cggcgttactcacatgtgcaaaatacagaccttcacagccgtgcctgg
attgatggccgtgtaactgggtcccacaaccacccatcaccgtgggct
caggttaagcaactcgcccaggctagaaagtggcagaaccgggcttac
tgggcctttgcagcttctcagtccttctaccaatgcccaggcccttc
cagagcaacatgtttgcaagagagacagaaaaagactttggagacaag
tggtaccgggtttgaatcacagcaaccccggacagaccgcctctgtag
aagcccagccctgcagtgggggaggtctaagagagtctgcgtggagc
ctggtggggaggggtacctgtcccgtgggggggttcatcttggcttc
cctgccgagcatccctgccccggccccggcactaatggctgtgtctc
gcctctcccaccag
CAACATGAAGCTCCAGTACAAGGGGGTGAAGCCATTCCAGCCCGTGGC
ACA
gtaagcagactgtcacttccccttggtggccccggggtgggggcg
gcctccccttaccaccggcccttcttggttgcag
GTCCAGTACCCTCAGCCCAAGCTGCTTGAGCCAAA
gtaggtgtcaattaggggcggggcacagaagggagactcctggggcgg
```

TABLE 5:-continued

```
aggtgggggggacagagcgctgattgacaagttggggtggtggaggggg
tcaggtggccttgggagccgggtggtctggcacctgggctccagtcca
gccctgtcactagctgtgtggcctacccaactgctctgagcttttcct
gcgtgggtggatagtaataccccccacctggagcgtttcccgctgtgct
cagcaggtgaaggacccagtgaggtctccgtgaggatgcgggctccat
ccctggcctcgctcagtgggttaaggacctggcgtggctgcaagctgt
gccacaggtcgcatatgcggctcagggctggtgtggctgtggctgtgg
cgtaggccgaagctgcagctccagttctccacccctggcccgggaact
tccatgcgccacaggtacggccatactgataataataacaataatagt
aataatgataataccccacctcataggaggttacagggcccgacgagat
ggtgtttgcaaaacgcagggcactgtgcctgcgcctacggggtgccc
gacccaccgttaataatggtatcaatgactcccgtttctgaggcactt
ggcagacaccagaaatgccaggccttttccagaccctggacgcctggtc
ctcccgaccatgctgagaagtagctgttactacccacactttccacgt
gaggctcctggagcccagagacaggagtgaagctgcccagggccacac
agcacaggaggcaggaccaggatgagactgaggcttttcacaaggggag
cgtctcagccccacggcctcctgtgctgccag
GCCCTCAGAGCTCCTGACGCTCACGTCCTGGTTGGCACCCATCGTCTC
CGAGGGCACCTTCGACCCTGAGCTTCTTCATCACATCTACCAGCCACT
GAACCTGACCATCGGGCTCACGGTGTTTGCCGTGGGGAAgtgagtcgt
gggctgggcgtggggaggggtgggtatagattctgaacccccaggaatgt
atggtctggggacagacaggacccgcccaggcaccaggggaggccctg
agccaggtgctgagcaggtgggaagcacagggtcgagcgtgatggttg
caggggggcttcctggaggaagggggtctggctctggcagcgaagcag
gggagcggcccaggtgagagatcgatggcacctttgtcaggagacacc
ttgtcccccttacccccttctgcttccccctgagccgcccaggcaggtggg
gagggatagaaagcccccaaccacctcccataaatgggggtccctgg
tcgggccacacgcaggtcaagagacctgggcagagcagcccggccccc
aggagcctctctccaacacgccctcccccggcgggcccgctgccctct
gttcagcctgttctcccctctcctccctcagcctgcctggcatttcct
aaattaaccgccacctggcagcttccctcggggacccttctgggagt
cctgagagaggggcccctaatggggtcctaatgcccaaagcgctgtcca
gatgctggatggctcagcggggtcaagaccccccctcccccgccacc
ccagcccagtcagcacccagcatcacaccttccctcgatgcagccact
caccgcctgtgtctataagatgggtgtgtggtccctgcctcctaggga
gttgacgaggcctgaaggagtccctttaaaacaggagtcccttagaaca
ctgcctggcacttagtaagtgctcaataaaagttagctcaggagttcc
ctggtagcctagcggttaaggtcctggtgttgtcactgctgtggcgcg
gattggctccctggactgagaacttccacatgttgtgggtgcggggaa
aaagaaagttagctctggagttcccatcgtgactcagtggttaatgaa
tctgactagcatccatgaggacgcaggttcgatcccaggcctcgctca
gtgagttaaggatccgacattgccatgagctgtggtgaggtcgcaga
cacggctcggatctggcatgactgtggctgtggcgtaggccgtcggct
acagctctgattggaccccctagcctggaaacctccatatgccgtgggt
gcagccctcaaaagacaaacaaaaaaggttagctcagtctgtgaatgt
aagactcctcgagggtcagcctaggacggtcttaagaggctggtgctg
tgagtgtgggaatttgacaagtaaggactcggaggagcctcttgagcc
gggaagctgggaggtggaccccagcctggccgaccctgggctctgtgc
cccgtgtggtgccagcccgtggtggggactcaggcagtggccctgctg
aggcggtggtggccactgggctctcgtccacag
```

TABLE 6

| | |
|---|---|
| TGAATTCTAGCTCCGTCTGCCTACGCTGGTCCGACCGCAAGGG<br>gtgagtctgcagccggtaaggacaatcgcgctccctccgctgcgcctt<br>gtccctgccccgcgcccagccggaggaagagcgccgcgagtcccagc<br>ccgcagtggtagtcgagatgtgtgtcttcggcccaggctcctggtg<br>cagatccccggctggggcggaccgagctcggccctggctgtgagtcgg<br>cagagcgtcccccggccggcctgggccccgcgggagggagaatctcgcgg<br>agccaactgtcgagggggggccttggaggacgcttcgccccaaaccggg<br>atgggaaaactgaggtctgtagagggagggagagggattgggaacggc<br>cttgcagaggccaccgaatgagcagggccaaagccccagaactctggc<br>ccgggggatcttttgacctcgagcggatccccacagagcggccaggggtc<br>cggtgctcactgctactgtgacacaaccctcccggtacatcagggag<br>tgcgtattgcgtcttgtcccctgcaccaagcccccctctagccgaggag<br>gaccccgacgctgtggcggagcggggacgagagtgacttgcccaagat<br>tatcgccgagcgggtgcgagctgaagctcgttcctgcggtccccggga<br>gagtccaggctgccgcctcctggagcaacgccctgctgccaccccgtgc<br>ccctgctccccgcccggggggatcgcggccgcccctcgctgcgcagca<br>tcccgcttccaggcccggcgtgtcccgctgtgccggctcagagctt<br>aatttcggcgtcctcattgtctccctggggaatccctctccaagatca<br>gcccaagcgctgttgccctggtccggaggatggccgcccttcgctcgc<br>cgcaggagtttgggagggagacctgagagccaaggcaggggaccggtc<br>cttggggcacggctgcaggcttcgggtgagcaatgagcctctgtcccc<br>gggtcaacttgccagaactgccccatctgggcctagggtccagcagga<br>tgagaagatgacctggaatccacagtcccctagcggggctgcccgggg | Partial Seq. ID No. 18<br>Genomic<br>Sequence:<br>Exon 1 to<br>Intron 3 |

TABLE 6-continued

```
gagggcggagcagcaaggctggggcaactatcctccagataaggagca
ttcctttgcag
GTCTCCTCCGGACCCCGAAGACACAAGCTCAGAGCCTGACGGCCCCTG
AGAGAGGTGGGCGGATCCGCCAAGTCACACCCAGGCTCTGCAGGTGCT
CAGGCCCAGACGCTGCACCCAGAGATGCGCTGCCGCAGACTAGCCCTG
GGCCTGGGGTTCGGCCTGCTGGTGGGCGTGGCCCTCTGCTCTCTGTGg
tgagcatgcccgtggagccctccggccccacccgactcctccctctc
tcagcatctcaaccccaagcctgacccttcactgaactcccagggct
ctcatccgcctctcctgacacacctgtccttctggcgccgtaagagat
gaactagtctggacttacggattttgctttgcactggctcttttcctct
gcctggactattcttctagccatgttaacgaggaactccagtttatgc
tccaaaattcaccccaatgtgttcttctgcaaagttcctggccccc
cacccccacccccaccccgcccttgtgtgcagggtctggcatcag
gaacattcctgccccaggaatgaagggctgcatggctctataataact
gtgttgccacagaccggggctttgccatccacggttcgccagaccca
aggagtgattggtggggtggggtgggggtcccaggtgcacccctggg
ggccttcattcccactaacatggaccaagtgggttttcagcctcaggt
tcaaagtcgagtcagccagtgttcttccctcccag
GCTGTATGTGGAGAACGTGCCGCCGCCGGTCTATATCCCCTATTACCT
CCCCTGCCCTGAGATCTTgtgagtatgagacggggagaatgggcgaga
tgggaggggttttttaaggccgctttgcaggttcttacattctcagctc
aggattctgatcagtgtgattaaacagtgaggcaatttatgaacggct
gcaaatgtggagtaaaaactcccctgtttcagtcccgaggggtgccct
ttggcatgttgtgtggctctgagcctcacttgctgcacgtgtaaaagg
gggcgatagatggtacctgtgaccgtgctggtgtcacccctggcacat
aggaggtgcccaggaaagagtgcttttaggacaagacctttttgctca
atttggtgttctgcgtggattcgaggaacaaggtgcccagtctctccc
acatggcaaggctgacttttttgacagctaagtgtgacacagatcaagt
gtgatgtaggttgggacagtcccgagggtgcatctggcccctggtct
tttgctgtccatgacagcagaaggaaagtaaagcatgcatcgcaaggg
aagttcctgtcgtggctcagtggaaatggatctgacgcgtatccatga
ggatgcaggttcgatccctggcctcactcagtgggttaaggatccgt
gttgccgtgagctgtggtagattgcagacacgactcggatctggca
tggctgtggctgtggtaggccaggggctacagctccccggaacctc
catatgctgcgggtgcggccctaaaaagacaaccaaaaaaagcatgca
tcacagggagttccctggtagtctagtggttaggattcagtgcttatg
ttctaaaaagcagaaaggctgcttgcttttgaaaacagttgtgacca
caatgttttggattttatcctgtttccccggatttggccttatttt
tggcatctggtcaccattatttattctaacctgggtctgggcccct
gaaccctttcccaccaacaactttgaagcatttaggtggtttccagg
tgcccagcgttctaaattagtttgtaatgagcagctctggacataaag
cttttttcccgcctaaagatcctttcatctggtatgttcctgagccaaa
ggatatggctgggttctcatccgcttgctctccagagggaccagaccg
tcccacactcacgctcatccccgcacccctacgcaccccgccccagc
agctgcgccgccgctgggctaggactggacataccagctgtcatgaga
aacaaaacccaaaccacctcgctgattggagagatgggaaatgcagtc
tggtgtaaattacgcttctttgatttgttcggggccctcatttccccc
aggccttttccatgaattgaattctgcctccatgaacttgccctctcac
ctccttccctcccgggcctctttgctgtcctctgtccccacccttgta
tttgctacctctcttttttttttttttttttttttccttttgcca
tttcttggccgctcccccgacatatggaggttcccaggctagggtcg
aatcggactgtagccaccagcctacgccagagccacagcaacatggga
tccaagccccgtctgcgacctacaccacagttcacggcaacgccagat
ccttaacccacgagtgaggacggggatcgaacccgccacctcatggtt
cctagtcggattcatcaatcactgagccacaacgggaactccagtatt
tgctacatcttgctactttttttttcttctagtttgtctacctctt
ggttcttctgaggggttttgtgtgtgtgttgtgatagattgaggctgg
agatttgtgactttatttaatgtttagttatgtatgtatttattggcc
acacccacggcatatggaagttcccaggcgaggggttgaatcggagcc
ccagctgccagcctacaccacagccacagcaacacaggatccgagctg
cgtctgtgacctatacccagctcacggcagcgctggatccttaactc
actgagtgagaccagggatcgaacctgcgtcctcatggatactagtcg
ggtttgttaccactgagccacgacgggaactcccgaggatagtcttta
tataaggtcagctggtgtcggcgttactcacatgtgcaaaatacagac
cttcacagccgtgcctggattgatggccgtgtaactgggtcccacaac
cacccatcaccgtgggctcaggttaagcaactcgcccaggctagaaag
tggcagaaccgggcttactgggcctttgcagcttctcagtccttctac
ccaatgcccaggcccttccagagcaacatgtttgcaagagagacagaa
aaagactttggagacaagtggtaccgggtttgaatcacagcaaccccg
gacagaccgcctctgtagaagcccagccctgcagtgggggaggtcta
agagagtctgcgtggagcctggtggggagggggtacctgtcccgtggg
ggggttcatcttggcttccctgccgagcatccctgccccggcccgg
cactaatggctgtgtctcgcctctcccaccag
```

The present invention further provides nucleotide probes and primers which hybridize to the hereinabove-described sequence (Seq. ID Nos. 3-18). Polynucleotides are provided that can be at least about 80%, 90%, 95%, 97% or 98% homologous to Seq. ID No. 3-18. Polynucleotides that hybridize under stringent conditions to Seq. ID No. 3-18 are also provided. Stringent conditions describe conditions under which hybridization will occur only if there is at least about 85%, 95% or at least 97% homology between the sequences. Alternatively, the polynucleotide can have at least 20 bases, preferably 30 bases, and more preferably at least 50 bases which hybridize to Seq. ID No. 3-18. Such polynucleotides can be used as primers and probes to detect the sequences provided herein. The probe or primer can be at least 14 nucleotides in length, and in a preferred embodiment, are at least 15, 20, 25 or 28 nucleotides in length.

III. Genetic Targeting of the Porcine FSM Synthetase Gene

Gene targeting allows for the selective manipulation of animal cell genomes. Using this technique, a particular DNA sequence can be targeted and modified in a site-specific and precise manner. Different types of DNA sequences can be targeted for modification, including regulatory regions, coding regions and regions of DNA between genes. Examples of regulatory regions include: promoter regions, enhancer regions, terminator regions and introns. By modifying these regulatory regions, the timing and level of expression of a gene can be altered. Coding regions can be modified to alter, enhance or eliminate the protein within a cell. Introns and exons, as well as inter-genic regions, are suitable targets for modification.

Modifications of DNA sequences can be of several types, including insertions, deletions, substitutions, or any combination thereof. A specific example of a modification is the inactivation of a gene by site-specific integration of a nucleotide sequence that disrupts expression of the gene product, i.e. a "knock out". For example, one approach to disrupting the porcine FSM synthetase gene is to insert a selectable marker into the targeting DNA such that homologous recombination between the targeting DNA and the target DNA can result in insertion of the selectable marker into the coding region of the target gene. For example, see FIG. 4.

a. Homologous Recombination

Homologous recombination permits site-specific modifications in endogenous genes and thus novel alterations can be engineered into the genome. A primary step in homologous recombination is DNA strand exchange, which involves a pairing of a DNA duplex with at least one DNA strand containing a complementary sequence to form an intermediate recombination structure containing heteroduplex DNA (see, for example, Radding, C. M. (1982) Ann. Rev. Genet. 16: 405; U.S. Pat. No. 4,888,274). The heteroduplex DNA can take several forms, including a three DNA strand containing triplex form wherein a single complementary strand invades the DNA duplex (Hsieh et al. (1990) Genes and Development 4: 1951; Rao et al., (1991) PNAS 88:2984)) and, when two complementary DNA strands pair with a DNA duplex, a classical Holliday recombination joint or chi structure (Holliday, R. (1964) Genet. Res. 5: 282) can form, or a double-D loop ("Diagnostic Applications of Double-D Loop Formation" U.S. Ser. No. 07/755,462, filed Sep. 4, 1991, which is incorporated herein by reference). Once formed, a heteroduplex structure can be resolved by strand breakage and exchange, so that all or a portion of an invading DNA strand is spliced into a recipient DNA duplex, adding or replacing a segment of the recipient DNA duplex. Alternatively, a heteroduplex structure can result in gene conversion, wherein a sequence of an invading strand is transferred to a recipient DNA duplex by repair of mismatched bases using the invading strand as a template (Genes, 3rd Ed. (1987) Lewin, B., John Wiley, New York, N.Y.; Lopez et al. (1987) Nucleic Acids Res. 15: 5643). Whether by the mechanism of breakage and rejoining or by the mechanism(s) of gene conversion, formation of heteroduplex DNA at homologously paired joints can serve to transfer genetic sequence information from one DNA molecule to another.

The ability of homologous recombination (gene conversion and classical strand breakage/rejoining) to transfer genetic sequence information between DNA molecules makes targeted homologous recombination a powerful method in genetic engineering and gene manipulation.

In homologous recombination, the incoming DNA interacts with and integrates into a site in the genome that contains a substantially homologous DNA sequence. In non-homologous ("random" or "illicit") integration, the incoming DNA is not found at a homologous sequence in the genome but integrates elsewhere, at one of a large number of potential locations. In general, studies with higher eukaryotic cells have revealed that the frequency of homologous recombination is far less than the frequency of random integration. The ratio of these frequencies has direct implications for "gene targeting" which depends on integration via homologous recombination (i.e. recombination between the exogenous "targeting DNA" and the corresponding "target DNA" in the genome).

A number of papers describe the use of homologous recombination in mammalian cells. Illustrative of these papers are Kucherlapati et al. (1984) Proc. Natl. Acad. Sci. USA 81:3153-3157; Kucherlapati et al. (1985) Mol. Cell. Bio. 5:714-720; Smithies et al. (1985) Nature 317:230-234; Wake et al. (1985) Mol. Cell. Bio. 8:2080-2089; Ayares et al. (1985) Genetics 111:375-388; Ayares et al. (1986) Mol. Cell. Bio. 7:1656-1662; Song et al. (1987) Proc. Natl. Acad. Sci. USA 84:6820-6824; Thomas et al. (1986) Cell 44:419-428; Thomas and Capecchi, (1987) Cell 51: 503-512; Nandi et al. (1988) Proc. Natl. Acad. Sci. USA 85:3845-3849; and Mansour et al. (1988) Nature 336:348-352; Evans and Kaufman, (1981) Nature 294:146-154; Doetschman et al. (1987) Nature 330:576-578; Thoma and Capecchi, (1987) Cell 51:503-512; Thompson et al. (1989) Cell 56:316-321.

The present invention uses homologous recombination to inactivate the porcine FSM synthetase gene in cells, such as fibroblasts. The DNA can comprise at least a portion of the gene at the particular locus with introduction of an alteration into at least one, optionally both copies, of the native gene, so as to prevent expression of a functional FSM synthetase protein. The alteration can be an insertion, deletion, replacement or combination thereof. When the alteration is introduce into only one copy of the gene being inactivated, the cells having a single unmutated copy of the target gene are amplified and can be subjected to a second targeting step, where the alteration can be the same or different from the first alteration, usually different, and where a deletion, or replacement is involved, can be overlapping at least a portion of the alteration originally introduced. In this second targeting step, a targeting vector with the same arms of homology, but containing a different mammalian selectable marker can be used. The resulting transformants are screened for the absence of a functional target antigen and the DNA of the cell can be further screened to ensure the absence of a wild-type target gene. Alternatively, homozygosity as to a phenotype can be achieved by breeding hosts heterozygous for the mutation.

Cells useful for homologous recombination include, by way of example, epithelial cells, neural cells, epidermal cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, and other muscle cells, etc. Moreover, the cells used for nuclear transfer can be obtained from different organs, e.g., skin, lung, pancreas, liver, stomach, intestine, heart, reproductive organs, bladder, kidney, urethra and other urinary organs, etc. Cells can be obtained from any cell or organ of the body, including all somatic or germ cells. Cells of particular interest include, among other lineages, stem cells, e.g. hematopoietic stem cells, embryonic stem cells, etc., the islets of Langerhans, adrenal medulla cells which can secrete dopamine, osteoblasts, osteoclasts, epithelial cells, endothelial cells, leukocytes, e.g. B- and T-lymphocytes, myelomonocytic cells, etc., neurons, glial cells, ganglion cells, retinal cells, liver cells, e.g. hepatocytes, bone marrow cells, keratinocytes, hair follicle cells, and myoblast (muscle) cells.

Fibroblast cells are a preferred somatic cell type because they can be obtained from developing fetuses and adult animals in large quantities. These cells can be easily propagated in vitro with a rapid doubling time and can be clonally propagated for use in gene targeting procedures.

Embryonic stem cells are a preferred germ cell type, an embryonic stem cell line can be employed or embryonic stem cells can be obtained freshly from a host, such as a porcine animal. The cells can be grown on an appropriate fibroblast-feeder layer or grown in the presence of leukemia inhibiting factor (LIF).

b. Targeting Vectors

Cells homozygous at a targeted locus can be produced by introducing DNA into the cells, where the DNA has homology to the target locus and includes a marker gene, allowing for selection of cells comprising the integrated construct. The homologous DNA in the target vector will recombine with the chromosomal DNA at the target locus. The marker gene can be flanked on both sides by homologous DNA sequences, a 3'recombination arm and a 5' recombination arm. Methods for the construction of targeting vectors have been described in the art, see, for example, Dai et al. (2002) Nature Biotechnology 20: 251-255; WO 00/51424, FIG. 6.

Various constructs can be prepared for homologous recombination at a target locus. Usually, the construct can include at least 50 bp, 100 bp, 500 bp, 1 kbp, 2 kbp, 4 kbp, 5 kbp, 10 kbp, 15 kbp, 20 kbp, or 50 kbp of sequence homologous with the target locus. The sequence can include any contiguous sequence of the porcine FSM synthetase gene, including at least 5, 10, 15, 17, 20 or 25 contiguous nucleotides of Seq. ID Nos. 3-18 or any combination or fragment thereof. Fragments of Seq. ID Nos. 3-18 can include any contiguous nucleic acid or peptide sequence that includes at least about 10 bp, 15 bp, 17 bp, 20 bp, 50 bp, 100 bp, 500 bp, 1 kbp, 5 kbp or 10 kpb.

In particular embodiments, the construct can contain any contiguous nucleic acid sequence at least about 1335 bp, 1340 bp, 1350 bp, 1375 bp, 1400 bp, 1500 bp, 1600 bp, 1700 bp, 2000 bp, 5000 bp or 10,000 bp of Seq ID No. 16 are provided. In another embodiment, the construct can contain any contiguous nucleic acid sequence at least about 135 bp, 140 bp, 145 bp, 150 bp, 175 bp, 200 bp, 250 bp, 300 bp, 400 bp, 500 bp, 600 bp, 700 bp, 800 bp, 900 bp, 1000 bp, 1200 bp, 1335 bp, 1340 bp, 1350 bp, 1375 bp, 1400 bp, 1500 bp, 1600 bp, 1700 bp, 2000 bp, 5000 bp or 10,000 bp of Seq ID No. 17 are provided. In another embodiment, the construct can contain any contiguous nucleic acid sequence at least about 10 bp, 15 bp, 17 bp, 20 bp, 50 bp, 100 bp, 135 bp, 140 bp, 145 bp, 150 bp, 175 bp, 200 bp, 250 bp, 300 bp, 400 bp, 500 bp, 600 bp, 700 bp, 800 bp, 900 bp, 1000 bp, 1200 bp, 1335 bp, 1340 bp, 1350 bp, 1375 bp, 1400 bp, 1500 bp, 1600 bp, 1700 bp, 2000 bp, 5000 bp or 10,000 bp of Seq ID No. 18 are provided. In other embodiments, the construct can contain The construct can also include a nucleotide sequence homologous to any of Seq. ID Nos. 3-18 having at least 99%, at least 95%, at least 90%, at least 85%, at least 80%, at least 70%, at least 60%, at least 50%, at least 40% or at least 25% amino acid identity or similarity to any of Seq. ID Nos. 3-18. Alternatively, the percentage of identity or similarity to any of Seq. ID Nos. 3-18 can be determined using BLASTP with the default parameters, BLASTX with the default parameters, or TBLASTN with the default parameters. (Altschul, S. F. et al. (1997) Gapped BLAST and PSI-BLAST: A New Generation of Protein Database Search Programs, Nucleic Acid Res. 25: 3389-3402).

The construct can include a sequence which encodes a polypeptide comprising the amino acid sequence of Seq. ID No. 2 or a nucleotide sequence encoding a polypeptide comprising an amino acid sequence which is homologous to Seq. ID No. 2. The construct can also include a nucleotide sequence encoding a polypeptide comprising an amino acid sequence homologous to Seq. ID No. 2 having at least 99%, at least 95%, at least 90%, at least 85%, at least 80%, at least 70%, at least 60%, at least 50%, at least 40% or at least 25% amino acid identity or similarity to a polypeptide comprising the sequence of Seq. ID No. 2 or a nucleotide sequence encoding an amino acid sequence having at least 99%, at least 95%, at least 90%, at least 85%, at least 80%, at least 70%, at least 60%, at least 50%, at least 40% or at least 25% amino acid identity or similarity to a fragment comprising at least 5, 10, 15, 20, 25, 30, 35, 40, 50, 75, 100, 150, 200, 250, 300 or 350 consecutive amino acids of Seq. ID No. 2. The percentage of similarity or identity to Seq. ID No. 2 can be determined using the FASTA version 3.0t78 algorithm with the default parameters. Alternatively, the percentage of identity or similarity to Seq. ID No. 2 can be determined using BLASTP with the default parameters, BLASTX with the default parameters, or TBLASTN with the default parameters. (Altschul, S. F. et al. (1997) Gapped BLAST and PSI-BLAST: A New Generation of Protein Database Search Programs, Nucleic Acid Res. 25: 3389-3402).

Various considerations can be involved in determining the extent of homology of target DNA sequences, such as, for example, the size of the target locus, availability of sequences, relative efficiency of double cross-over events at the target locus and the similarity of the target sequence with other sequences.

The targeting DNA can include a sequence in which DNA substantially isogenic flanks the desired sequence modifications with a corresponding target sequence in the genome to be modified. The substantially isogenic sequence can be at least about 95%, 97-98%, 99.0-99.5%, 99.6-99.9%, or 100% identical to the corresponding target sequence (except for the desired sequence modifications). The targeting DNA and the target DNA preferably can share stretches of DNA at least about 75, 150 or 500 base pairs that are 100% identical. Accordingly, targeting DNA can be derived from cells closely related to the cell line being targeted; or the targeting DNA can be derived from cells of the same cell line or animal as the cells being targeted.

The DNA constructs can be designed to modify the endogenous, target porcine FSM synthetase gene. The homologous sequence for targeting the construct can have one or more deletions, insertions, substitutions or combinations thereof. The alteration can be the insertion of a selectable marker gene fused in reading frame with the upstream sequence of the target gene.

Suitable selectable marker genes include, but are not limited to: genes conferring the ability to grow on certain media substrates, such as the tk gene (thymidine kinase) or the hprt gene (hypoxanthine phosphoribosyltransferase) which confer the ability to grow on HAT medium (hypoxanthine, aminopterin and thymidine); the bacterial gpt gene (guanine/xanthine phosphoribosyltransferase) which allows growth on MAX medium (mycophenolic acid, adenine, and xanthine). See Song et al. (1987) Proc. Nat'l Acad. Sci. U.S.A. 84:6820-6824. See also Sambrook et al. (1989) Molecular Cloning—A Laboratory Manual, Cold Spring Harbor Laboratory, Cold Spring Harbor, N.Y., see chapter 16. Other examples of selectable markers include: genes conferring resistance to compounds such as antibiotics, genes conferring the ability to grow on selected substrates, genes encoding proteins that produce detectable signals such as luminescence, such as green fluorescent protein, enhanced green fluorescent protein (eGFP). A wide variety of such markers are known and available, including, for example, antibiotic resistance genes such as the neomycin resistance gene (neo) (Southern, P., and P. Berg, (1982) J. Mol. Appl. Genet. 1:327-341); and the hygromycin resistance gene (hyg) (Nucleic Acids Research 11:6895-6911 (1983), and Te Riele et al. (1990) Nature 348: 649-651). Selectable marker genes that emit detectable signals are further provided in Table 7.

TABLE 7

SELECTABLE MARKER GENES THAT EMIT DETECTABLE SIGNALS

| Patent No. | Title |
|---|---|
| 6,319,669 | Modified green fluorescent proteins |
| 6,316,181 | Establishment of cell lines with persistent expression of a green fluorescent protein (GFP) using a pIRES/EGFP DNA vector construct |
| 6,303,373 | Method of measuring plasma membrane targeting of GLUT4 |
| 6,291,177 | Assay for agents which alter G-protein coupled receptor activity |
| 6,284,519 | Cell systems having specific interaction of peptide binding pairs |
| 6,284,496 | DNA vector for determining the presence of out-of-reading-frame mutations |
| 6,280,934 | Assay for agents which alter G-protein coupled receptor activity |
| 6,274,354 | Methods using cre-lox for production of recombinant adeno-associated viruses |
| 6,270,958 | Detection of negative-strand RNA viruses |
| 6,268,201 | IniB, iniA and iniC genes of mycobacteria and methods of use |
| 6,265,548 | Mutant Aequorea victoria fluorescent proteins having increased cellular fluorescence |
| 6,261,760 | Regulation of the cell cycle by sterols |
| 6,255,558 | Gene expression |
| 6,255,071 | Mammalian viral vectors and their uses |
| 6,251,677 | Hybrid adenovirus-AAV virus and methods of use thereof |
| 6,251,602 | Cell systems having specific interaction of peptide binding pairs |
| 6,251,582 | Alternative G-coupled receptors associated with retroviral entry into cells, methods of identifying the same and diagnostic and therapeutic uses thereof |
| 6,251,384 | Metastasis models using green fluorescent protein (GFP) as a marker |
| 6,248,558 | Sequence and method for genetic engineering of proteins with cell membrane translocating activity |
| 6,248,550 | Assays for protein kinases using fluorescent protein substrates |
| 6,248,543 | Compositions and methods for screening antimicrobials |
| 6,232,107 | Luciferases, fluorescent proteins, nucleic acids encoding the luciferases and fluorescent proteins and the use thereof in diagnostics, high throughput screening and novelty items |
| 6,228,639 | Vectors and methods for the mutagenesis of mammalian genes |
| 6,225,082 | Myelin basic protein mRNA transport and translation enhancer sequences |
| 6,221,612 | Photon reducing agents for use in fluorescence assays |
| 6,218,185 | Piggybac transposon-based genetic transformation system for insects |
| 6,214,567 | Immortalized human keratinocyte cell line |

TABLE 7-continued

SELECTABLE MARKER GENES THAT EMIT DETECTABLE SIGNALS

| Patent No. | Title |
|---|---|
| 6,214,563 | Photon reducing agents for reducing undesired light emission in assays |
| 6,210,922 | Serum free production of recombinant proteins and adenoviral vectors |
| 6,210,910 | Optical fiber biosensor array comprising cell populations confined to microcavities |
| 6,203,986 | Visualization of RNA in living cells |
| 6,197,928 | Fluorescent protein sensors for detection of analytes |
| 6,180,343 | Green fluorescent protein fusions with random peptides |
| 6,172,188 | Fluorescent proteins |
| 6,153,409 | Process for continuous optimized protein production in insect larvae |
| 6,150,176 | Fluorescent protein sensors for measuring the pH of a biological sample |
| 6,146,826 | Green fluorescent protein |
| 6,140,132 | Fluorescent protein sensors for measuring the pH of a biological sample |
| 6,136,539 | Compositions and methods for the inhibition of MUC-5 mucin gene expression |
| 6,136,538 | Silent inducible virus replicons and uses thereof |
| 6,133,429 | Chromophores useful for the preparation of novel tandem conjugates |
| 6,130,313 | Rapidly degrading GFP-fusion proteins |
| 6,124,128 | Long wavelength engineered fluorescent proteins |
| 6,110,711 | Method of defining cell types by probing comprehensive expression libraries with amplified RNA |
| 6,096,865 | Mutants of the green fluorescent protein having improved fluorescent properties at 37 degrees |
| 6,096,717 | Method for producing tagged genes transcripts and proteins |
| 6,093,808 | I.kappa.BEGFP constructs, cell lines and methods of use |
| 6,090,919 | FACS-optimized mutants of the green fluorescent protein (GFP) |
| 6,083,690 | Methods and compositions for identifying osteogenic agents |
| 6,077,707 | Long wavelength engineered fluorescent proteins |
| 6,066,476 | Modified green fluorescent proteins |
| 6,060,247 | Post-mitotic neurons containing adenovirus vectors that modulate apoptosis and growth |
| 6,054,321 | Long wavelength engineered fluorescent proteins |
| 6,037,133 | I.kappa.BEGFP constructs, cell lines and methods of use |
| 6,027,881 | Mutant Aequorea victoria fluorescent proteins having increased cellular fluorescence |
| 6,025,192 | Modified retroviral vectors |
| 6,020,192 | Humanized green fluorescent protein genes and methods |
| 6,013,447 | Random intracellular method for obtaining optimally active nucleic acid molecules |
| 6,001,557 | Adenovirus and methods of use thereof |
| 5,994,077 | Fluorescence-based isolation of differentially induced genes |
| 5,994,071 | Assessment of prostate cancer |
| 5,993,778 | Functional expression of, and assay for, functional cellular receptors in vivo |
| 5,989,808 | Identification of compounds affecting specific interaction of peptide binding pairs |
| 5,985,577 | Protein conjugates containing multimers of green fluorescent protein |
| 5,968,773 | System and method for regulation of gene expression |
| 5,968,738 | Two-reporter FACS analysis of mammalian cells using green fluorescent proteins |
| 5,958,713 | Method of detecting biologically active substances by using green fluorescent protein |
| 5,952,236 | Enzyme-based fluorescence biosensor for chemical analysis |
| 5,948,889 | Compositions and methods for screening antimicrobials |
| 5,948,681 | Non-viral vehicles for use in gene transfer |
| 5,942,387 | Combinatorial process for preparing substituted thiophene libraries |
| 5,932,435 | Screening antisense and ribozyme nucleic acids in schizosaccharomyces pombe |
| 5,922,576 | Simplified system for generating recombinant adenoviruses |
| 5,919,445 | Use of green fluorescent protein to trace the infection of baculovirus in insects and to increase viral UV stability |
| 5,914,233 | Screening assay for the identification of agents which alter expression of PTH-rP |

Combinations of selectable markers can also be used. For example, to target porcine FSM synthetase gene, a neo gene (with or without its own promoter, as discussed above) can be cloned into a DNA sequence which is homologous to the porcine FSM synthetase gene. To use a combination of markers, the HSV-tk gene can be cloned such that it is outside of the targeting DNA (another selectable marker could be placed on the opposite flank, if desired). After introducing the DNA construct into the cells to be targeted, the cells can be selected on the appropriate antibiotics. In this particular example, those cells which are resistant to G418 and gancyclovir are most likely to have arisen by homologous recombination in which the neo gene has been recombined into the porcine FSM synthetase gene but the tk gene has been lost because it was located outside the region of the double crossover.

Deletions can be at least about 50 bp, more usually at least about 100 bp, and generally not more than about 20 kbp, where the deletion can normally include at least a portion of the coding region including a portion of or one or more exons, a portion of or one or more introns, and can or can not include a portion of the flanking non-coding regions, particularly the 5'-non-coding region (transcriptional regulatory region). Thus, the homologous region can extend beyond the coding region into the 5'-non-coding region or alternatively into the 3'-non-coding region. Insertions can generally not exceed 10 kbp, usually not exceed 5 kbp, generally being at least 50 bp, more usually at least 200 bp.

The region(s) of homology can include mutations, where mutations can further inactivate the target gene, in providing for a frame shift, or changing a key amino acid, or the mutation can correct a dysfunctional allele, etc. Usually, the mutation can be a subtle change, not exceeding about 5% of the homologous flanking sequences. Where mutation of a gene is desired, the marker gene can be inserted into an intron, so as to be excised from the target gene upon transcription.

The construct can be prepared in accordance with methods known in the art, various fragments can be brought together, introduced into appropriate vectors, cloned, analyzed and then manipulated further until the desired construct has been achieved. Various modifications can be made to the sequence, to allow for restriction analysis, excision, identification of probes, etc. Silent mutations can be introduced, as desired. At various stages, restriction analysis, sequencing, amplification with the polymerase chain reaction, primer repair, in vitro mutagenesis, etc. can be employed.

The construct can be prepared using a bacterial vector, including a prokaryotic replication system, e.g. an origin recognizable by *E. coli*, at each stage the construct can be cloned and analyzed. A marker, the same as or different from the marker to be used for insertion, can be employed, which can be removed prior to introduction into the target cell. Once the vector containing the construct has been completed, it can be further manipulated, such as by deletion of the bacterial sequences, linearization, introducing a short deletion in the homologous sequence. After final manipulation, the construct can be introduced into the cell.

Techniques which can be used to allow the DNA construct entry into the host cell include calcium phosphate/DNA coprecipitation, microinjection of DNA into the nucleus, electroporation, bacterial protoplast fusion with intact cells, transfection, or any other technique known by one skilled in the art. The DNA can be single or double stranded, linear or circular, relaxed or supercoiled DNA. For various techniques for transfecting mammalian cells, see, for example, Keown et al., Methods in Enzymology Vol. 185, pp. 527-537 (1990).

The present invention further includes recombinant constructs comprising one or more of the sequences as broadly described above (for example in Table 3). The constructs comprise a vector, such as a plasmid or viral vector, into which a sequence of the invention has been inserted, in a forward or reverse orientation. The construct can also include regulatory sequences, including, for example, a promoter, operably linked to the sequence. Large numbers of suitable vectors and promoters are known to those of skill in the art, and are commercially available. The following vectors are provided by way of example: pBs, pQE-9 (Qiagen), phagescript, PsiX174, pBluescript SK, pBsKS, pNH8a, pNH16a, pNH18a, pNH46a (Stratagene); pTrc99A, pKK223-3, pKK233-3, pDR540, pRIT5 (Pharmacia). Eukaryotic: pWLneo, pSv2cat, pOG44, pXT1, pSG (Stratagene) pSVK3, pBPv, pMSG, pSVL (Pharmaicia). Also, any other plasmids and vectors can be used as long as they are replicable and viable in the host. Vectors known in the art and those commercially available (and variants or derivatives thereof) can in accordance with the invention be engineered to include one or more recombination sites for use in the methods of the invention. Such vectors can be obtained from, for example, Vector Laboratories Inc., Invitrogen, Promega, Novagen, NEB, Clontech, Boehringer Mannheim, Pharmacia, EpiCenter, OriGenes Technologies Inc., Stratagene, PerkinElmer, Pharmingen, and Research Genetics. Other vectors of interest include eukaryotic expression vectors such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), p3'SS, pXT1, pSG5, pPbac, pMbac, pMC1neo, and pOG44 (Stratagene, Inc.), and pYES2, pAC360, pBlueBacHis A, B, and C, pVL1392, pBlueBacIII, pCDM8, pcDNA1, pZeoSV, pcDNA3 pREP4, pCEP4, and pEBVHis (Invitrogen, Corp.) and variants or derivatives thereof.

Other vectors suitable for use in the invention include pUC18, pUC19, pBlueScript, pSPORT, cosmids, phagemids, YAC's (yeast artificial chromosomes), BAC's (bacterial artificial chromosomes), P1 (*Escherichia coli* phage), pQE70, pQE60, pQE9 (quagan), pBS vectors, PhageScript vectors, BlueScript vectors, pNH8A, pNH16A, pNH18A, pNH46A (Stratagene), pcDNA3 (Invitrogen), pGEX, pTrsfus, pTrc99A, pET-5, pET-9, pKK223-3, pKK233-3, pDR540, pRIT5 (Pharmacia), pSPORT1, pSPORT2, pCMVSPORT2.0 and pSVSPORT1 (Invitrogen) and variants or derivatives thereof. Viral vectors can also be used, such as lentiviral vectors (see, for example, WO 03/059923; Tiscomia et al. PNAS 100:1844-1848 (2003)).

Additional vectors of interest include pTrxFus, pThioHis, pLEX, pTrcHis, pTrcHis2, pRSET, pBlueBacHis2, pcDNA3.1/His, pcDNA3.1(−)/Myc-His, pSecTag, pEBVHis, pPIC9K, pPIC3.5K, pAO815, pPICZ, pPICZA, pPICZB, pPICZC, pGAPZA, pGAPZB, pGAPZC, pBlueBac4.5, pBlueBacHis2, pMelBac, pSinRep5, pSinHis, pIND, pIND(SP1), pVgRXR, pcDNA2.1, pYES2, pZErO1.1, pZErO-2.1, pCR-Blunt, pSE280, pSE380, pSE420, pVL1392, pVL1393, pCDM8, pcDNA1.1, pcDNA1.1/Amp, pcDNA3.1, pcDNA3.1/Zeo, pSe, SV2, pRc/CMV2, pRc/RSV, pREP4, pREP7, pREP8, pREP9, pREP 10, pCEP4, pEBVHis, pCR3.1, pCR2.1, pCR3.1-Uni, and pCRBac from Invitrogen; λ ExCell, λ gt11, pTrc99A, pKK223-3, pGEX-1λ T, pGEX-2T, pGEX-2TK, pGEX4T-1, pGEX-4T-2, pGEX4T-3, pGEX-3x, pGEX-5X-1, pGEX-5X-2, pGEX-5X-3, pEZZ18, pRIT2T, pMC1871, pSVK3, pSVL, pMSG, pCH110, pKK232-8, pSL1180, pNEO, and pUC4K from Pharmacia; pSCREEN-1b(+), pT7Blue(R), pT7Blue-2, pCITE4abc(+), pOCUS-2, pTAg, pET-32LIC, pET-30LIC, pBAC-2 cp LIC, pBACgus-2 cp LIC, pT7Blue-2 LIC, pT7Blue-2, λ SCREEN-1, λ BlueSTAR, pET-3abcd, pET-7abc, pET9abcd, pET11abcd, pET12abc, pET-14b, pET-15b, pET-16b, pET-17b-pET-17xb, pET-19b, pET-20b(+), pET-21abcd(+), pET-22b(+), pET-23abcd(+), pET-24abcd(+), pET-25b(+), pET-26b(+), pET-27b(+), pET-28abc(+), pET-29abc(+), pET-30abc(+), pET-31b(+), pET-32abc(+), pET-33b(+), pBAC-1, pBACgus-1, pBAC4x-1, pBACgus4x-1, pBAC-3 cp, pBACgus-2 cp, pBACsurf-1, plg, Signal plg, pYX, Selecta Vecta-Neo, Selecta Vecta-Hyg, and Selecta Vecta-Gpt from Novagen; pLexA, pB42AD, pGBT9, pAS2-1, pGAD424, pACT2, pGAD GL, pGAD GH, pGAD10, pGilda, pEZM3, pEGFP, pEGFP-1, pEGFP-N, pEGFP-C, pEBFP, pGFPuv, pGFP, p6xHis-GFP, pSEAP2-Basic, pSEAP2-Contral, pSEAP2-Promoter, pSEAP2-Enhancer, pβgal-Basic, pβgal-Control, pβgal-Promoter, pβgal-Enhancer, pCMV, pTet-Off, pTet-On, pTK-Hyg, pRetro-Off, pRetro-On, pIRES1neo, pIRES1hyg, pLXSN, pLNCX, pLAPSN, pMAMneo, pMAMneo-CAT, pMAMneo-LUC, pPUR, pSV2neo, pYEX4T-1/2/3, pYEX-S1, pBacPAK-His, pBacPAK8/9, pAcUW31, BacPAK6, pTriplEx, λgt10, λgt11, pWE15, and λTriplEx from Clontech; Lambda ZAP II, pBK-CMV, pBK-RSV, pBluescript II KS +/−, pBluescript II SK +/−, pAD-GAL4, pBD-GAL4 Cam, pSurfscript, Lambda FIX II, Lambda DASH, Lambda EMBL3, Lambda EMBL4, SuperCos, pCR-Scrigt Amp, pCR-Script Cam, pCR-Script Direct, pBS +/−, pBC KS +/−, pBC SK +/−, Phagescript, pCAL-n-EK, pCAL-n, pCAL-c, pCAL-kc, pET-3abcd, pET-11abcd, pSPUTK, pESP-1, pCMVLacI, pOPRSVI/MCS, pOPI3 CAT, pXT1, pSG5, pPbac, pMbac, pMC1neo, pMC1neo Poly A, pOG44, pOG45, pFRTβGAL, pNEOβGAL, pRS403, pRS404, pRS405, pRS406, pRS413, pRS414, pRS415, and pRS416 from Stratagene.

Additional vectors include, for example, pPC86, pDBLeu, pDBTrp, pPC97, p2.5, pGAD1-3, pGAD10, pACt, pACT2, pGADGL, pGADGH, pAS2-1, pGAD424, pGBT8, pGBT9, pGAD-GAL4, pLexA, pBD-GAL4, pHISi, pHISi-1, placZi, pB42AD, pDG202, pJK202, pJG4-5, pNLexA, pYESTrp and variants or derivatives thereof.

Also, any other plasmids and vectors can be used as long as they are replicable and viable in the host.

c. Selection of Homologously Recombined Cells

The cells can then be grown in appropriately-selected medium to identify cells providing the appropriate integration. Those cells which show the desired phenotype can then be further analyzed by restriction analysis, electrophoresis, Southern analysis, polymerase chain reaction, or another technique known in the art. By identifying fragments which show the appropriate insertion at the target gene site, cells can be identified in which homologous recombination has occurred to inactivate or otherwise modify the target gene.

The presence of the selectable marker gene inserted into the porcine FSM synthetase gene establishes the integration of the target construct into the host genome. Those cells which show the desired phenotype can then be further analyzed by restriction analysis, electrophoresis, Southern analysis, polymerase chain reaction, etc to analyze the DNA in order to establish whether homologous or non-homologous recombination occurred. This can be determined by employing probes for the insert and then sequencing the 5' and 3' regions flanking the insert for the presence of the FSM synthetase gene extending beyond the flanking regions of the construct or identifying the presence of a deletion, when such deletion is introduced. Primers can also be used which are complementary to a sequence within the construct and complementary to a sequence outside the construct and at the target locus. In this way, one can only obtain DNA duplexes having both of the primers present in the complementary chains if homologous recombination has occurred. By demonstrating the presence of the primer sequences or the expected size sequence, the occurrence of homologous recombination is supported.

The polymerase chain reaction used for screening homologous recombination events is described in Kim and Smithies, (1988) Nucleic Acids Res. 16:8887-8903; and Joyner et al. (1989) Nature 338:153-156.

The cell lines obtained from the first round of targeting are likely to be heterozygous for the targeted allele. Homozygosity, in which both alleles are modified, can be achieved in a number of ways. One approach is to grow up a number of cells in which one copy has been modified and then to subject these cells to another round of targeting using a different selectable marker. Alternatively, homozygotes can be obtained by breeding animals heterozygous for the modified allele, according to traditional Mendelian genetics. In some situations, it can be desirable to have two different modified alleles. This can be achieved by successive rounds of gene targeting or by breeding heterozygotes, each of which carries one of the desired modified alleles.

IV. Genetic Manipulation of Additional Genes to Overcome Immunologic Barriers of Xenotransplantation The FSM synthetase negative homozygotes can be subject to further genetic modification. For example, one can introduce additional genetic capability into the homozygotic hosts, where the endogenous alleles have been made non-functional, to substitute, replace or provide different genetic capability to the host. Optionally, the marker gene can be revoked after homogenotization. By introducing a construct comprising substantially the same homologous DNA, possibly with extended sequences, having the marker gene portion of the original construct deleted, one can be able to obtain homologous recombination with the target locus. By using a combination of marker genes for integration, one providing positive selection and the other negative selection, in the removal step, one would select against the cells retaining the marker genes.

Porcine cells are provided that lack the porcine FSM synthetase gene and the α(1,3)GT gene. Animals lacking functional porcine FSM synthetase gene can be produced according to the present invention, and then cells from this animal can be used to knockout the α(1,3)GT gene. Homozygous α(1,3)GT-negative porcine have recently been reported (Dai et al. supra, Science 2003) Alternatively, cells from these α(1,3)GT knockout animals can be used and further modified to inactivate the porcine FSM synthetase gene.

Porcine cells are provided that lack the porcine FSM synthetase gene and produce human complement inhibiting proteins. Animals lacking functional porcine FSM synthetase gene can be produced according to the present invention, and then cells from this animal can be further modified to express human complement inhibiting proteins, such as, but not limited to, CD59 (cDNA reported by Philbrick, W. M., et al. (1990) Eur. J. Immunol. 20:87-92), human decay accelerating factor (DAF)(cDNA reported by Medof et al. (1987) Proc. Natl. Acad. Sci. USA 84: 2007), and human membrane cofactor protein (MCP) (cDNA reported by Lublin, D. et al. (1988) J. Exp. Med. 168: 181-194).

Transgenic pigs producing human complement inhibiting proteins are known in the art (see, for example, U.S. Pat. No. 6,166,288). Alternatively, cells from these transgenic pigs producing human complement inhibiting proteins can be used and further modified to inactivate the porcine FSM synthetase gene.

Porcine cells are provided that lack the porcine FSM synthetase gene and the porcine CMP N-Acetylneuraminic acid hydroxylase gene. Animals lacking functional porcine FSM synthetase gene can be produced according to the present invention, and then cells from this animal can be further modified to knockout the N-Acetylneuraminic acid hydroxylase gene (CMP NeuAc hydroxylase), the product of which plays a role in presence of the Neu5Gc epitope on cell surfaces. Neu5Gc is immunogenic in humans (H. Deicher (1962), H. Higashi et al. (1985), H. Higashi (1990), and T. Higashihara (1991)) and plays a role in xenotransplant rejection. The porcine CMP N-Acetylneuraminic acid hydroxylase has recently been identified (see U.S. Application 60/476,396). Alternatively, cells from these CMP NeuAc hydroxylase knockout animals can be used and further modified to inactivate the porcine FSM synthetase gene.

Porcine cells are provided that lack the porcine FSM synthetase gene and the porcine invariant chain gene. Animals lacking functional porcine FSM synthetase gene can be produced according to the present invention, and then cells from this animal can be used to knockout the porcine invariant chain gene. The porcine invariant chain gene has recently been reported (U.S. Application No. 60/505,212). Alternatively, cells from these porcine invariant chain gene knockout animals can be used and further modified to inactivate the porcine FSM synthetase gene.

Porcine cells are provided that lack the porcine FSM synthetase gene and the porcine isogloboside 3 synthase gene. Animals lacking functional porcine FSM synthetase gene can be produced according to the present invention, and then cells from this animal can be used to knockout the porcine iGb3 synthase gene. The porcine iGb3 synthase gene has recently been reported (U.S. Application No. 60/517,524). Alternatively, cells from these porcine iGb3 synthase gene knockout animals can be used and further modified to inactivate the porcine FSM synthetase gene.

Porcine cells are provided that lack the porcine FSM synthetase gene, the porcine invariant chain gene, the $\alpha(1,3)$GT gene, and the porcine iGb3 synthase gene. Animals lacking functional FSM synthetase gene can be produced according to the present invention, and then cells from this animal can be used to knockout the $\alpha(1,3)$GT gene, the porcine iGb3 synthase gene, and the porcine invariant chain gene. Homozygous $\alpha(1,3)$GT-negative porcine have recently been reported (Dai et al., supra, Science 2003) Alternatively, cells from these $\alpha(1,3)$GT knockout animals can be used and further modified to inactivate the porcine invariant chain gene, the porcine iGb3 synthase gene, and the porcine FSM synthetase gene. Likewise, cells from porcine invariant chain knockout animals can be used to knockout $\alpha(1,3)$GT, porcine iGb3 synthase, and FSM synthetase.

Porcine cells are provided that lack the FSM synthetase gene, the porcine invariant chain gene and produce human complement inhibiting proteins. Animals lacking functional FSM synthetase can be produced according to the present invention, and then cells from this animal can be further modified to knockout porcine invariant chain gene and to express human complement inhibiting proteins, such as, but not limited to, CD59 (cDNA reported by Philbrick, W. M., et al. (1990) Eur. J. Immunol. 20:87-92), human decay accelerating factor (DAF)(cDNA reported by Medof et al. (1987) Proc. Natl. Acad. Sci. USA 84: 2007), and human membrane cofactor protein (MCP) (cDNA reported by Lublin, D. et al. (1988) J. Exp. Med. 168: 181-194).

Transgenic pigs producing human complement inhibiting proteins are known in the art (see, for example, U.S. Pat. No. 6,166,288). Alternatively, cells from these transgenic pigs producing human complement inhibiting proteins can be used and further modified to inactivate the porcine FSM synthetase gene and the porcine invariant chain gene. Likewise, cells from transgenic pigs lacking the porcine invariant chain gene can be modified to knockout the porcine FSM synthetase gene and express human complement inhibiting proteins, such as, but not limited to, CD59, human decay accelerating factor (DAF), and human membrane cofactor protein (MCP).

Porcine cells are provided that lack the FSM synthetase gene, the porcine invariant chain gene and the porcine CMP N-Acetylneuraminic acid hydroxylase gene. Animals lacking functional porcine FSM synthetase gene can be produced according to the present invention, and then cells from this animal can be further modified to knockout the porcine invariant chain gene and the porcine N-Acetylneuraminic acid hydroxylase gene (CMP NeuAc hydroxylase), the product of which plays a role in presence of the Neu5Gc epitope on cell surfaces. Neu5Gc is immunogenic in humans (H. Deicher (1962), H. Higashi et al. (1985), H. Higashi (1990), and T. Higashihara (1991)) and plays a role in xenotransplant rejection. The porcine CMP N-Acetylneuraminic acid hydroxylase has recently been identified (see U.S. Ser. No. 60/476, 396). Alternatively, cells from these CMP NeuAc hydroxylase knockout animals can be used and further modified to inactivate the FSM synthetase gene and the porcine invariant chain gene. Likewise, cells lacking the porcine invariant chain gene can be further modified to knockout the porcine FSM synthetase gene and the porcine CMP NeuAc hydroxylase gene.

Porcine cells are provided that lack the FSM synthetase gene, the porcine invariant chain gene, the porcine iGb3 synthase gene, and the porcine CMP N-Acetylneuraminic acid hydroxylase gene. Animals lacking functional porcine FSM synthetase gene can be produced according to the present invention, and then cells from this animal can be further modified to knockout the porcine invariant chain gene, the porcine iGb3 synthase gene, and the porcine N-Acetylneuraminic acid hydroxylase gene (CMP NeuAc hydroxylase), the product of which plays a role in presence of the Neu5Gc epitope on cell surfaces. Neu5Gc is immunogenic in humans (H. Deicher (1962), H. Higashi et al. (1985), H. Higashi (1990), and T. Higashihara (1991)) and plays a role in xenotransplant rejection. The porcine CMP N-Acetylneuraminic acid hydroxylase has recently been identified (see U.S. Ser. No. 60/476,396). Alternatively, cells from these CMP NeuAc hydroxylase knockout animals can be used and further modified to inactivate the FSM synthetase gene, the porcine iGb3 synthase gene, and the porcine invariant chain gene. Likewise, cells lacking the porcine invariant chain gene can be further modified to knockout the porcine FSM synthetase gene, the iGb3 synthase gene, and the porcine CMP NeuAc hydroxylase gene.

V. Production of Genetically Modified Animals

One approach to creating genetically altered animals that can be used with the present invention is to modify zygotes directly. For mammals, the modified zygotes can then be introduced into the uterus of a pseudopregnant female capable of carrying the animal to term. For example, if whole animals lacking the FSM synthetase gene are desired, then embryonic stem cells derived from that animal can be targeted and later introduced into blastocysts for growing the modified cells into chimeric animals. For embryonic stem cells, either an embryonic stem cell line or freshly obtained stem cells can be used. For further examples, see, for example, WO 01/23541A2.

Alternatively, by modified embryonic stem cells transgenic animals can be produced. The genetically modified embryonic stem cells can be injected into a blastocyst and then brought to term in a female host mammal in accordance with conventional techniques. Heterozygous progeny can then be screened for the presence of the alteration at the site of the target locus, using techniques such as PCR or Southern blotting. After mating with a wild-type host of the same species, the resulting chimeric progeny can then be cross-mated to achieve homozygous hosts.

After transforming embryonic stem cells with the targeting vector to alter the porcine FSM synthetase gene, the cells can be plated onto a feeder layer in an appropriate medium, e.g., fetal bovine serum enhanced DMEM. Cells containing the construct can be detected by employing a selective medium, and after sufficient time for colonies to grow, colonies can be picked and analyzed for the occurrence of homologous recombination. Polymerase chain reaction can be used, with primers within and without the construct sequence but at the target locus. Those colonies which show homologous recombination can then be used for embryo manipulating and blastocyst injection. Blastocysts can be obtained from superovulated females. The embryonic stem cells can then be trypsinized and the modified cells added to a droplet containing the blastocysts. At least one of the modified embryonic stem cells can be injected into the blastocoel of the blastocyst. After injection, at least one of the blastocysts can be returned to each uterine horn of pseudopregnant females. Females are then allowed to go to term and the resulting litters screened for mutant cells having the construct. The blastocysts are selected for different parentage from the transformed ES cells. By providing for a different phenotype of the blastocyst and the ES cells, chimeric progeny can be readily detected, and then genotyping can be conducted to probe for the presence of the modified porcine FSM synthetase gene.

VI. Somatic Cell Nuclear Transfer to Produce Cloned, Transgenic Offspring

The present invention provides a method for cloning a pig lacking a functional porcine FSM synthetase gene via somatic cell nuclear transfer. In general, the pig can be produced by a nuclear transfer process comprising the following steps: obtaining desired differentiated pig cells to be used as a source of donor nuclei; obtaining oocytes from a pig; enucleating said oocytes; transferring the desired differentiated cell or cell nucleus into the enucleated oocyte, e.g., by fusion or injection, to form nuclear transfer (NT) units; activating the resultant NT unit; and transferring said cultured NT unit to a host pig such that the NT unit develops into a fetus.

Nuclear transfer techniques or nuclear transplantation techniques are known in the art (see, for example, Campbell et al. (1995) Theriogenology, 43:181; Collas et al. (1994) Mol. Report Dev., 38:264-267; Keefer et al. (1994) Biol. Reprod., 50:935-939; Sims et al. (1993) Proc. Natl. Acad. Sci., USA, 90:6143-6147; WO 94/26884; WO 94/24274, and WO 90/03432, U.S. Pat. Nos. 4,944,384, 5,057,420, WO 97/07669, WO 97/07668, WO 98/30683, WO 00/22098, WO 004217, WO 00/51424, WO 03/055302, WO 03/005810, U.S. Pat. Nos. 6,147,276, 6,215,041, 6,235,969, 6,252,133, 6,258,998, 5,945,577, 6,525,243, 6,548,741, and Phelps et al. (Science 299:411414 (2003)).

A donor cell nucleus, which has been modified to alter the porcine FSM synthetase gene, is transferred to a recipient porcine oocyte. The use of this method is not restricted to a particular donor cell type. The donor cell can be as described in Wilmut et al. (1997) Nature 385:810; Campbell et al. (1996) Nature 380:64-66; or Cibelli et al. (1998) Science 280:1256-1258. All cells of normal karyotype, including embryonic, fetal and adult somatic cells which can be used successfully in nuclear transfer can in principle be employed. Fetal fibroblasts are a particularly useful class of donor cells. Generally suitable methods of nuclear transfer are described in Campbell et al. (1995) Theriogenology 43:181, Collas et al. (1994) Mol. Reprod. Dev. 38:264-267, Keefer et al. (1994) Biol. Reprod. 50:935-939, Sims et al. (1993) Proc. Nat'l. Acad. Sci. USA 90:6143-6147, WO-A-9426884, WO-A-9424274, WO-A-9807841, WO-A-9003432, U.S. Pat. No. 4,994,384 and U.S. Pat. No. 5,057,420. Differentiated or at least partially differentiated donor cells can also be used. Donor cells can also be, but do not have to be, in culture and can be quiescent. Nuclear donor cells which are quiescent are cells which can be induced to enter quiescence or exist in a quiescent state in vivo. Prior art methods have also used embryonic cell types in cloning procedures (see, for example, Campbell et al. (1996) Nature, 380:64-68) and Stice et al. (1996) Biol. Reprod., 20 54:100-110).

Methods for isolation of oocytes are well known in the art. Essentially, this can comprise isolating oocytes from the ovaries or reproductive tract of a pig. A readily available source of pig oocytes is slaughterhouse materials. For the combination of techniques such as genetic engineering, nuclear transfer and cloning, oocytes must generally be matured in vitro before these cells can be used as recipient cells for nuclear transfer, and before they can be fertilized by the sperm cell to develop into an embryo. This process generally requires collecting immature (prophase I) oocytes from mammalian ovaries, e.g., bovine ovaries obtained at a slaughterhouse, and maturing the oocytes in a maturation medium prior to fertilization or enucleation until the oocyte attains the metaphase II stage, which in the case of bovine oocytes generally occurs about 18-24 hours post-aspiration. This period of time is known as the "maturation period."

A metaphase II stage oocyte can be the recipient oocyte, at this stage it is believed that the oocyte can be or is sufficiently "activated" to treat the introduced nucleus as it does a fertilizing sperm. Metaphase II stage oocytes, which have been matured in vivo have been successfully used in nuclear transfer techniques. Essentially, mature metaphase II oocytes can be collected surgically from either non-superovulated or superovulated porcine 35 to 48, or 3941, hours past the onset of estrus or past the injection of human chorionic gonadotropin (hCG) or similar hormone.

After a fixed time maturation period, which ranges from about 10 to 40 hours, and preferably about 16-18 hours, the oocytes can be enucleated. Prior to enucleation the oocytes can be removed and placed in appropriate medium, such as HECM containing 1 milligram per milliliter of hyaluronidase prior to removal of cumulus cells. The stripped oocytes can then be screened for polar bodies, and the selected metaphase II oocytes, as determined by the presence of polar bodies, are then used for nuclear transfer. Enucleation follows.

Enucleation can be performed by known methods, such as described in U.S. Pat. No. 4,994,384. For example, metaphase II oocytes can be placed in either HECM, optionally containing 7.5 micrograms per milliliter cytochalasin B, for immediate enucleation, or can be placed in a suitable medium, for example an embryo culture medium such as CR1aa, plus 10% estrus cow serum, and then enucleated later, preferably not more than 24 hours later, and more preferably 16-18 hours later.

Enucleation can be accomplished microsurgically using a micropipette to remove the polar body and the adjacent cytoplasm. The oocytes can then be screened to identify those of which have been successfully enucleated. One way to screen the oocytes is to stain the oocytes with 1 microgram per milliliter 33342 Hoechst dye in HECM, and then view the oocytes under ultraviolet irradiation for less than 10 seconds. The oocytes that have been successfully enucleated can then be placed in a suitable culture medium, for example, CR1aa plus 10% serum.

A single mammalian cell of the same species as the enucleated oocyte can then be transferred into the perivitelline space of the enucleated oocyte used to produce the NT unit. The mammalian cell and the enucleated oocyte can be used to produce NT units according to methods known in the art. For example, the cells can be fused by electrofusion. Electrofusion is accomplished by providing a pulse of electricity that is sufficient to cause a transient breakdown of the plasma membrane. This breakdown of the plasma membrane is very short because the membrane reforms rapidly. Thus, if two adjacent membranes are induced to breakdown and upon reformation the lipid bilayers intermingle, small channels can open between the two cells. Due to the thermodynamic instability of such a small opening, it enlarges until the two cells become one. See, for example, U.S. Pat. No. 4,997,384 by Prather et al. A variety of electrofusion media can be used including, for example, sucrose, mannitol, sorbitol and phosphate buffered solution. Fusion can also be accomplished using Sendai virus as a fusogenic agent (Graham, Wister Inot. Symp. Monogr., 9, 19, 1969). Also, the nucleus can be injected directly into the oocyte rather than using electroporation fusion. See, for example, Collas and Barnes, (1994) Mol. Reprod. Dev., 38:264-267. After fusion, the resultant fused NT units are then placed in a suitable medium until activation, for example, CR1aa medium. Typically activation can be effected shortly thereafter, for example less than 24 hours later, or about 4-9 hours later.

The NT unit can be activated by known methods. Such methods include, for example, culturing the NT unit at subphysiological temperature, in essence by applying a cold, or actually cool temperature shock to the NT unit. This can be most conveniently done by culturing the NT unit at room temperature, which is cold relative to the physiological temperature conditions to which embryos are normally exposed. Alternatively, activation can be achieved by application of known activation agents. For example, penetration of oocytes by sperm during fertilization has been shown to activate prefusion oocytes to yield greater numbers of viable pregnancies and multiple genetically identical calves after nuclear transfer. Also, treatments such as electrical and chemical shock can be used to activate NT embryos after fusion. See, for example, U.S. Pat. No. 5,496,720 to Susko-Parrish et al. Additionally, activation can be effected by simultaneously or sequentially by increasing levels of divalent cations in the oocyte, and reducing phosphorylation of cellular proteins in the oocyte. This can generally be effected by introducing divalent cations into the oocyte cytoplasm, e.g., magnesium, strontium, barium or calcium, e.g., in the form of an ionophore. Other methods of increasing divalent cation levels include the use of electric shock, treatment with ethanol and treatment with caged chelators. Phosphorylation can be reduced by known methods, for example, by the addition of kinase inhibitors, e.g., serine-threonine kinase inhibitors, such as 6-dimethyl-aminopurine, staurosporine, 2-aminopurine, and sphingosine. Alternatively, phosphorylation of cellular proteins can be inhibited by introduction of a phosphatase into the oocyte, e.g., phosphatase 2A and phosphatase 2B.

The activated NT units can then be cultured in a suitable in vitro culture medium until the generation of cell colonies. Culture media suitable for culturing and maturation of embryos are well known in the art. Examples of known media, which can be used for embryo culture and maintenance, include Ham's F-10+10% fetal calf serum (FCS), Tissue Culture Medium-199 (TCM-199)+10% fetal calf serum, Tyrodes-Albumin-Lactate-Pyruvate (TALP), Dulbecco's Phosphate Buffered Saline (PBS), Eagle's and Whitten's media.

Afterward, the cultured NT unit or units can be washed and then placed in a suitable media contained in well plates which preferably contain a suitable confluent feeder layer. Suitable feeder layers include, by way of example, fibroblasts and epithelial cells. The NT units are cultured on the feeder layer until the NT units reach a size suitable for transferring to a recipient female, or for obtaining cells which can be used to produce cell colonies. Preferably, these NT units can be cultured until at least about 2 to 400 cells, more preferably about 4 to 128 cells, and most preferably at least about 50 cells.

The methods for embryo transfer and recipient animal management in the present invention are standard procedures used in the embryo transfer industry. Synchronous transfers are important for success of the present invention, i.e., the stage of the NT embryo is in synchrony with the estrus cycle of the recipient female. See, for example, Siedel, G. E., Jr. (1981) "Critical review of embryo transfer procedures with cattle" in Fertilization and Embryonic Development in Vitro, L. Mastroianni, Jr. and J. D. Biggers, ed., Plenum Press, New York, N.Y., page 323.

The following examples are offered by way of illustration and not by way of limitation.

EXAMPLES

I. Cells and Tissues

Porcine fetal tissues, including aorta, brain, and liver, were obtained from a local slaughterhouse. Samples to be used later for isolation of DNA or RNA were flash frozen in liquid nitrogen, whereas aortic tissue was treated with collagenase in phosphate-buffered saline and pig aortic endothelial cells (PAEC) were isolated. PAEC were maintained in Dulbecco's modified Eagle medium (DMEM, Gibco, Grand Island, N.Y.), 10,000 U of heparin sodium (Elkinns-Sinn, Inc., Cherry Hill, N.J.), 15 mg endothelium growth supplement (Collaborative Biomedical Products, Inc., Bedford, Mass.), L-glutamine, and penicillin-streptomycin. Culture flasks were kept loosely capped in a 37° C. incubator with an atmosphere of 5% $CO_2$.

II. Isolation of Nucleic Acids

To isolate porcine genomic DNA, PAEC were grown to confluence in tissue culture flasks, trypsinized briefly at 37° C., and pelleted by centrifugation. High molecular weight porcine DNA was recovered using a standard protocol involving phenol-chloroform extraction, overnight incubation with RNase A, isopropanol precipitation, and spooling of precipitated DNA.

Total RNA was extracted from fetal tissue samples and cultured PAEC using Trizol reagent (Gibco) according to the manufacturer's instructions. For experiments in which polyadenylated (poly $A^+$) RNA was used, poly $A^+$ RNA was separated from total RNA using the Dynabeads mRNA Purification Kit (Dynal, Oslo, Norway) in accord with the protocol provided. Total yield of poly A+ RNA ranged from 1-5% of total RNA.

III. Genome Walking and Long PCR Amplification of Genomic DNA

A combination strategy of PCR-based methods was employed to identify the porcine Forsmann Synthetase gene. Such PCR methods are well known in the art and described, for example, in PCR Technology, H. A. Erlich, ed., Stockton Press, London, 1989; PCR Protocols: A Guide to Methods and Applications, M. A. Innis, D. H. Gelfand, J. J. Sninsky, and T. J. White, eds., Academic Press, Inc., New York, 1990; and Ausubel et al.

5'- or 3'-RACE analyses. To identify the 5' and 3' ends of porcine Forsmann Synthetase gene transcripts, 5'- and 3'-RACE procedures were performed using the Marathon cDNA Amplification Kit (Clontech) with PAEC poly A+ RNA as template. First strand cDNA synthesis from 1 µg of poly A+ RNA was accomplished using 20 U of AMV-RT and 1 pmol of the supplied cDNA Synthesis Primer by incubating at 48° C. for 2 hr. Second strand cDNA synthesis involved incubating the entire first strand reaction with a supplied enzyme cocktail composed of RNase H, *Escherichia coli* DNA polymerase I, and *E. coli* DNA ligase at 16° C. for 1.5 hr. After blunting of the double-stranded cDNA ends by T4 DNA polymerase, the supplied Marathon cDNA Adapters were ligated to an aliquot of purified, double-stranded cDNA. Dilution of the adapter-ligated product in 10 mM tricme-KOH/0.1 mM EDTA buffer provided with the kit readied the cDNA for PCR amplification. To obtain the 5'- and 3'-most sequences of porcine Forsmann Synthetase gene transcripts, provided Marathon cDNA Amplification primer sets were paired with gene-specific and nested gene-specific primers based on the human Forsmann Synthetase gene (NCBI accession number AF163572 (2433 bp)). These primer sets are described in Table 6. By this method, oligonucleotide primers based on the human Forsmann Synthetase sequence described above are oriented in the 3' and 5' directions and are used to generate overlapping PCR fragments. These overlapping 3'- and 5'-end RACE products are combined to produce an intact full-length cDNA. This method is described, for example, in Innis et al., supra; and Frohman et al., Proc. Natl. Acad. Sci., 85:8998, 1988, and further described, for example, in U.S. Pat. No. 4,683,195.

Bands were obtained from the above method, cloned, and subjected to sequence analysis. GenBank BLAST searches with those sequences revealed homology to the human Forsmann Sythetase gene. To further confirm the sequence generated from the 5'-3' RACE strategy, PCR was performed using primer set FS-1×FS4.

Genome Walking analysis: To identify exon-intron boundaries, or 5'- or 3'-flanking region of the procine Forsmann Synthetase transcripts, porcine GenomeWalker™ libraries were constructed using a Universal GenomeWalkeer™ Library kit (Clontech, Palo Alto, Calif.). Briefly, five aliquots of porcine genomic DNA were separately digested with a single blunt-cutting restriction endonuclease (DraI, EcoRV, PvuII, ScaI, or StuI). After phenol-chloroform extraction, ethanol precipitation and resuspension of the restricted fragments, a portion of each digested aliquot was used in separate ligation reactions with the GenomeWalker adapters provided with the kit. This process created five "libraries" for use in the PCR-based cloning strategy of GenomeWalking. Primer pairs identified in Table 6 were used in a genome walking strategy. Either eLON-Gase or TaKaRa LA Taq (Takara Shuzo Co., Ltd., Shiga, Japan) enzyme was used for PCR in all GenomeWalker experiments as well as for direct long PCR of genomic DNA. The thermal cycling conditions recommended by the manufacturer were employed in all GW-PCR experiments on a Perkin Elmer Gene Amp System 9600 or 9700 thermocycler.

Subcloning and sequencing of amplified products. PCR products amplified from genomic DNA, Gene Walker-PCR (Clontech), and 5'- or 3'-RACE were gel-purified using the Qiagen Gel Extraction Kit (Qiagen, Valencia, Calif.), if necessary, then subcloned into the pCR II vector provided with the Original TA Cloning Kit (Invitrogen, Carlsbad, Calif.). Plasmid DNA minipreps of pCR II-ligated inserts were prepared with the QIAprep Spin Miniprep Kit (Qiagen) as directed. Automated fluorescent sequencing of cloned inserts was performed using an ABI 377 Automated DNA Sequence Analyzer (Applied Biosystems, Inc., Foster City, Calif.) with either the dRhodamine or BigDye Terminator Cycle Sequencing Kits (Applied Biosystems) primed with T7 and SP6 promoter primers or primers designed from internal insert sequences.

Primer synthesis. All oligonucleotides used as primers in the various PCR-based methods were synthesized on an ABI 394 DNA Synthesizer (Applied Biosystems, Inc., Foster City, Calif.) using solid phase synthesis and phosphoramidite nucleoside chemistry, unless otherwise stated.

TABLE 8

PRIMERS USED IN PCR STRATEGIES

| PRIMER NAME | SEQUENCE | | |
|---|---|---|---|
| FS-1 | 5'-ctccoctgcccagagatcttcaacatga-3' | (Seq ID No. 19) | 3' PRIMER |
| FS-3 | 5'-cccatcgtctccgagggaaccttcaaccc-3' | (Seq ID No. 20) | 3' NESTED PRIME |
| FS-2 | 5'-gaagtgacggttcaggtggctttcctcc-3' | (Seq ID No. 21) | 5' NESTED PRIMER |
| FS-4 | 5'-tcccagaggtactcggggacagcac-3' | (Seq ID No. 22) | 5' PRIMER |

This invention has been described with reference to its preferred embodiments. Variations and modifications of the invention will be obvious to those skilled in the art from the foregoing detailed description of the invention. It is intended that all of these variations and modifications be included within the scope of this invention.

We claim:

1. An isolated nucleic acid comprising at least 1,350 contiguous nucleotides of SEQ ID NO: 16 wherein the nucleic acid can be used to functionally inactivate a Forssman synthetase gene in a cell.

2. A nucleic acid construct comprising at least 1,350 contiguous nucleotides of SEQ ID NO: 16 wherein the construct can be used to functionally inactivate a Forssman synthetase gene in a cell.

3. The construct of claim 2 wherein the construct is a vector.

4. The construct of claim 2 wherein the construct is a plasmid.

5. The construct of claim 2 wherein the construct further includes a marker gene.

6. An isolated host genetically modified cell transformed with the nucleic acid of claim 1.

7. The cell of claim 6 wherein the cell is a porcine cell.

* * * * *